(12) United States Patent
Dimitrov et al.

(10) Patent No.: US 9,676,857 B2
(45) Date of Patent: Jun. 13, 2017

(54) SOLUBLE ENGINEERED MONOMERIC FC

(71) Applicant: The United States of America, as represented by the Secretary, Department of Health and Human Services, Washington, DC (US)

(72) Inventors: Dimiter S. Dimitrov, Frederick, MD (US); Tianlei Ying, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 139 days.

(21) Appl. No.: 14/385,133

(22) PCT Filed: Mar. 14, 2013

(86) PCT No.: PCT/US2013/031593
§ 371 (c)(1),
(2) Date: Sep. 12, 2014

(87) PCT Pub. No.: WO2013/138643
PCT Pub. Date: Sep. 19, 2013

(65) Prior Publication Data
US 2015/0050278 A1 Feb. 19, 2015

Related U.S. Application Data

(60) Provisional application No. 61/612,138, filed on Mar. 16, 2012.

(51) Int. Cl.
| C07K 16/18 | (2006.01) |
| C07K 16/28 | (2006.01) |
| C07K 16/46 | (2006.01) |
| C07K 14/00 | (2006.01) |
| C07K 16/00 | (2006.01) |
| C07K 16/10 | (2006.01) |
| C07K 14/005 | (2006.01) |
| C12N 7/00 | (2006.01) |
| G01N 33/544 | (2006.01) |

(52) U.S. Cl.
CPC .......... *C07K 16/283* (2013.01); *C07K 14/005* (2013.01); *C07K 16/00* (2013.01); *C07K 16/1045* (2013.01); *C12N 7/00* (2013.01); *G01N 33/544* (2013.01); *C07K 2317/52* (2013.01); *C07K 2317/524* (2013.01); *C07K 2317/526* (2013.01); *C07K 2317/565* (2013.01); *C07K 2317/569* (2013.01); *C07K 2317/94* (2013.01); *C07K 2319/30* (2013.01); *C07K 2319/74* (2013.01); *C12N 2740/16111* (2013.01)

(58) Field of Classification Search
None
See application file for complete search history.

(56) References Cited

U.S. PATENT DOCUMENTS

| 7,566,456 B2 | 7/2009 | Chen |
| 2006/0074225 A1 | 4/2006 | Chamberlain |
| 2009/0298195 A1 | 12/2009 | Rüker |
| 2010/0112080 A1 | 5/2010 | Hogarth |
| 2011/0263483 A1 | 10/2011 | Li et al. |

FOREIGN PATENT DOCUMENTS

| EP | 0227110 A2 | 7/1987 |
| WO | WO 2009/099961 | 8/2009 |
| WO | WO 2010/063785 | 6/2010 |
| WO | WO 2011/063348 | 5/2011 |
| WO | WO 2012/020096 | 2/2012 |

OTHER PUBLICATIONS

Geczy et al., J. Boil. Chem., 2012, 287(16):13137-13158.*
National Science Foundation Award Abstract # 1262435, 2012.*
Dumont et al., "Monomeric Fc fusions: impact on pharmacokinetic and biological activity of protein therapeutics," *Biodrugs* 20: 151-160 (2006).
Feng et al., "Design, expression and characterization of a soluble single-chain functional human neonatal Fc receptor," *Protein Expression and Purification* 79: 68-71 (2011).
Flanagan et al., "Soluble Fc fusion proteins for biomedical research," *Methods Molec. Biol.* 378: 33-52 (2007) (Abstract only).
Koide et al., "Teaching an old scaffold new tricks: monobodies constructed using alternative surfaces of the FN3 scaffold," *J. Mol. Biol.* 415(2): 393-405 (epub Dec. 16, 2011).
Peters et al., "Prolonged activity of factor Ix as a monomeric Fc fusion protein," *Blood* 115: 2057-2064 (Jan. 7, 2010).
Wozniak-Knopp et al., "Introducing antigen-binding sites in structural loops of immunoglobulin constant domains. Fc fragment with engineered HER2/neu-binding sites and antibody properties," *Protein Engineering Design & Selection* 23: 289-297 (2010).
Wozniak-Knopp et al., "Stabilization of the Fc fragment of human IgG1 by engineered intradomain disulfide bonds," *PLoS ONE* 7(1): e30083 1-11 (Jan. 1, 2012).
Ying et al., "Soluble monomeric IgG1 Fc," *Journal of Biological Chemistry* 287(23): 19399-19408 (Jun. 1, 2012).

* cited by examiner

*Primary Examiner* — Hong Sang
(74) *Attorney, Agent, or Firm* — Klarquist Sparkman, LLP

(57) ABSTRACT

Fc domains and CH3 domains are disclosed that bind the neonatal Fc (FcRn) receptor and are at least 99% monomeric. Monomeric Fc domain molecules and CH3 domain molecules are disclosed herein that include a monomeric Fc domain or a monomeric CH3 domain and an effector molecule. In some embodiments, the monomeric Fc or monomeric CH3 domain include amino acid substitutions and/or CDR insertions in the beta strands such that they specifically bind an antigen. Methods for using these monomeric Fc domains, monomeric CH3 domains, monomeric Fc domain molecules and CH3 domain molecules are also provided.

20 Claims, 22 Drawing Sheets

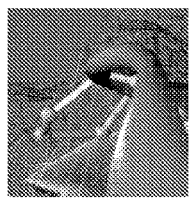 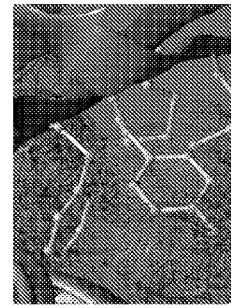 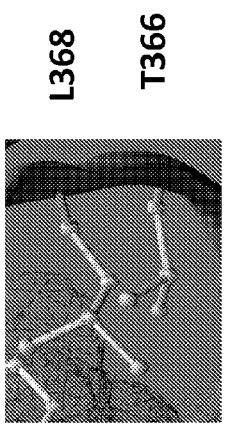 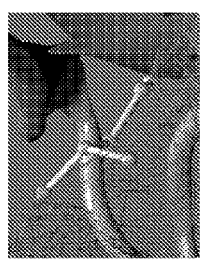 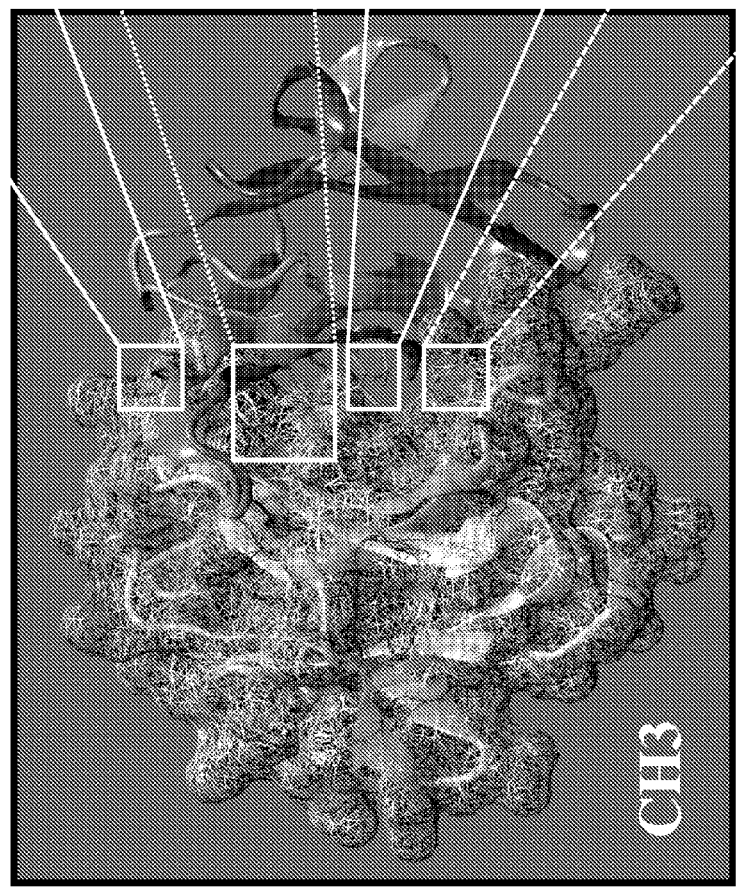
FIG. 1B

1: Marker; 2: mFc.1 before applying ProteinA/G;
3: Protein A flow-through; 4: Protein A elution;
5: Protein G flow-through; 6: Protein G elution.

FIG. 5B
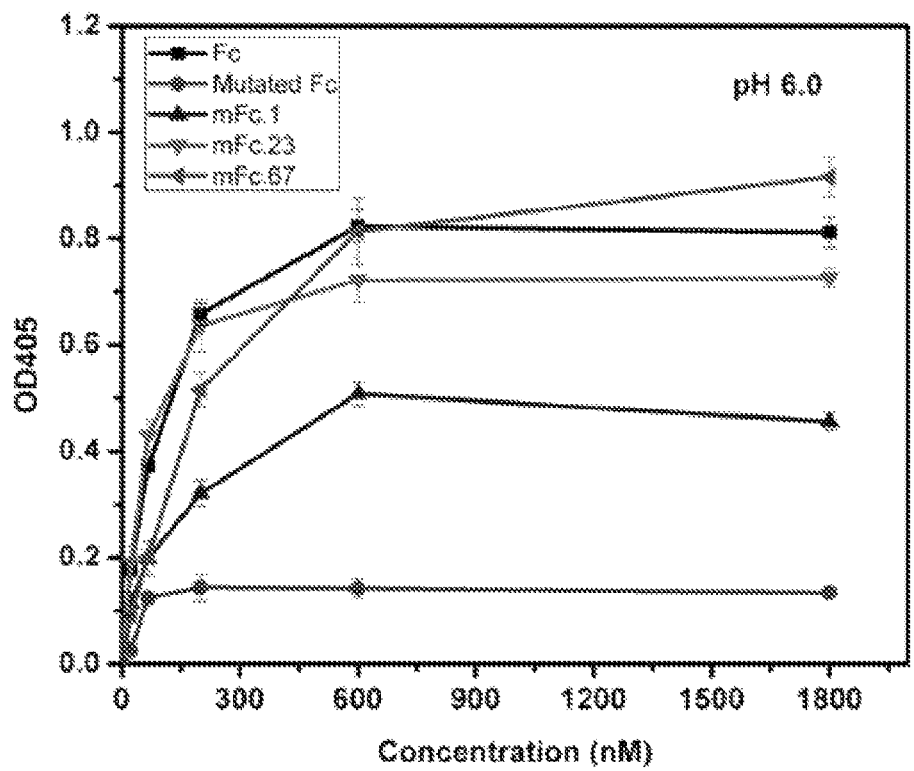
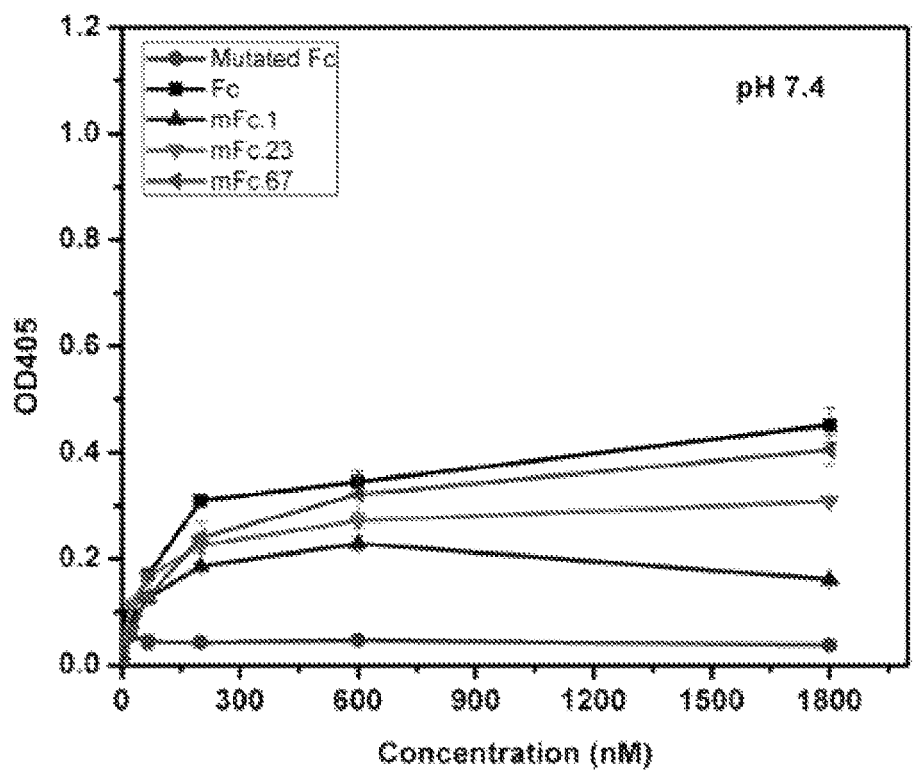

FIG. 5C
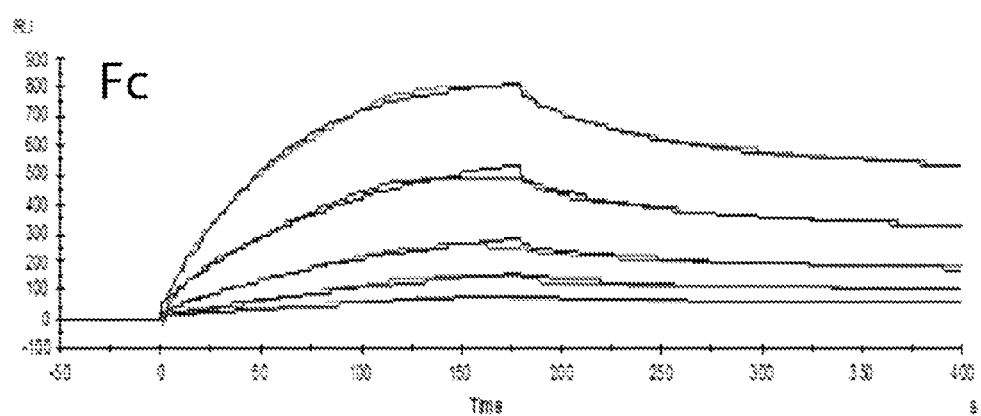
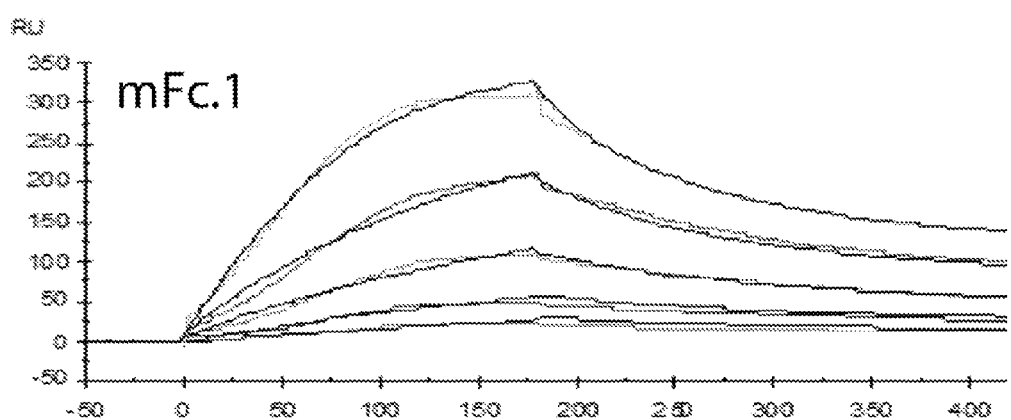

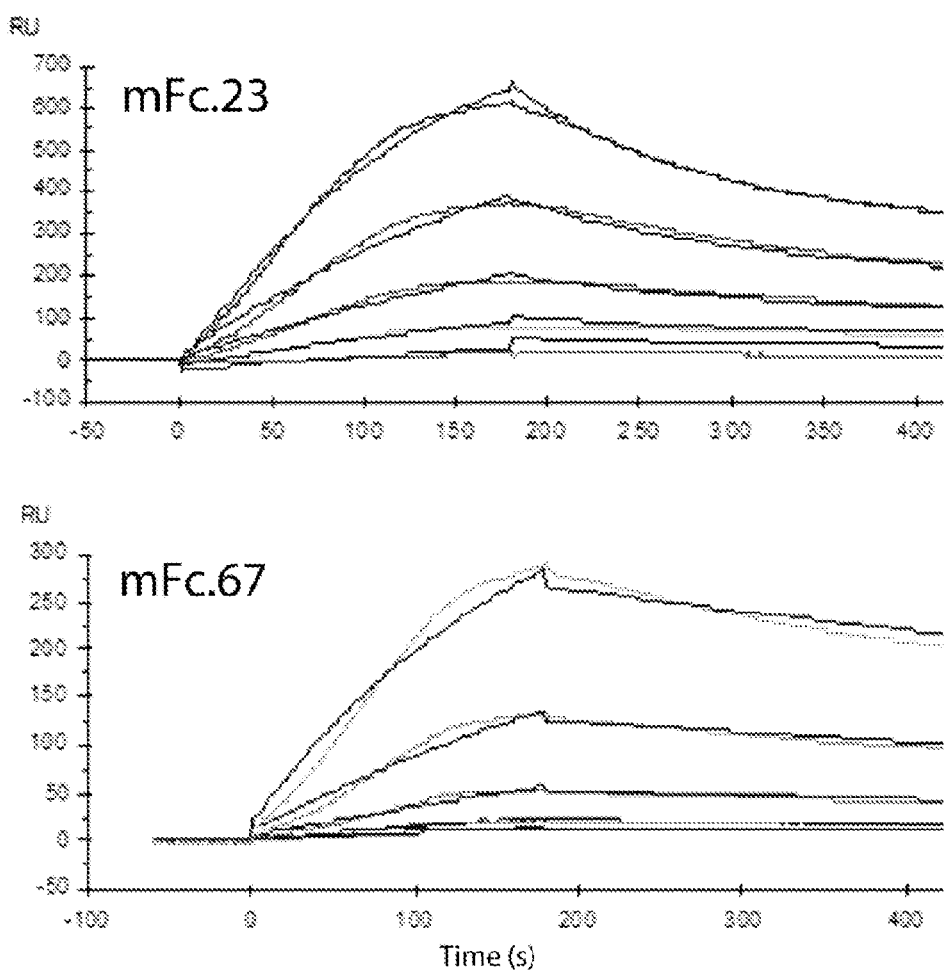

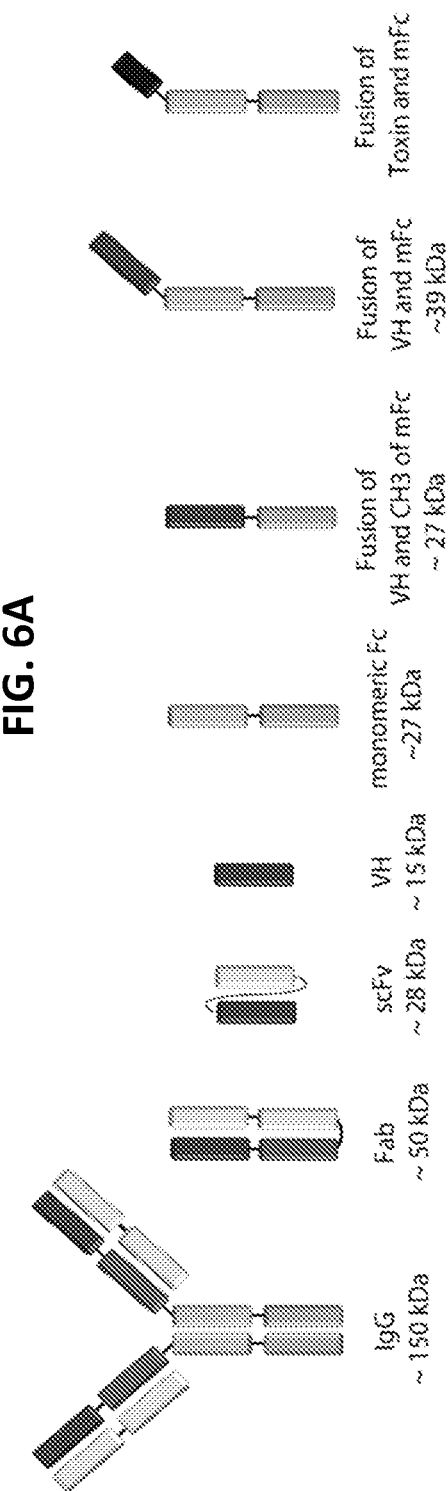

Monomeric Fc

FIG. 9

```
gg37         APELLGGPSVFLFPPTPKDTLMISRTPEVTCVVVDVSHEDPEVKFNWYVDGVEVHNAKTK   60
gn1          APELLGGPSVFLFPPSPKDTLMISRTPEVTCVVVDVSHEDPEVKFNWYVDGVEVHNAKTK   60
gn5          APELLGGPSVFLFPPKPKDTLMISRTPEVTCVVVDVSHEDPEVKFNWYVDGVEVHNAKTK   60
gg10         APELLGGPSVFLFPPKPKDTLMISRTPEVTCVVVDVSHEDPEVKFNWYVDGVEVHNAKTK   60
mFc.23_mutant APELLGGPSVFLFPPKPKDTLMISRTPEVTCVVVDVSHEDPEVKFNWYVDGVEVHNAKTK   60
             *************.:*************************************** gg37         PREEQYNSTYGVSSCLTVLHQDWLNGKEYKCKVSNKALPAPIEKTISKAKGQPREPQVYT  120
gn1          PREEQYNSTYSVASLLITVLHQDWLNGKEYKCKVSNKALPAPIEKTISKAKGQPREPQVYT  120
gn5          PREEQYNSTYRYVSVLTVLHQDWLNGKEYKCKVSNKALPAPIEKTISKAKGQPREPQVYT  120
gg10         PREEQYNSTYIVKSGLTVLHQDWLNGKEYRKVSNKALPAPIEKTISKAKGQPREPQVYT  120
mFc.23_mutant PREEQYNSTYRVVSVLTVLHQDWLNGKEYKCKVSNKALPAPIEKTISKAKGQPREPQVYT  120
             **********  *  :************:********************** gg37         SPPSRDELTKNQVSLRCHVKGFYPSDIAVEWESNGQGARG---CMNW------EDPWVPVLDSD  175
gn1          SPPSRDELTKMQVSLRCHVKGFYPSDIAVEWESNGQGAKGSSGSTWGYCMDVVWPVLDSD  180
gn5          SPPSRDELTKMQVSLRCHVKGFYPSDIAVEWESNGQGAKDRSPVAGRYGMDVVWPVLDSD  180
gg10         SPPSRDELTKMQVSLRCHVKGFYPEDIAVEWESNGQPENN---------YKTTKPVLDSD  171
mFc.23_mutant SPPSRDELTKMQVSLRCHVKGFYPSDIAVEWESNGQPENN---------YKTTKPVLDSD  171
                                                                  ****** gg37         GSFFLYGKLTVDKSRWQQGNVFSCSVMHEALHNHYTQKSLSLSPGK  221
gn1          SSFFLYSKLTVDKSRWQQGNVFSCSVMHEALHNHYTQKSLSLSPGK  226
gn5          GSFFLYSKLTVDKSRWQQGNVFSCSVMHEALHNHYTQKSLSLSPGK  226
gg10         GSFFLYSKLTVDKSRWQQGNVFSCSVMHEALHNHYTQKSLSLSPGK  217
mFc.23_mutant GSFFLYSKLTVDKSRWQQGNVFSCSVMHEALHNHYTQKSLSLSPGK  217
             ***** *.************************************
```

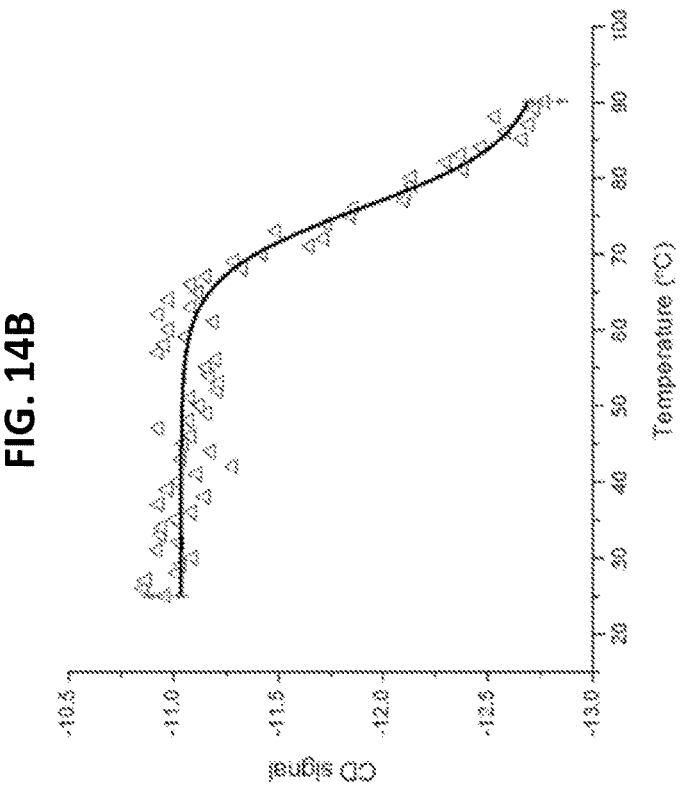
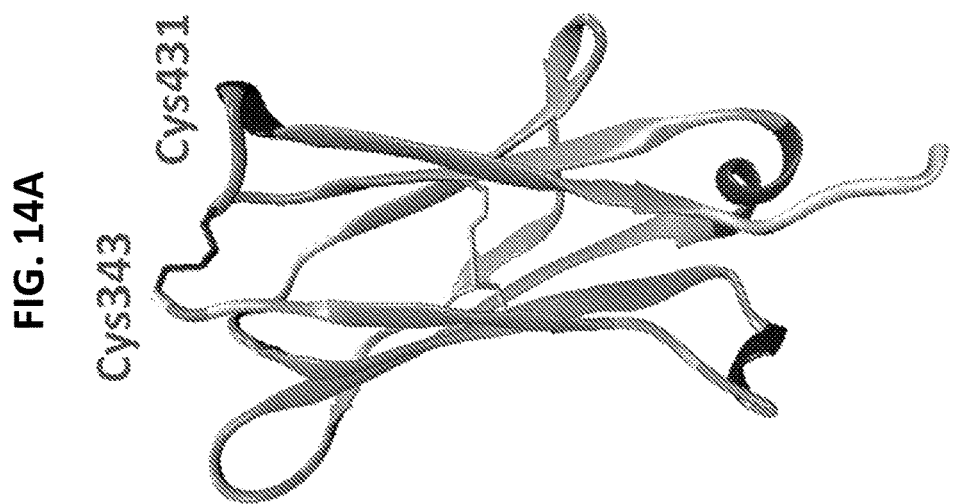
FIG. 14A
FIG. 14B

SEQUENCE LISTING

```
<160> NUMBER OF SEQ ID NOS: 48

<210> SEQ ID NO 1
<211> LENGTH: 217
<212> TYPE: PRT
<213> ORGANISM: Artificial sequence
<220> FEATURE:
<223> OTHER INFORMATION: consensus protein
<220> FEATURE:
<221> NAME/KEY: misc_feature
<222> LOCATION: (121)..(121)
<223> OTHER INFORMATION: X1 is Y, K, or S
<220> FEATURE:
<221> NAME/KEY: misc_feature
<222> LOCATION: (136)..(136)
<223> OTHER INFORMATION: X2 is Y, S, or R
<220> FEATURE:
<221> NAME/KEY: misc_feature
<222> LOCATION: (138)..(138)
<223> OTHER INFORMATION: X3 is A, L, or H
<220> FEATURE:
<221> NAME/KEY: misc_feature
<222> LOCATION: (165)..(165)
<223> OTHER INFORMATION: X4 is R, V, or K
<220> FEATURE:
<221> NAME/KEY: misc_feature
<222> LOCATION: (175)..(175)
<223> OTHER INFORMATION: X5 is R, E or F
<220> FEATURE:
<221> NAME/KEY: misc_feature
<222> LOCATION: (177)..(177)
<223> OTHER INFORMATION: X6 is M, A, K, or Y
<220> FEATURE:
<221> NAME/KEY: misc_feature
<222> LOCATION: (179)..(179)
<223> OTHER INFORMATION: X7 is A, Y, or K

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110
```

```
Pro Arg Glu Pro Gln Val Tyr Thr Xaa Pro Pro Ser Arg Asp Glu Leu
        115                 120                 125

Thr Lys Asn Gln Val Ser Leu Xaa Cys Xaa Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Xaa Pro Val Leu Asp Ser Asp Gly Ser Phe Xaa Leu
            165                 170                 175

Xaa Ser Xaa Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 2
<211> LENGTH: 217
<212> TYPE: PRT
<213> ORGANISM: Homo sapiens

<400> SEQUENCE: 2

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 3
<211> LENGTH: 217
<212> TYPE: PRT
<213> ORGANISM: Artificial sequence
<220> FEATURE:
<223> OTHER INFORMATION: modified protein

```
<400> SEQUENCE: 3

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Tyr Pro Pro Ser Arg Asp Glu Leu
        115                 120                 125

Thr Lys Asn Gln Val Ser Leu Tyr Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Arg Pro Val Leu Asp Ser Asp Gly Ser Phe Arg Leu
                165                 170                 175

Met Ser Ala Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 4
<211> LENGTH: 217
<212> TYPE: PRT
<213> ORGANISM: Artificial sequence
<220> FEATURE:
<223> OTHER INFORMATION: modified protein

<400> SEQUENCE: 4

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Lys Pro Pro Ser Arg Asp Glu Leu
        115                 120                 125
```

```
Thr Lys Asn Gln Val Ser Leu Ser Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Val Pro Val Leu Asp Ser Asp Gly Ser Phe Arg Leu
                165                 170                 175

Ala Ser Tyr Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 5
<211> LENGTH: 217
<212> TYPE: PRT
<213> ORGANISM: Artificial sequence
<220> FEATURE:
<223> OTHER INFORMATION: modified protein

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Ser Pro Pro Ser Arg Asp Glu Leu
        115                 120                 125

Thr Lys Asn Gln Val Ser Leu Arg Cys His Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Lys Pro Val Leu Asp Ser Asp Gly Ser Phe Glu Leu
                165                 170                 175

Lys Ser Ala Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 6
<211> LENGTH: 217
<212> TYPE: PRT
<213> ORGANISM: Artificial sequence
<220> FEATURE:
<223> OTHER INFORMATION: modified protein
```

```
<400> SEQUENCE: 6

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Ser Pro Pro Ser Arg Asp Glu Leu
        115                 120                 125

Thr Lys Asn Gln Val Ser Leu Arg Cys His Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Lys Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 7
<211> LENGTH: 226
<212> TYPE: PRT
<213> ORGANISM: Artificial sequence
<220> FEATURE:
<223> OTHER INFORMATION: modified protein

<400> SEQUENCE: 7

Ala Pro Glu Leu Leu Gly Gly Pro Ser Val Phe Leu Phe Pro Pro Ser
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Ser Val Ala Ser Leu Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Ser Pro Pro Ser Arg Asp Glu Leu
        115                 120                 125
```

```
Thr Lys Asn Gln Val Ser Leu Arg Cys His Val Lys Gly Phe Tyr Pro
    130                 135                 140
Ser Asp Ile Ala Val Glu Trp Glu Ser Asn Gly Gln Gly Ala Lys Gly
145                 150                 155                 160
Ser Ser Gly Ser Thr Trp Gly Tyr Gly Met Asp Val Trp Val Pro Val
                165                 170                 175
Leu Asp Ser Asp Ser Ser Phe Phe Leu Tyr Ser Lys Leu Thr Val Asp
                180                 185                 190
Lys Ser Arg Trp Gln Gln Gly Asn Val Phe Ser Cys Ser Val Met His
            195                 200                 205
Glu Ala Leu His Asn His Tyr Thr Gln Lys Ser Leu Ser Leu Ser Pro
    210                 215                 220
Gly Lys
225

<210> SEQ ID NO 8
<211> LENGTH: 226
<212> TYPE: PRT
<213> ORGANISM: Artificial sequence
<220> FEATURE:
<223> OTHER INFORMATION: modified protein

<400> SEQUENCE: 8

Ala Pro Glu Leu Leu Gly Gly Pro Ser Val Phe Leu Phe Pro Pro Leu
1               5                   10                  15
Pro Lys Asp Thr Leu Met Ile Ser Arg Thr Pro Glu Val Thr Cys Val
                20                  25                  30
Val Val Asp Val Ser His Glu Asp Pro Glu Val Lys Phe Asn Trp Tyr
            35                  40                  45
Val Asp Gly Val Glu Val His Asn Ala Lys Thr Lys Pro Arg Glu Glu
        50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Ser Pro Pro Ser Arg Asp Glu Leu
        115                 120                 125
Thr Lys Asn Gln Val Ser Leu Arg Cys His Val Lys Gly Phe Tyr Pro
    130                 135                 140
Ser Asp Ile Ala Val Glu Trp Glu Ser Asn Gly Gln Gly Ala Lys Asp
145                 150                 155                 160
Arg Ser Pro Val Ala Gly Arg Tyr Gly Met Asp Val Trp Val Pro Val
                165                 170                 175
Leu Asp Ser Asp Gly Ser Phe Phe Leu Tyr Ser Lys Leu Thr Val Asp
                180                 185                 190
Lys Ser Arg Trp Gln Gln Gly Asn Val Phe Ser Cys Ser Val Met His
            195                 200                 205
Glu Ala Leu His Asn His Tyr Thr Gln Lys Ser Leu Ser Leu Ser Pro
    210                 215                 220
Gly Lys
225
```

```
<210> SEQ ID NO 9
<211> LENGTH: 221
<212> TYPE: PRT
<213> ORGANISM: Artificial sequence
<220> FEATURE:
<223> OTHER INFORMATION: modified protein

<400> SEQUENCE: 9

Ala Pro Glu Leu Leu Gly Gly Pro Ser Val Phe Leu Phe Pro Pro Thr
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Gly Val Ser Ser Gly Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Ser Pro Pro Ser Arg Asp Glu Leu
        115                 120                 125

Thr Lys Asn Gln Val Ser Leu Arg Cys His Val Lys Gly Phe Tyr Pro
    130                 135                 140

Ser Asp Ile Ala Val Glu Trp Glu Ser Asn Gly Gln Gly Ala Arg Gly
145                 150                 155                 160

Gly Met Asn Trp Phe Asp Pro Trp Val Pro Val Leu Asp Ser Asp Gly
                165                 170                 175

Ser Phe Phe Leu Tyr Gly Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220

<210> SEQ ID NO 10
<211> LENGTH: 217
<212> TYPE: PRT
<213> ORGANISM: Artificial sequence
<220> FEATURE:
<223> OTHER INFORMATION: modified protein

<400> SEQUENCE: 10

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Ile Val Lys Ser Gly Leu Thr Val Leu His
65                  70                  75                  80

Gln Asp Trp Leu Asn Gly Lys Glu Tyr Lys Arg Lys Val Ser Asn Lys
                85                  90                  95
```

Ala Leu Pro Ala Pro Ile Glu Lys Thr Ile Ser Lys Ala Lys Gly Gln
            100                 105                 110

Pro Arg Glu Pro Gln Val Tyr Thr Ser Pro Pro Ser Arg Asp Glu Leu
        115                 120                 125

Thr Lys Asn Gln Val Ser Leu Arg Cys His Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Lys Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 11
<211> LENGTH: 22
<212> TYPE: DNA
<213> ORGANISM: Artificial sequence
<220> FEATURE:
<223> OTHER INFORMATION: primer

<400> SEQUENCE: 11
aagacagcta tcgcgattgc ag                                    22

<210> SEQ ID NO 12
<211> LENGTH: 23
<212> TYPE: DNA
<213> ORGANISM: Artificial sequence
<220> FEATURE:
<223> OTHER INFORMATION: primer

<400> SEQUENCE: 12
atcaccggaa ccagagccac cac                                   23

<210> SEQ ID NO 13
<211> LENGTH: 27
<212> TYPE: DNA
<213> ORGANISM: Artificial sequence
<220> FEATURE:
<223> OTHER INFORMATION: primer

<400> SEQUENCE: 13
tgaggagacg gtgaccaggg tgccctg                               27

<210> SEQ ID NO 14
<211> LENGTH: 35
<212> TYPE: DNA
<213> ORGANISM: Artificial sequence
<220> FEATURE:
<223> OTHER INFORMATION: primer

<400> SEQUENCE: 14
ctggtcaccg tctcctcagc acctgaactc ctggg                      35

<210> SEQ ID NO 15
<211> LENGTH: 39
<212> TYPE: DNA
<213> ORGANISM: Artificial sequence
<220> FEATURE:
<223> OTHER INFORMATION: primer

```
<400> SEQUENCE: 15
ctggtcaccg tctcctcacc ccgagaacca caggtgtac                              39

<210> SEQ ID NO 16
<211> LENGTH: 33
<212> TYPE: DNA
<213> ORGANISM: Artificial sequence
<220> FEATURE:
<223> OTHER INFORMATION: primer

<400> SEQUENCE: 16
atcgccgtgg agtgggagag cgtwtattac tgt                                    33

<210> SEQ ID NO 17
<211> LENGTH: 33
<212> TYPE: DNA
<213> ORGANISM: Artificial sequence
<220> FEATURE:
<223> OTHER INFORMATION: primer

<400> SEQUENCE: 17
atcgccgtgg agtgggagag cdtgtattac tgt                                    33

<210> SEQ ID NO 18
<211> LENGTH: 33
<212> TYPE: DNA
<213> ORGANISM: Artificial sequence
<220> FEATURE:
<223> OTHER INFORMATION: primer

<400> SEQUENCE: 18
atcgccgtgg agtgggagag caattattac tgt                                    33

<210> SEQ ID NO 19
<211> LENGTH: 33
<212> TYPE: DNA
<213> ORGANISM: Artificial sequence
<220> FEATURE:
<223> OTHER INFORMATION: primer

<400> SEQUENCE: 19
atcgccgtgg agtgggagag caatgggtac tgt                                    33

<210> SEQ ID NO 20
<211> LENGTH: 33
<212> TYPE: DNA
<213> ORGANISM: Artificial sequence
<220> FEATURE:
<223> OTHER INFORMATION: primer

<400> SEQUENCE: 20
atcgccgtgg agtgggagag caatgggcag tgt                                    33

<210> SEQ ID NO 21
<211> LENGTH: 33
<212> TYPE: DNA
<213> ORGANISM: Artificial sequence
<220> FEATURE:
<223> OTHER INFORMATION: primer

<400> SEQUENCE: 21
atcgccgtgg agtgggagag caatgggcag ggt                                    33
```

```
<210> SEQ ID NO 22
<211> LENGTH: 33
<212> TYPE: DNA
<213> ORGANISM: Artificial sequence
<220> FEATURE:
<223> OTHER INFORMATION: primer

<400> SEQUENCE: 22
gaaggagccg tcggagtcca gyccttggcc cca                          33

<210> SEQ ID NO 23
<211> LENGTH: 33
<212> TYPE: DNA
<213> ORGANISM: Artificial sequence
<220> FEATURE:
<223> OTHER INFORMATION: primer

<400> SEQUENCE: 23
gaaggagccg tcggagtcca gbccctggcc cca                          33

<210> SEQ ID NO 24
<211> LENGTH: 33
<212> TYPE: DNA
<213> ORGANISM: Artificial sequence
<220> FEATURE:
<223> OTHER INFORMATION: primer

<400> SEQUENCE: 24
gaaggagccg tcggagtcca gcacttggcc cca                          33

<210> SEQ ID NO 25
<211> LENGTH: 33
<212> TYPE: DNA
<213> ORGANISM: Artificial sequence
<220> FEATURE:
<223> OTHER INFORMATION: primer

<400> SEQUENCE: 25
gaaggagccg tcggagtcca gcacctggcc cca                          33

<210> SEQ ID NO 26
<211> LENGTH: 30
<212> TYPE: DNA
<213> ORGANISM: Artificial sequence
<220> FEATURE:
<223> OTHER INFORMATION: primer

<400> SEQUENCE: 26
gaaggagccg tcggagtcca gcacggggcc                              30

<210> SEQ ID NO 27
<211> LENGTH: 33
<212> TYPE: DNA
<213> ORGANISM: Artificial sequence
<220> FEATURE:
<223> OTHER INFORMATION: primer

<400> SEQUENCE: 27
gaaggagccg tcggagtcca gcacggggac cca                          33

<210> SEQ ID NO 28
<211> LENGTH: 30
<212> TYPE: DNA
<213> ORGANISM: Artificial sequence
<220> FEATURE:
<223> OTHER INFORMATION: primer
```

<400> SEQUENCE: 28
gccgtggagt gggaggccgt wtattactgt                                              30

<210> SEQ ID NO 29
<211> LENGTH: 30
<212> TYPE: DNA
<213> ORGANISM: Artificial sequence
<220> FEATURE:
<223> OTHER INFORMATION: primer

<400> SEQUENCE: 29
gccgtggagt gggaggccdt gtattactgt                                              30

<210> SEQ ID NO 30
<211> LENGTH: 30
<212> TYPE: DNA
<213> ORGANISM: Artificial sequence
<220> FEATURE:
<223> OTHER INFORMATION: primer

<400> SEQUENCE: 30
ggagccgtcg gagtcggtyc cttggcccca                                              30

<210> SEQ ID NO 31
<211> LENGTH: 30
<212> TYPE: DNA
<213> ORGANISM: Artificial sequence
<220> FEATURE:
<223> OTHER INFORMATION: primer

<400> SEQUENCE: 31
ggagccgtcg gagtcggtbc cctggcccca                                              30

<210> SEQ ID NO 32
<211> LENGTH: 19
<212> TYPE: DNA
<213> ORGANISM: Artificial sequence
<220> FEATURE:
<223> OTHER INFORMATION: primer

<400> SEQUENCE: 32
ctgcccattg ctctcccac                                                          19

<210> SEQ ID NO 33
<211> LENGTH: 19
<212> TYPE: DNA
<213> ORGANISM: Artificial sequence
<220> FEATURE:
<223> OTHER INFORMATION: primer

<400> SEQUENCE: 33
gtccccgtgc tggactccg                                                          19

<210> SEQ ID NO 34
<211> LENGTH: 29
<212> TYPE: DNA
<213> ORGANISM: Artificial sequence
<220> FEATURE:
<223> OTHER INFORMATION: primer

<400> SEQUENCE: 34
gactgacggt cccccagga gttcaggtg                                                29

```
<210> SEQ ID NO 35
<211> LENGTH: 44
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (16)..(16)
<223> OTHER INFORMATION: b is c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: b is c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: b is c, g, or t

<400> SEQUENCE: 35
gggaccgtca gtcnnbctcn nbcccccann bcccaaggac accc          44

<210> SEQ ID NO 36
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(14)
<223> OTHER INFORMATION: v is a, c, or g
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (20)..(20)
<223> OTHER INFORMATION: v is a, c, or g
<220> FEATURE:
<221> NAME/KEY: misc_feature
<222> LOCATION: (21)..(22)
<223> OTHER INFORMATION: n is a, c, g, or t

<400> SEQUENCE: 36
tcacgtccac cacvnngcav nngacctcag gggtc          35

<210> SEQ ID NO 37
<211> LENGTH: 25
<212> TYPE: DNA
<213> ORGANISM: Artificial sequence
<220> FEATURE:
<223> OTHER INFORMATION: primer

<400> SEQUENCE: 37
gtggtggacg tgagccacga agacc          25
```

```
<210> SEQ ID NO 38
<211> LENGTH: 22
<212> TYPE: DNA
<213> ORGANISM: Artificial sequence
<220> FEATURE:
<223> OTHER INFORMATION: primer

<400> SEQUENCE: 38
gtacgtgctg ttgtactgct cc                                              22

<210> SEQ ID NO 39
<211> LENGTH: 35
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (16)..(16)
<223> OTHER INFORMATION: b is c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: b is c, g, or t

<400> SEQUENCE: 39
caacagcacg tacnnbgtgn nbagcgtcct caccg                                35

<210> SEQ ID NO 40
<211> LENGTH: 18
<212> TYPE: DNA
<213> ORGANISM: Artificial sequence
<220> FEATURE:
<223> OTHER INFORMATION: primer

<400> SEQUENCE: 40
tttggagatg gttttctc                                                   18

<210> SEQ ID NO 41
<211> LENGTH: 43
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: b is c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: b is c, g, or t
<220> FEATURE:
<221> NAME/KEY: misc_feature
<222> LOCATION: (22)..(23)
<223> OTHER INFORMATION: n is a, c, g, or t
```

```
<220> FEATURE:
<221> NAME/KEY: misc_feature
<222> LOCATION: (24)..(24)
<223> OTHER INFORMATION: b is c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: b is c, g, or t

<400> SEQUENCE: 41
aaaaccatct ccaaannbnn bnnbnnbccc cgagaaccac agg            43

<210> SEQ ID NO 42
<211> LENGTH: 22
<212> TYPE: DNA
<213> ORGANISM: Artificial sequence
<220> FEATURE:
<223> OTHER INFORMATION: primer

<400> SEQUENCE: 42
cacggggacc gtggtcttgt ag                                  22

<210> SEQ ID NO 43
<211> LENGTH: 42
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: b is c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: b is c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: b is c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: b is c, g, or t

<400> SEQUENCE: 43
accacggtcc ccgtgnnbnn bnnbnnbggc tccttcaggc tc             42

<210> SEQ ID NO 44
<211> LENGTH: 217
<212> TYPE: PRT
<213> ORGANISM: Artificial sequence
```

```
<220> FEATURE:
<223> OTHER INFORMATION: consensus protein
<220> FEATURE:
<221> NAME/KEY: misc_feature
<222> LOCATION: (121)..(121)
<223> OTHER INFORMATION: X1 is Y, K or S
<220> FEATURE:
<221> NAME/KEY: misc_feature
<222> LOCATION: (136)..(136)
<223> OTHER INFORMATION: X2 is Y, S or R
<220> FEATURE:
<221> NAME/KEY: misc_feature
<222> LOCATION: (138)..(138)
<223> OTHER INFORMATION: X3 is A, L or H
<220> FEATURE:
<221> NAME/KEY: misc_feature
<222> LOCATION: (165)..(165)
<223> OTHER INFORMATION: X4 is R, V or K
<220> FEATURE:
<221> NAME/KEY: misc_feature
<222> LOCATION: (175)..(175)
<223> OTHER INFORMATION: X5 is R, E or F
<220> FEATURE:
<221> NAME/KEY: misc_feature
<222> LOCATION: (177)..(177)
<223> OTHER INFORMATION: X6 M, A, K, Y
<220> FEATURE:
<221> NAME/KEY: misc_feature
<222> LOCATION: (179)..(179)
<223> OTHER INFORMATION: X7 is A, Y, K

<400> SEQUENCE: 44

Ala Pro Glu Leu Leu Gly Gly Pro Ser Val Phe Cys Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Cys Thr Ile Ser Lys Ala Lys Gly Gln
            100                 105                 110

Cys Arg Glu Pro Gln Val Tyr Thr Xaa Pro Pro Ser Arg Asp Glu Leu
        115                 120                 125

Thr Lys Asn Gln Val Ser Leu Xaa Cys Xaa Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Xaa Pro Val Leu Asp Ser Asp Gly Ser Phe Xaa Leu
                165                 170                 175

Xaa Ser Xaa Leu Thr Val Asp Lys Ser Arg Trp Gln Gln Gly Asn Val
            180                 185                 190

Phe Ser Cys Ser Val Met His Glu Cys Leu His Asn His Tyr Thr Gln
        195                 200                 205

Lys Ser Leu Ser Leu Ser Pro Gly Lys
    210                 215
```

-continued

```
<210> SEQ ID NO 45
<211> LENGTH: 217
<212> TYPE: PRT
<213> ORGANISM: Artificial sequence
<220> FEATURE:
<223> OTHER INFORMATION: modified protein

<400> SEQUENCE: 45

Ala Pro Glu Leu Leu Gly Gly Pro Ser Val Phe Cys Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Cys Thr Ile Ser Lys Ala Lys Gly Gln
            100                 105                 110

Cys Arg Glu Pro Gln Val Tyr Thr Tyr Pro Pro Ser Arg Asp Glu Leu
        115                 120                 125

Thr Lys Asn Gln Val Ser Leu Tyr Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Arg Pro Val Leu Asp Ser Asp Gly Ser Phe Arg Leu
                165                 170                 175

Met Ser Ala Leu Thr Val Asp Lys Ser Arg Trp Gln Gln Gly Asn Val
            180                 185                 190

Phe Ser Cys Ser Val Met His Glu Cys Leu His Asn His Tyr Thr Gln
        195                 200                 205

Lys Ser Leu Ser Leu Ser Pro Gly Lys
    210                 215

<210> SEQ ID NO 46
<211> LENGTH: 217
<212> TYPE: PRT
<213> ORGANISM: Artificial sequence
<220> FEATURE:
<223> OTHER INFORMATION: modified protein

<400> SEQUENCE: 46

Ala Pro Glu Leu Leu Gly Gly Pro Ser Val Phe Cys Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

Ala Leu Pro Ala Pro Ile Glu Cys Thr Ile Ser Lys Ala Lys Gly Gln
              100                 105                 110

Cys Arg Glu Pro Gln Val Tyr Thr Lys Pro Pro Ser Arg Asp Glu Leu
        115                 120                 125

Thr Lys Asn Gln Val Ser Leu Ser Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Val Pro Val Leu Asp Ser Asp Gly Ser Phe Arg Leu
                165                 170                 175

Ala Ser Tyr Leu Thr Val Asp Lys Ser Arg Trp Gln Gln Gly Asn Val
            180                 185                 190

Phe Ser Cys Ser Val Met His Glu Cys Leu His Asn His Tyr Thr Gln
        195                 200                 205

Lys Ser Leu Ser Leu Ser Pro Gly Lys
    210                 215

<210> SEQ ID NO 47
<211> LENGTH: 217
<212> TYPE: PRT
<213> ORGANISM: Artificial sequence
<220> FEATURE:
<223> OTHER INFORMATION: modified protein

<400> SEQUENCE: 47

Ala Pro Glu Leu Leu Gly Gly Pro Ser Val Phe Cys Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Cys Thr Ile Ser Lys Ala Lys Gly Gln
              100                 105                 110

Cys Arg Glu Pro Gln Val Tyr Thr Ser Pro Pro Ser Arg Asp Glu Leu
        115                 120                 125

Thr Lys Asn Gln Val Ser Leu Arg Cys His Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Lys Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Cys Leu His Asn His Tyr Thr Gln
        195                 200                 205

Lys Ser Leu Ser Leu Ser Pro Gly Lys
    210                 215

```
<210> SEQ ID NO 48
<211> LENGTH: 217
<212> TYPE: PRT
<213> ORGANISM: Artificial sequence
<220> FEATURE:
<223> OTHER INFORMATION: modified protein

<400> SEQUENCE: 48

Ala Pro Glu Leu Leu Gly Gly Pro Ser Val Phe Cys Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Cys Thr Ile Ser Lys Ala Lys Gly Gln
            100                 105                 110

Cys Arg Glu Pro Gln Val Tyr Thr Ser Pro Pro Ser Arg Asp Glu Leu
        115                 120                 125

Thr Lys Asn Gln Val Ser Leu Arg Cys His Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Lys Pro Val Leu Asp Ser Asp Gly Ser Phe Glu Leu
                165                 170                 175

Lys Ser Ala Leu Thr Val Asp Lys Ser Arg Trp Gln Gln Gly Asn Val
            180                 185                 190

Phe Ser Cys Ser Val Met His Glu Cys Leu His Asn His Tyr Thr Gln
        195                 200                 205

Lys Ser Leu Ser Leu Ser Pro Gly Lys
        210                 215
```

SOLUBLE ENGINEERED MONOMERIC FC

CROSS REFERENCE TO RELATED APPLICATIONS

This is the U.S. National Stage of International Application No. PCT/US2013/031593, filed Mar. 14, 2013, which was published in English under PCT Article 21(2), which in turn claims the benefit of U.S. Provisional Application No. 61/612,138, filed Mar. 16, 2012, which is incorporated by reference herein.

PRIORITY CLAIM

This claims the benefit of U.S. Provisional Application No. 61/612,138, filed Mar. 16, 2012, which is incorporated by reference herein.

FIELD

This relates to the field of antibody constant domains, specifically to Fc domains that are monomeric and optionally bind an antigen, and the use of these Fc domains.

BACKGROUND

Major efforts are currently being made to decrease antibody size, because the full-size antibodies exhibit poor penetration into tissues, especially solid tumors, and also poor or absent binding to surface regions of some antigens that may suffer from steric hindrance and can only be accessed by molecules of smaller size. Such endeavors include the engineering of a variety of antibody fragments such as Fab, Fv, scFv, VH and VHH, and more new antibody fragment formats are under development. However, to date these antibody fragments have been of limited use in therapeutic applications, because they usually display greatly reduced half-lives compared to full-size IgG. Molecules are needed that specifically bind an antigen, but are small and have a long half-life.

The Fc domain increases the half-life of an IgG through its unique pH-dependent association with the neonatal Fc receptor (FcRn). After internalization, the Fc domain of IgG can bind to FcRn in the acidic environment of the endosome, so that the IgG is then cycled onto the cell surface and re-released into circulation. This biological system protects IgG from degradation and results in a long serum half-life. Fusions of an Fc domain and a therapeutic molecule have an extended half life. In addition, since the Fc fragment of IgG consists of a tightly packed homodimer, two therapeutic proteins are present in each molecule. Recently, monomeric Fc fusion proteins were generated in which a single active protein was fused to dimeric wild-type Fc. These smaller molecules have been shown to possess even extended half-lives compared with the dimeric version. However, the Fc domain is still relatively large (~50 kD). A need remains for monomeric Fc domains that are much smaller in size, and can be used to produce small and stable antigen binding molecules.

SUMMARY

Antibodies, including IgG, IgA, IgM, IgE and IgD, are a central part of the immune system response to antigens. The fragment crystalizable (Fc) domain is constant among wild-type antibodies; the naturally occurring Fc includes the CH2 and CH3 domains, and interacts with neonatal Fc receptor (FcRn), which increases the half-life of the antibody. In addition, a high affinity interaction that occurs between two CH3 domains makes wild-type Fc a homodimer.

Fc domains are disclosed that bind the neonatal Fc (FcRn) receptor and are at least 99% monomeric. These monomeric Fc domains include mutations in the wild type CH3 domain. In some embodiments, the monomeric Fc domains comprise, or consist of, the amino acid sequence set forth as SEQ ID NO: 1, wherein X1 is Y, K or S, wherein X2 is Y, S or R, wherein X3 is A, L or H, wherein X4 is R, V or K, wherein X5 is F, R or E; wherein X6 is Y, M, A, or K; and wherein X7 is K, A or Y. In one embodiment, the monomeric Fc domain comprises SEQ ID NO: 1, wherein $X_1$ is S, $X_2$ is R, $X_3$ is H and $X_4$ is K. In specific, non-limiting examples, the monomeric Fc includes the amino acid sequence set forth as SEQ ID NO: 3, 4, 5, or 6. In other embodiments, the monomeric Fc domains comprise, or consist of, the amino acid sequence set forth as SEQ ID NO: 44, wherein X1 is Y, K or S, wherein X2 is Y, S or R, wherein X3 is A, L or H, wherein X4 is R, V or K, wherein X5 is F, R or E; wherein X6 is Y, M, A, or K; and wherein X7 is K, A or Y.

In some embodiments, isolated CH3 domains of the monomeric Fc domains are provided. Fc domain molecules and CH3 domain molecules, such as fusion proteins including these monomeric Fc domains and CH3 domains and effector molecules are also provided herein. These molecules include a heterologous polypeptide at the N- or C-terminus of the Fc domain or CH3 domain. In some non-limiting examples, the heterologous protein is a variable domain, a cytokine, and/or or a toxin.

In additional embodiments, provided is an antigen-binding monomeric Fc domain comprising a CH2 domain and a CH3 domain, wherein (i) at least one of the beta strands of the CH2 or CH3 domain is mutated; and or wherein (ii) at least a portion of a beta strand of the CH2 domain or CH3 domain is replaced by a complementarity determining region (CDR), or a specificity determining region (SDR), from a heterologous immunoglobulin variable domain; or (iii) both, wherein the polypeptide has a molecular weight of less than about 30 kD, and wherein the polypeptide specifically binds an antigen, and wherein the monomeric Fc domain binds the neonatal Fc receptor. These molecules do not include a variable domain at the N- or C-terminus. Fc domain molecules including these antigen binding monomeric Fc domains are also provided that include an effector molecule.

In additional embodiments, a nucleic acid molecule encoding the monomeric Fc domain, antigen-binding monomeric Fc domain, CH3 domain, antigen binding CH3 domain, Fc domain molecule and CH3 domain molecule are provided. Also disclosed are expression vectors including these nucleic acids, and host cells transformed with these vectors. Libraries of nucleic acids encoding a monomeric Fc domain, and libraries of Fc domain are also provided.

In several embodiments, methods are disclosed for using these monomeric Fc domains, CH3 domains, antigen binding Fc domains, monomeric Fc domain molecules, CH3 domain molecules, antigen binding Fc domain molecules, nucleic acids and vectors. In some examples, methods are provided for treating an infection with a pathogen, a cancer, or an autoimmune disorder.

The foregoing and other features and advantages will become more apparent from the following detailed description of several embodiments, which proceeds with reference to the accompanying figures.

BRIEF DESCRIPTION OF THE FIGURES

FIG. 1B Structure of human IgG1 Fc CH3 domain, showing its dimerization interface.

FIG. 5B FcRn binding of IgG1 Fc, the Fc I253A/S254A/H435A/Y436A (IMGT numbering) mutant, mFc.1, mFc.23 and mFc.67 at pH 6.0 and 7.4 measured by ELISA.

FIGS. 5C and 5D FcRn binding of Fc, mFc.1, mFc.23 and mFc.67 measured by BIAcore. mFcs showed similar FcRn binding behavior with that of wild-type Fc.

FIG. 6A Schematic of different antibody fragments and monomeric Fc fusion proteins.

FIG. 9 is a sequence alignment of monomeric Fc domains that bind antigens. The monomeric mFc.23.4 (SEQ ID NO: 6)was used as a scaffold; this Fc contains 351S/366R/368H/395K (IMGT numbering) mutations from the wild-type Fc. In these binders, the substitutions are located in the beta sheet domains, and not in the loop regions. The binders gn1 (SEQ ID NO: 7), gn5 (SEQ ID NO: 8) and gg37 (SEQ ID NO: 9) have a grafted CDR in the CH3 domain. Binder gg10 (SEQ ID NO: 10) does not have a grafted CDR.

FIG. 14A is a schematic diagram of the mCH3 343C/431C variant (mCH3cc). Its native disulfide bond was colored yellow. The introduced disulfide bond between Cys343 and Cys431 was colored red.

FIG. 14 B is a set of plots of the change in fraction folded for mCH3cc.

SEQUENCE LISTING

Figure 1A:
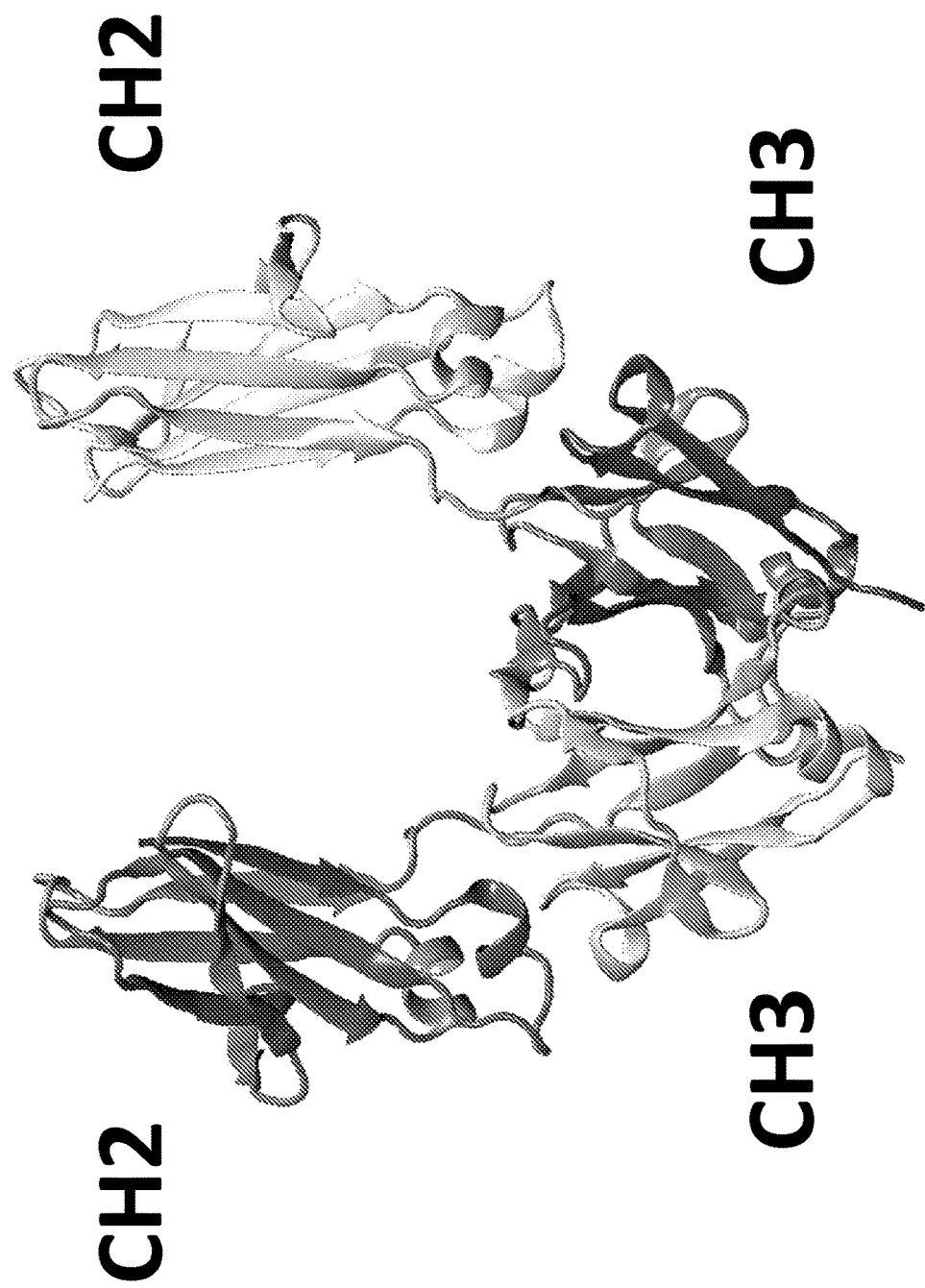
FIG. 1A Structure of human IgG1 Fc (PDB entry 2WAH).

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand where appropriate.

The Sequence Listing is submitted as an ASCII text file [4239-88390-04_Sequence_Listing.txt, Sept. 12, 2014, 38.2 KB], which is incorporated by reference herein.

SEQ ID NO: 1 is the amino acid sequence of a consensus monomeric Fc.

SEQ ID NO: 2 is the amino acid sequence of wild type Fc.

SEQ ID NO: 3 is the amino acid sequence of mFc.1.

SEQ ID NO: 4 is the amino acid sequence of mFc.67.

SEQ ID NO: 5 is the amino acid sequence of mFc.23.

SEQ ID NO: 6 is the amino acid sequence of mFc.23.4.

SEQ ID NO: 7 is the amino acid sequence of gn1.

SEQ ID NO: 8 is the amino acid sequence of gn5.

SEQ ID NO: 9 is the amino acid sequence of gg37.

SEQ ID NO: 10 is the amino acid sequence of gg10.

SEQ ID NO: 11-43 are the nucleic acid sequences of primers.

SEQ ID NO: 44 is the amino acid sequence of a consensus monomeric Fc that includes 242, 334, 344 and 431 residues mutated to cysteine.

SEQ ID NO: 45 is the amino acid sequence of mFc.1 with the 242C/334C/343C/431C mutations.

SEQ ID NO: 46 is the amino acid sequence of mFc.67 with the 242C/334C/343C/431C mutations.

SEQ ID NO: 47 is the amino acid sequence of mFc.23 with the 242C/334C/343C/431C mutations.

SEQ ID NO: 48 is the amino acid sequence of mFc.23.4 with the 242C/334C/343C/431C mutations.

DETAILED DESCRIPTION

Monoclonal antibodies have widespread therapeutic applications, and represent the largest class of biological drugs. However, antibodies have difficulty penetrating tissues due to their large size. A variety of small antibody formats, such as Fab, Fv, scFv, V$_H$ and VHH, have been developed but have relatively short half-lives. Specific monomeric Fc domains are disclosed herein. These monomeric Fc are 99% monomeric, have a molecular weight of about 27 kD, and bind to FcRn. Isolated CH3 domains of these monoclonal antibodies are also provided.

The monomeric Fc domains and CH3 domain are of use for extending half-life of any protein of interest. Suitable proteins include cytokines, toxins, receptors, ligands, enzymes, erythropoietin, chemokines, and hormones. As disclosed herein, fusion proteins of a variable domain of an antibody with a monomeric Fc provide both long half-lives and a molecular weight of approximately 40 kD, one fourth that of full-size IgG. The monomeric Fc molecules, CH3 domains and fusion proteins are stable, can bind FcRn in a pH-dependent manner, and can be produced in large quantities in bacteria.

Furthermore, monomeric Fc can serve as a novel antigen binding format and be used as a scaffold for construction of libraries containing diverse binders to various antigens. As compared to wild-type Fc, a large surface area is exposed in the present Fc monomers, due to the breaking of CH3 dimerization interface, providing more accessibility for protein engineering by designed point mutations and CDR-grafting onto monomeric Fc framework. Antigen binding molecules generated from this design have a low molecular weight, such as approximately 25 kD to 30 kD, such as approximately 27 kD, similar to that of scFv and can specifically bind an antigen. However, these molecules have a relatively long (about a day or longer) half-life in vivo compared to other molecules of similar molecular weight.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject.

Animal: Living multi-cellular vertebrate organisms, a category that includes, for example, mammals and birds. The term mammal includes both human and non-human mammals. Similarly, the term "subject" includes both human and veterinary subjects.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic antibody structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains. Each light chain contains a single constant domain (CL), while each heavy chain contains three constant domains, CH1, CH2 and CH3 (or four constant domains for IgE and IgM). See FIG. 6A for a schematic drawing of a conventional immunoglobulin molecule.

As used herein, the term "antibodies" includes intact antibodies as well as a number of well-characterized fragments having a molecular weight of about 25 to 100 kD. For instance, Fabs, Fvs, and single-chain Fvs (scFvs) that bind to target protein (or an epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) scFv, single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described, for example, by Harlow and Lane (*Using Antibodies: A Laboratory Manual*, CSHL, New York, 1999).

A "humanized" antibody is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Thus, in some embodiments, a "humanized antibody" is an antibody, such as a humanized monoclonal antibody, comprising a humanized light chain and a humanized heavy chain immunoglobulin. A humanized antibody binds to the same or similar antigen as the donor antibody that provides the CDRs. The acceptor framework of a humanized immunoglobulin may have a limited number of substitutions by amino acids taken from the donor framework. Humanized molecules can have additional conservative amino acid substitutions which have substantially no effect on antigen binding or other immunoglobulin functions. These molecules can be constructed by means of genetic engineering (for example, see U.S. Pat. No. 5,585,089).

Antigen: A compound, composition, or substance that can stimulate the production of antibodies or a T-cell response in an animal, including compositions that are injected or absorbed into an animal. An antigen reacts with the products of specific humoral or cellular immunity.

Autoimmune disease: A disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

Beta Sheet: An assembly of a protein that consists of at least two beta strands connected laterally by at least two or three backbone hydrogen bonds, forming a generally twisted, pleated sheet. A beta strand (also β strand) is a stretch of polypeptide chain typically 3 to 10 amino acids long with backbone in an almost fully extended conformation. Generally, a beta strand is a single continuous stretch of amino acids adopting such an extended conformation and involved in backbone hydrogen bonds to at least one other strand, so that they form a beta sheet. In the beta sheet, the majority of beta strands are arranged adjacent to other strands and form an extensive hydrogen bond network with their neighbors in which the N—H groups in the backbone of one strand establish hydrogen bonds with the C=O groups in the backbone of the adjacent strands. In the fully extended α strand, successive side chains point straight up, then straight down, then straight up, etc. Adjacent β strands in a β sheet are aligned so that their $C^\alpha$ atoms are adjacent and their side chains point in the same direction. The "pleated" appearance of β strands arises from tetrahedral chemical bonding at the $C^\alpha$ atom; for example, if a side chain points straight up, then the bond to the $C^\nu$ must point slightly downwards, since its bond angle is approximately 109.5°. The pleating causes the distance between $C^\alpha_i$ and $C^\alpha_{i+2}$ be approximately 6 Å, rather than the 7.6 Å (2×3.8 Å) expected from two fully extended trans peptide virtual bonds. The "sideways" distance between adjacent $C^\alpha$ atoms in hydrogen-bonded β strands is roughly 5 Å.

Binding affinity: The strength of binding between a binding site and a ligand (for example, between an antibody, antigen binding Fc domain, antigen-binding CH3 domain and an antigen or epitope). The affinity of a binding site X for a ligand Y is represented by the dissociation constant ($K_d$), which is the concentration of Y that is required to occupy half of the binding sites of X present in a solution. A lower ($K_d$) indicates a stronger or higher-affinity interaction between X and Y and a lower concentration of ligand is needed to occupy the sites. In general, binding affinity can be affected by the alteration, modification and/or substitution of one or more amino acids in the epitope recognized by the paratope (portion of the molecule that recognizes the epitope). Binding affinity can be the affinity of antibody binding an antigen.

In one example, binding affinity is measured by end-point titration in an Ag-ELISA assay. Binding affinity is substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

CH2 or CH3 domain molecule: A polypeptide (or nucleic acid encoding a polypeptide) derived from an immunoglobulin CH2 or CH3 domain, such as from a monomeric Fc, see PCT application No. WO 2009/099961, incorporated herein by reference. The Fc domain can be from an IgG, IgA, IgD, IgE or IgM. In one embodiment described herein, the CH2 or CH3 domain molecule comprises at least one CDR, or functional fragment thereof. The CH2 or CH3 domain molecule can further comprise additional amino acid sequence, such as a complete hypervariable loop. In another embodiment, the CH2 or CH3 domain molecules have at least a portion of one or more beta strands replaced with a CDR, or functional fragment thereof. In some embodiments described herein, the CH2 or CH3 domains comprise one or more mutations in a loop region of the molecule. A "loop region" of a CH2 or CH3 domain refers to the portion of the protein located between regions of beta strands (for example, each CH2 domain comprises seven beta sheets, A to G, oriented from the N- to C-terminus), see the information provide below.

CH2 and CH3 domain molecules are small in size, usually less than 15 kD. The CH2 and CH3 domain molecules can vary in size depending on the length of CDR/hypervariable amino acid sequence inserted in the loops regions, how many CDRs are inserted and whether another molecule (such as an effector molecule or label) is conjugated to the CH2 or CH3 domain. In some embodiments, the CH2 or CH3 domain molecules do not comprise additional constant domains (i.e. CH1 or another CH2 or CH3 domain) or variable domains. In one embodiment, the CH2 domain is from IgG, IgA or IgD. In another embodiment, the constant domain is a CH3 domain from IgE or IgM, which is homologous to the CH2 domains of IgG, IgA or IgD.

CH2 and CH3 domain molecules can be glycosylated or unglycosylated. For example, a recombinant CH2 or CH3 domain can be expressed in an appropriate mammalian cell to allow glycosylation of the molecule.

Complementarity determining region (CDR): A short amino acid sequence found in the variable domains of antigen receptor (such as immunoglobulin and T cell receptor) proteins that provides the receptor with contact sites for antigen and its specificity for a particular antigen. Each polypeptide chain of an antigen receptor contains three CDRs (CDR1, CDR2 and CDR3). Antigen receptors are typically composed of two polypeptide chains (a heavy chain and a light chain), therefore there are six CDRs for each antigen receptor that can come into contact with the antigen. Since most sequence variation associated with antigen receptors are found in the CDRs, these regions are sometimes referred to as hypervariable domains.

CDRs are found within loop regions of an antigen receptor. These loop regions are typically referred to as hypervariable loops. Each antigen receptor comprises six hypervariable loops: H1, H2, H3, L1, L2 and L3. For example, the H1 loop comprises CDR1 of the heavy chain and the L3 loop comprises CDR3 of the light chain. The CH2 and CH3 domain molecules can include engrafted amino acids from a variable domain of an antibody. The engrafted amino acids comprise at least a portion of a CDR. The engrafted amino acids can also include additional amino acid sequence, such as a complete hypervariable loop. As used herein, a "functional fragment" of a CDR is at least a portion of a CDR that retains the capacity to bind a specific antigen.

Numbering conventions for the location of CDRs are known in the art. The amino acid sequence boundaries of a given CDR can be readily determined using any of a number of well-known schemes, including those described by Kabat et al., (1991) *Sequences of Proteins of Immunological Interest,* 5th Edition, U.S. Department of Health and Human Services, Public Health Service, National Institutes of Health, Bethesda, Md. (NIH Publication No. 91-3242; "Kabat" numbering scheme), Al-Lazikani et al., (JMB 273, 927-948, 1997; "Chothia" numbering scheme), and Lefranc, et al. ("IMGT unique numbering for immunoglobulin and T cell receptor variable domains and Ig superfamily V-like domains," Dev. Comp. Immunol., 27:55-77, 2003; "IMGT" numbering scheme).

Contacting: Placement in direct physical association, which includes both in solid and in liquid form.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor α (TNFα), interleukin-6 (IL-6), interleukin-10 (IL-10), interleukin-12 (IL-12), macrophage inflammatory protein 2 (MIP-2), KC, and interferon-γ (INF-γ).

Degenerate variant: As used herein, a "degenerate variant" of an Fc domain or a CH3 domain refers to a polynucleotide encoding the molecule that includes a sequence that is degenerate as a result of the genetic code. There are 20 natural amino acids, most of which are specified by more than one codon. Therefore, all degenerate nucleotide sequences are included as long as the amino acid sequence of the molecule encoded by the nucleotide sequence is unchanged.

Domain: A protein structure which retains its tertiary structure independently of the remainder of the protein. In some cases, domains have discrete functional properties and can be added, removed or transferred to another protein without a loss of function.

Effector molecule: A molecule, or the portion of a chimeric molecule, that is intended to have a desired effect on a cell to which the molecule or chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an Fc domain, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341-365, 1985. Diagnostic agents or moieties include radioisotopes and other detectable labels. Detectable labels useful for such purposes are also well known in the art, and include radioactive isotopes such as $^{32}$P, $^{125}$I, and $^{131}$I, fluorophores, chemiluminescent agents, and enzymes.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Expression: The translation of a nucleic acid into a protein. Proteins may be expressed and remain intracellular, become a component of the cell surface membrane, or be secreted into the extracellular matrix or medium Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Fc domain: The constant domain of an antibody. The wild-type Fc is homodimeric in nature and this feature is driven by the strong, high-affinity interaction that exists between the two CH3 domains. An antibody that includes a wild-type Fc domain has the ability to interact with neonatal Fc-receptor (FcRn) in a pH dependent manner; this interactin confers extended serum half-life. Although the wild-type "Fc" is a homodimer of polypeptides, the Fc domains disclosed herein are monomeric polypeptides which include a sequence of amino acids corresponding to the Fc portion of the heavy chain, such as containing a CH2 and CH3 domain, or containing a CH2 and CH3 domain that have amino acid substitutions such that they do not form homodimers. Monomeric Fc domains include IgG Fc, but can also be a monomeric Fc region of other immunoglobulin subclasses including IgA, IgE, IgD, and IgM. The CH2 and CH3 domains of any Fc can be identified using the International ImMunoGene Tics information system (IMGT), imgt_cines.fr/. The binding sites for C1q and FcγR are located in the CH2 domain of IgG. The glutamic acid, lysine, and lysine residues at positions 318, 320, and 322 (IMGT numbering), respectively, are a binding motif for C1q. In addition, amino acid residues at positions 234-238 are important in the high-affinity interaction of murine IgG2a with FcγRI.

With regard to the exemplary Fc domain shown in FIG. 1, the CH2 domain is amino acids 1-112 and the CH3 domain is amino acid 113-127 of SEQ ID NOs: 1-6. The FcRn binding surface is amino acids 21 to 27, 78 to 82, and 203 to 208. The CH3 dimerization surface is amino acids 117 to 121, 136 to 140, 164 to 169 and 175 to 179 of SEQ ID NOs: 1-6.

Fc domain molecule or Fc domain fusion: An Fc domain conjugated to an effector molecule. In some embodiments, an Fc domain molecule is a fusion protein. Similarly, a "CH3 domain molecule" is a CH3 domain conjugated to an effector molecule. In some embodiments, a CH3 domain molecule is a fusion protein. The fusion protein can include, for example, a VH, a engineered antibody domain, a diabody, an scFv, a cytokine, a toxin, an enzyme, and/or a ligand.

Framework region: Amino acid sequences interposed between CDRs (or hypervariable regions). Framework regions include variable light and variable heavy framework regions. Each variable domain comprises four framework regions, often referred to as FR1, FR2, FR3 and FR4. The framework regions serve to hold the CDRs in an appropriate orientation for antigen binding. Framework regions typically form b-sheet structures.

Fungal-associated antigen (FAAs): A fungal antigen which can stimulate fungal-specific T-cell-defined immune responses. Exemplary FAAs include, but are not limited to, an antigen from *Candida albicans, Cryptococcus* (such as d25, or the MP98 or MP88 mannoprotein from *C. neoformans*, or an immunological fragment thereof), *Blastomyces* (such as *B. dermatitidis*, for example WI-1 or an immunological fragment thereof), and *Histoplasma* (such as *H. capsulatum*).

Heterologous: A heterologous polypeptide or polynucleotide refers to a polypeptide or polynucleotide derived from a different source or species.

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunoconjugate: A covalent linkage of an effector molecule to an antibody Fc domain, or CH3 domain molecule. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as domain Ia of PE and the B chain of DT) and replacing it with a different targeting moiety, such as an Fc domain or CH3 domain. In one embodiment, an Fc domain is joined to an effector molecule (EM). In another embodiment, an Fc domain joined to an effector molecule is further joined to a lipid or other molecule to a protein or peptide to increase its half-life in the body. The linkage can be either by chemical or recombinant means. "Chemical means" refers to a reaction between the Fc domain (or the CH3 domain) and the effector molecule such that there is a covalent bond formed between the two molecules to form one molecule. A peptide linker (short peptide sequence) can optionally be included between the Fc (or CH3 domain) molecule and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand, antibody, Fc domain or CH3 domain molecule, conjugated (coupled) to an effector molecule.

The terms "conjugating," "joining," "bonding" or "linking" refer to making two polypeptides into one contiguous polypeptide molecule, or to covalently attaching a radionucleotide or other molecule to a polypeptide, such as an Fc domain or CH3 domain molecule. In the specific context, the terms include reference to joining a ligand, such as an antibody moiety, to an effector molecule ("EM").

Immunogen: A compound, composition, or substance which is capable, under appropriate conditions, of stimulating an immune response, such as the production of antibodies or a T-cell response in an animal, including compositions that are injected or absorbed into an animal.

Isolated: An "isolated" biological component (such as a nucleic acid molecule or protein) has been substantially separated or purified away from other biological components from which the component naturally occurs (for example, other biological components of a cell), such as other chromosomal and extra-chromosomal DNA and RNA and proteins, including other antibodies. Nucleic acids and proteins that have been "isolated" include nucleic acids and proteins purified by standard purification methods. An "isolated antibody" is an antibody that has been substantially separated or purified away from other proteins or biological components such that its antigen specificity is maintained. The term also embraces nucleic acids and proteins (including Fc domain, CH2 domain and CH3 domain molecules) prepared by recombinant expression in a host cell, as well as chemically synthesized nucleic acids or proteins, or fragments thereof.

Label: A detectable compound or composition that is conjugated directly or indirectly to another molecule, such as an antibody, Fc domain or CH2 or CH3 domain molecule, to facilitate detection of that molecule. Specific, non-limiting examples of labels include fluorescent tags, enzymatic linkages, and radioactive isotopes.

Ligand contact residue or Specificity Determining Residue (SDR): A residue within a CDR that is involved in contact with a ligand or antigen. A ligand contact residue is also known as a specificity determining residue (SDR). A non-ligand contact residue is a residue in a CDR that does not contact a ligand. A non-ligand contact residue can also be a framework residue.

Nanoantibody (nAb): A CH2 or CH3 domain molecule engineered such that the molecule specifically binds antigen and preserves partially or completely at least one Fc binding function, e.g., binding to the FcRn. The CH2 and CH3 domain molecules engineered to bind antigen are the smallest known antigen-specific binding human antibody domain-based molecules.

Neoplasia and Tumor: The product of neoplasia is a neoplasm (a tumor), which is an abnormal growth of tissue that results from excessive cell division. Neoplasias are also referred to as "cancer." A tumor that does not metastasize is referred to as "benign." A tumor that invades the surrounding tissue and/or can metastasize is referred to as "malignant."

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2'-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pathogen: A biological agent that causes disease or illness to its host. Pathogens include, for example, bacteria, viruses, fungi, protozoa and parasites. Pathogens are also referred to as infectious agents.

Examples of pathogenic viruses include those in the following virus families: Retroviridae (for example, human immunodeficiency virus (HIV); human T-cell leukemia viruses (HTLV); Picornaviridae (for example, polio virus, hepatitis A virus; hepatitis C virus; enteroviruses, human coxsackie viruses, rhinoviruses, echoviruses; foot-and-mouth disease virus); Calciviridae (such as strains that cause gastroenteritis); Togaviridae (for example, equine encephalitis viruses, rubella viruses); Flaviridae (for example, dengue viruses; yellow fever viruses; West Nile virus; St. Louis encephalitis virus; Japanese encephalitis virus; and other encephalitis viruses); Coronaviridae (for example, coronaviruses; severe acute respiratory syndrome (SARS) virus; Rhabdoviridae (for example, vesicular stomatitis viruses, rabies viruses); Filoviridae (for example, Ebola viruses); Paramyxoviridae (for example, parainfluenza viruses, mumps virus, measles virus, respiratory syncytial virus (RSV)); Orthomyxoviridae (for example, influenza viruses); Bunyaviridae (for example, Hantaan viruses; Sin Nombre virus, Rift Valley fever virus; bunya viruses, phleboviruses and Nairo viruses); Arena viridae (hemorrhagic fever viruses; Machupo virus; Junin virus); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses; BK-virus); Adenoviridae (most adenoviruses); Herpesviridae (herpes simplex virus (HSV)-1 and HSV-2; cytomegalovirus (CMV); Epstein-Barr virus (EBV); varicella zoster virus (VZV); and other herpes viruses, including HSV-6); Poxviridae (variola viruses, vaccinia viruses, pox viruses); and Iridoviridae (such as African swine fever virus); Filoviridae (for example, Ebola virus; Marburg virus); Caliciviridae (for example, Norwalk viruses) and unclassified viruses (for example, the etiological agents of Spongiform encephalopathies, the agent of delta hepatitis (thought to be a defective satellite of hepatitis B virus); and astroviruses).

Examples of fungal pathogens include, but are not limited to: *Cryptococcus neoformans*, *Histoplasma capsulatum*, *Coccidioides immitis*, *Blastomyces dermatitidis*, *Chlamydia trachomatis*, *Candida albicans*.

Examples of bacterial pathogens include, but are not limited to: *Helicobacter pyloris*, *Borelia burgdorferi*, *Legionella pneumophilia*, *Mycobacteria* sps (such as. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus influenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidum*, *Treponema pertenue*, *Leptospira*, and *Actinomyces israelli*.

Other pathogens (such as protists) include: *Plasmodium falciparum* and *Toxoplasma gondii*.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more antibodies, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

"Conservative" amino acid substitutions are those substitutions that do not substantially affect or decrease an activity or antigenicity of a polypeptide. For example, a polypeptide can include at most about 1, at most about 2, at most about 5, at most about 10, or at most about 15 conservative substitutions and specifically bind an antibody that binds the original polypeptide. The term conservative variation also includes the use of a substituted amino acid in place of an unsubstituted parent amino acid, provided that antibodies raised antibodies raised to the substituted polypeptide also immunoreact with the unsubstituted polypeptide. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |

| Original Residue | Conservative Substitutions |
| --- | --- |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, and/or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Probes and primers: A probe comprises an isolated nucleic acid attached to a detectable label or reporter molecule. Primers are short nucleic acids, and can be DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Purified: The term purified does not require absolute purity; rather, it is intended as a relative term. Thus, for example, a purified monomeric Fc or CH3 domain is one that is isolated in whole or in part from naturally associated proteins and other contaminants in which the molecule is purified to a measurable degree relative to its naturally occurring state, for example, relative to its purity within a cell extract or biological fluid.

The term "purified" includes such desired products as analogs or mimetics or other biologically active compounds wherein additional compounds or moieties are bound to the monomeric Fc or CH3 domain in order to allow for the attachment of other compounds and/or provide for formulations useful in therapeutic treatment or diagnostic procedures.

Generally, substantially purified monomeric Fc or CH3 domain molecules include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the monomeric Fc or CH3 domain molecule is purified to represent greater than 90%, often greater than 95% of all macromolecular species present in a purified preparation prior to admixture with other formulation ingredients. In other cases, the purified preparation may be essentially homogeneous, wherein other macromolecular species are less than 1%.

Recombinant: A recombinant nucleic acid or polypeptide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Sample: A portion, piece, or segment that is representative of a whole. This term encompasses any material, including for instance samples obtained from a subject.

A "biological sample" is a sample obtained from a subject including, but not limited to, cells, tissues and bodily fluids. Bodily fluids include, for example, saliva, sputum, spinal fluid, urine, blood and derivatives and fractions of blood, including serum and lymphocytes (such as B cells, T cells and subfractions thereof). Tissues include those from biopsies, autopsies and pathology specimens, as well as biopsied or surgically removed tissue, including tissues that are, for example, unfixed, frozen, fixed in formalin and/or embedded in paraffin.

In particular embodiments, the biological sample is obtained from a subject, such as blood or serum. A biological sample is typically obtained from a mammal, such as a rat, mouse, cow, dog, guinea pig, rabbit, or primate. In one embodiment, the primate is macaque, chimpanzee, or a human.

Scaffold: As used herein, a monomeric Fc or CH3 domain scaffold is a recombinant monomeric Fc or CH3 domain that can be used as a platform to introduce mutations (such as in the beta strands) or CDRs (such as in the beta strands or loop regions) in order to confer antigen binding to the monomeric Fc or CH3 domain. In some embodiments, the scaffold is altered to exhibit increased stability compared with the native Fc or CH3 domain. In particular examples, the scaffold is mutated to introduce pairs of cysteine residues to allow formation of one or more non-native disulfide bonds.

Sequence identity: The similarity between nucleotide or amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990.) is available from several sources, including the National Center for Biotechnology Information (NCBI, Bethesda, Md.) and on the Internet, for use in connection with the sequence analysis programs blastp, blastn, blastx, tblastn and tblastx.

Specific binding agent: An agent that binds substantially only to a defined target. Thus an antigen specific binding agent is an agent that binds substantially to an antigenic polypeptide or antigenic fragment thereof. In one embodiment, the specific binding agent is a monoclonal antibody, a polyclonal antibody, a monomeric Fc domain, or CH3 domain (such as a fusion polypeptide) fusion, such with an antibody, that specifically binds the antigenic polypeptide or antigenic fragment thereof. In another embodiment, the specific binding agent is a ligand, monomeric Fc domain-ligand fusion or CH3 domain-ligand fusion that specifically binds a receptor.

The term "specifically binds" refers, with respect to an antigen, to the preferential association of an antibody or other ligand, in whole or part, with a cell or tissue bearing that antigen and not to cells or tissues lacking a detectable amount of that antigen. It is, of course, recognized that a certain degree of non-specific interaction may occur between a molecule and a non-target cell or tissue. Nevertheless, specific binding may be distinguished as mediated through specific recognition of the antigen. Specific binding results in a much stronger association between the antibody, monomeric Fc domain or CH3 domain fusion protein, and cells bearing the antigen (or receptor) than between the bound antibody, monomeric Fc domain or CH3 domain molecule and cells lacking the antigen (or receptor). Specific binding typically results in greater than 2-fold, such as greater than 5-fold, greater than 10-fold, or greater than 100-fold increase in amount of bound antibody, monomeric Fc domain fusion protein, CH3 domain fusion protein (per unit time) to a cell or tissue bearing the antigenic polypeptide (or receptor) as compared to a cell or tissue lacking the antigenic polypeptide respectively. Specific binding to a protein under such conditions requires a molecule that is selected for its specificity for a particular protein. A variety of immunoassay formats are appropriate for selecting antibodies, Fc domain and/or CH3 domain, such as fusion proteins, that are specifically immunoreactive with a particular protein. For example, solid-phase ELISA immunoassays are routinely used.

Subject: Living multi-cellular organisms, including vertebrate organisms, a category that includes both human and non-human mammals.

Therapeutically effective amount: A quantity of a specified agent sufficient to achieve a desired effect in a subject being treated with that agent. Such agents include the monomeric Fc domain molecules described herein. In one non-limiting example, this may be the amount of an HIV-specific monomeric Fc domain (or HIV-specific CH3 domain molecule) useful in preventing, treating or ameliorating infection by HIV. Ideally, a therapeutically effective amount of an antibody is an amount sufficient to prevent, treat or ameliorate infection or disease, such as is caused by HIV infection in a subject without causing a substantial cytotoxic effect in the subject. The therapeutically effective amount of an agent useful for preventing, ameliorating, and/or treating a subject will be dependent on the subject being treated, the type and severity of the affliction, and the manner of administration of the therapeutic composition.

Toxin: A molecule that is cytotoxic for a cell. Toxins include, but are not limited to, abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (for example, domain Ia of PE or the B chain of DT) and replacing it with a different targeting moiety, such as a monomeric Fc, CH2 or CH3 domain molecule.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Tumor-associated antigens (TAAs): A tumor antigen which can stimulate tumor-specific T-cell-defined immune responses. Exemplary TAAs include, but are not limited to, RAGE-1, tyrosinase, MAGE-1, MAGE-2, NY-ESO-1, Melan-A/MART-1, glycoprotein (gp) 75, gp100, beta-catenin, PRAME, MUM-1, WT-1, CEA, and PR-1. Additional TAAs are known in the art (for example see Novellino et al., *Cancer Immunol. Immunother.* 54(3):187-207, 2005) and includes TAAs not yet identified.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Viral-associated antigen (VAAs): A viral antigen which can stimulate viral-specific T-cell-defined immune responses. Exemplary VAAs include, but are not limited to, an antigen from human immunodeficiency virus (HIV), BK virus, JC virus, Epstein-Barr virus (EBV), cytomegalovirus (CMV), adenovirus, respiratory syncytial virus (RSV), herpes simplex virus 6 (HSV-6), parainfluenza 3, or influenza B.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Overview

Conventional antibodies are large multi-subunit protein complexes comprising at least four polypeptide chains, including two light chains and two heavy chains (see FIG. 6A for schematic drawings). The heavy and light chains of antibodies contain variable regions, which bind antigen, and constant regions (such as CH1, CH2 and CH3 domains), which provide structural support and effector functions. The antigen binding region comprises two separate domains, a heavy chain variable domain ($V_H$) and a light chain variable domain ($V_L$). A typical antibody, such as an IgG molecule, has a molecular weight of approximately 150 kD. A number of smaller antigen binding fragments of naturally occurring antibodies have been identified following protease digestion (for example, Fab, Fab', and F(ab')$_2$). These antibody fragments have a molecular weight ranging from approximately 50 to 100 kD. Recombinant methods have been used to generate alternative antigen-binding fragments, termed single chain variable fragments (scFv), which consist of $V_L$ and $V_H$ joined by a synthetic peptide linker. A scFv molecule has a molecular weight of approximately 25-30 kD.

However, in some cases, therapeutic use of antibodies or antibody fragments can be limited due to the size of the antibody. For example, if an antibody or antibody fragment is too large, tissue penetration and epitope access may be restricted. In addition, many therapeutic antibodies are of non-human origin, which can result in toxicity in a human subject. Given these limitations, small, antibodies that can specifically bind antigen are desirable for diagnostic or therapeutic applications that utilize antibodies or their fragments.

Generally, monomeric Fc domains include a both CH2 and a CH3 domain, are small, stable, soluble, have minimal to no toxicity and in some cases, are capable of binding antigen. The monomeric Fc domains bind neonatal Fc (FcRn) and thus are stable. In solution, the monomeric Fc domains are greater than about 99% monomeric. In some embodiments, the monomeric Fc domains include an amino acid substitution at position L121, T136, L138, and P165, with reference to SEQ ID NO: 2 (wild-type Fc). Isolated CH3 domains from these monomeric Fc domains are also disclosed herein.

Antigen-binding monomeric Fc domain and CH3 domains are also disclosed herein that specifically bind an antigen of interest. Libraries of these molecules are disclosed. These libraries can be screened to identify an antigen-binding Fc domain, or an antigen binding CH3 domain of interest.

Monomeric Fc domain molecules, that include a monomeric Fc domain and an effector molecule, are provided. Monomeric CH3 domain molecules, that include a monomeric CH3 domain and an effector molecule, are provided. The effector molecule can include one or more of a variable domain, a cytokine, a label and a toxin. The effector molecule can be ligated to the Fc domain or the CH3 domain at the N- or the C-terminus.

Nucleic acids are provided that encode these monomeric Fc domains, CH3 domains, antigen binding Fc domains, antigen binding CH3 domains, Fc molecules, and CH3 molecules. Expression vectors including these nucleic acids, and host cells transformed with these expression vectors, are also disclosed. Methods of using these Fc domains, CH3 domains and fusion proteins are also provided.

Generally, the monomeric Fc domain molecules and CH3 domain molecules are of use in any method wherein antibodies can be used. Thus these monomeric Fc domain molecules and CH3 domain molecules can be used for the treatment of a variety of diseases and disorders, including infections with a pathogen, autoimmune diseases and cancer. The monomeric Fc domain molecules and CH3 domain molecules also can be used for diagnosis.

Monomeric Fc Domains and CH3 Domains

Wild-type Fc is a homodimer that binds the neonatal Fc receptor. The monomeric Fc domains disclosed herein are at least 99% monomeric and include a CH2 and a CH3 domain. These monomeric Fc domains bind the neonatal Fc receptor (FcRn). The monomerc Fc can be an IgG Fc, such as an $IgG_1$, $IgG_2$, $IgG_3$ or $IgG_4$ Fc domain. However, in other embodiments, the monomeric Fc is an IgA, IgM, or IgD Fc domain.

Generally, a monomeric Fc domain comprises a substitution of at least one of the amino acids at the following positions: L121, T136, L138 and P165, with reference to the amino acid position in wild type Fc, see FIG. 1D and SEQ ID NO: 2. The monomeric Fc domain can also include an amino acid substitution at position 175, position 177 and/or position 179. In some embodiments, a monomeric Fc includes an amino acid substitution at L121, T136, L138 and P165. In additional embodiments, monomeric Fc domain can also include an amino acid substitution at position 175, position 177 and position 179.

The monomeric Fc domain can include, or consist of, the amino acid sequence set forth as SEQ ID NO: 1 (see FIG. 1), wherein X1 is Y, K or S, wherein X2 is Y, S or R, wherein X3 is A, L or H, wherein X4 is R, V or K. The monomeric Fc domain does not include the amino acid sequence set forth as SEQ ID NO: 2, as this is wild-type Fc, which is dimeric. The monomeric Fc domain is at least 99% monodimeric and binds the neonatal Fc receptor (FcRn).

Figure 1C:
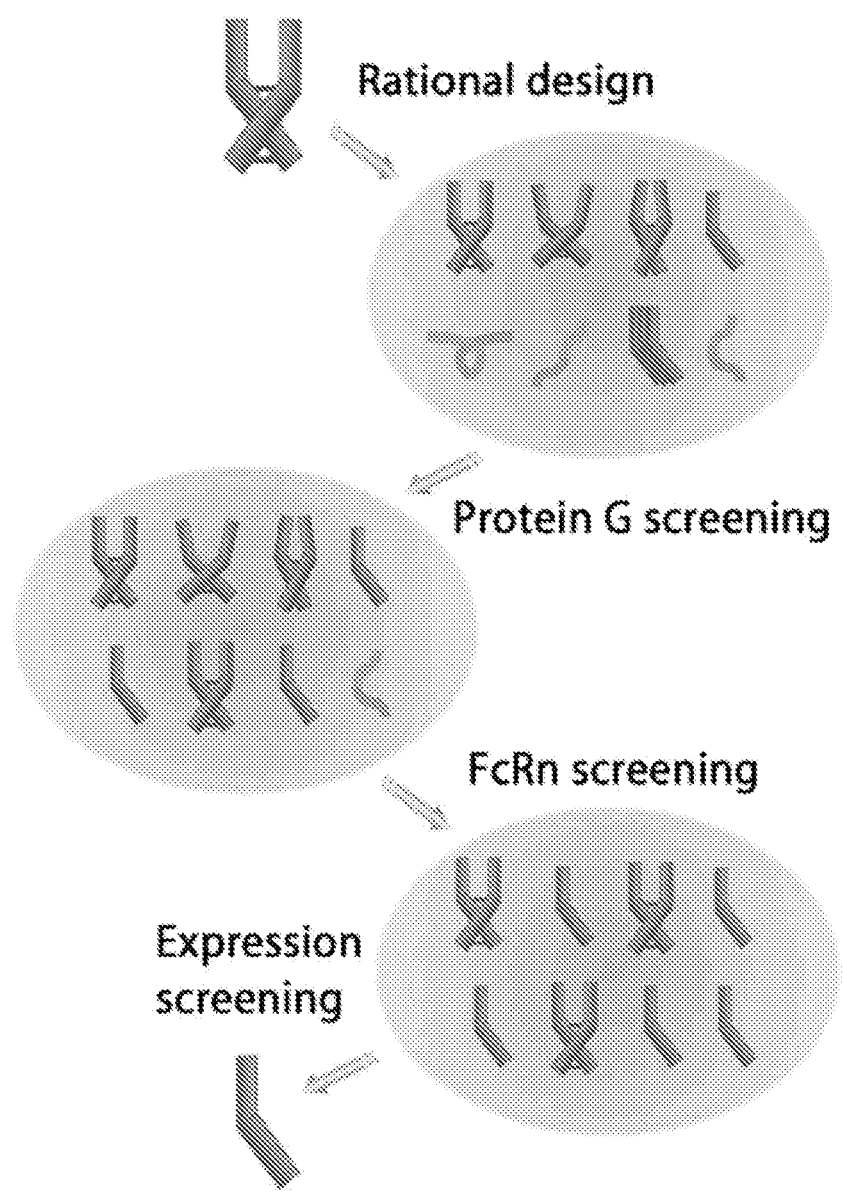
FIG. 1C Schematic of the multiple screening strategies.
Figure 1D:
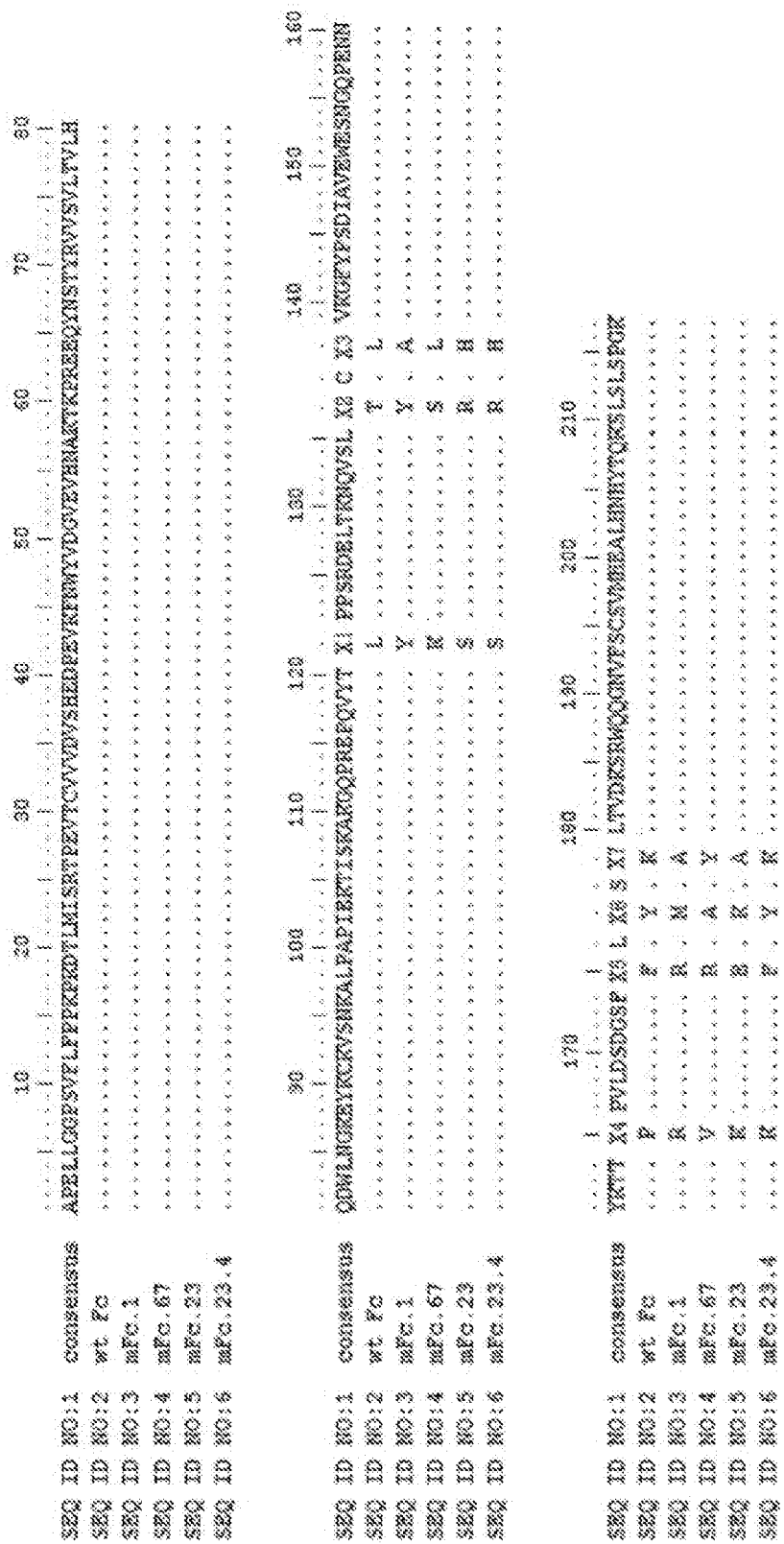
FIG. 1D Amino acid sequence alignment, showing the consensus sequence for the monomeric Fc domains disclosed herein. The consensus sequence is SEQ ID NO: 1 (see FIG. 1), wherein X1 is Y, K or S, wherein X2 is Y, S or R, wherein X3 is A, L or H, wherein X4 is R, V or K, wherein X5 is F, R or E; wherein X6 is Y, M, A, K; and wherein X7 is K, A or Y. Also shown are the amino acid sequence of wild-type Fc (SEQ ID NO: 2), of mFc.1 (SEQ ID NO: 3), mFc. 67 (SEQ ID NO: 4), mFc.23 (SEQ ID NO: 5), mFc.23.4 (SEQ ID NO: 6). The numbering begins with the IgG1 Fc, thus residues 121, 136, 138, 165, 175, 177, 179 correspond to residues 351, 366, 368, 395, 405, 407 and 409 in $IgG_1$ numbering system, respectively.

The monomeric Fc domain can include, or consist of, the amino acid sequence set forth in SEQ ID NO: 1, wherein X1 is Y, K or S, wherein X2 is Y, S or R, wherein X3 is A, L or H, wherein X4 is R, V or K, and wherein X5 is F, X6 is Y and X7 is K. The monomeric Fc domain can include, or consist of, the amino acid sequence set forth in SEQ ID NO: 1, wherein X1 is Y, K or S, wherein X2 is Y, S or R, wherein X3 is A, L or H, wherein X4 is R, V or K, and wherein X5 is R or E, X6 is M, A or K, and wherein X7 is A or Y. The monomeric Fc domain can include, or consist of, the amino acid sequence set forth in SEQ ID NO: 1, wherein X1 is Y, K or S, wherein X2 is Y, S or R, wherein X3 is A, L or H, wherein X4 is R, V or K, and wherein X5 is F, X6 is Y, and/or wherein X7 is K. In other embodiments, The monomeric Fc domain can include, or consist of, the amino acid sequence set forth in SEQ ID NO: 1, wherein X1 is Y, K or S, wherein X2 is Y, S or R, wherein X3 is A, L or H, wherein X4 is R, V or K, and wherein X5 is F, X6 is Y, and wherein X7 is K. These specific amino acid substitutions can be utilized in any combination, although exemplary combinations at X1-X7 of use are shown in FIG. 1D.

In some embodiments, the monomeric Fc domain includes, or consists of SEQ ID NO: 1, wherein X1 is Y, X2 is Y, X3 is A and X4 is R. Thus, in some non-limiting examples, the monomeric Fc domain includes, or consists of SEQ ID NO: 1, wherein X1 is Y, X2 is Y, X3 is A, X4 is R, and X5 is F, R or E; X6 is Y, M, A, K and X7 is X, A or Y.

In other examples, the monomeric Fc domain includes, or consists of SEQ ID NO: 1, wherein X1 is Y, X2 is Y, X3 is A and X4 is R, X5 is F; X6 is Y and X7 is K. In another example, the monomeric Fc domain includes, or consists of SEQ ID NO: 1, wherein X1 is Y, X2 is Y, X3 is A and X4 is R, X5 is R; X6 is M and X7 is A (SEQ ID NO: 3, mFc.1).

In additional embodiments, the monomeric Fc domain includes, or consists of SEQ ID NO: 1, wherein X1 is K, X2 is S, X3 is L and X4 is V. Thus, in additional non-limiting examples, the monomeric Fc domain includes, or consists of SEQ ID NO: 1, wherein X1 is K, X2 is S, X3 is L, X4 is V and X5 is F, R or E; X6 is Y, M, A, K and X7 is X, A or Y. In other examples, the monomeric Fc domain includes, or consists of SEQ ID NO: 1, wherein X1 is K, X2 is S, X3 is L, X4 is V, X5 is F; X6 is Y and X7 is K. In another example, the monomeric Fc domain includes, or consists of SEQ ID NO: 1, wherein X1 is K, X2 is S, X3 is L, X4 is V, X5 is R, X6 is A, and X7 is Y (SEQ ID NO: 4, m.Fc.67).

If further embodiments, the monomeric Fc domain includes, or consists of SEQ ID NO: 1, wherein X1 is S, X2 is R, X3 is H and X4 is K. Thus, in additional non-limiting examples, X1 is S, X2 is R, X3 is H and X4 is K and X5 is F, R or E; X6 is Y, M, A, K and X7 is K, A or Y. In other examples, X1 is S, X2 is R, X3 is H and X4 is K, X5 is F; X6 is Y and X7 is K (SEQ ID NO: 6, mFc.23.4). In another example, X1 is S, X2 is R, X3 is H and X4 is K, X5 is E, X6 is K and X7 is A (SEQ ID NO: 5, mFc.23).

The monomeric Fc can include additional mutations. In some embodiments, the monomeric Fc can include two cysteine residues introduced into the CH2 domain. Exemplary substitutions are at positions 242 and 334. In additional embodiments, the monomeric Fc can include two cysteine residues introduced into the CH3 domain. Exemplary substitutions are at positions 343 and 431. In further embodiments, the monomeric Fc can include four cysteine residues, two in the CH2 domain and two in the CH3 domain. Exemplary substitutions are at positions 242, 334, 343 and 431 using IMGT numbering. The monomeric Fc can include, or consist of SEQ ID NO: 44.

In some embodiments, the monomeric Fc domain includes, or consists of, SEQ ID NO: 44: APELLGGPS-VFCFPPKPKDTLMISRTPEVTCVVVDVSHEDPEVKF-NWYVDGVEVHNAKTK PREEQYNSTYRVVSVLTVL-HQDWLNGKEYKCKVSNKALPAPIECTISKAKGQCR-EPQVYTX1PPSRDELTKNQVSLX2CX3VKGFYPSDIA-VEWESNGQPENNYKTTX4PVLDSDGSFX5LX6SX7LT-VDKSRWQQGNVFSCSVMHEULHNHYTQKSLSLSP-GK (SEQ ID NO: 44), wherein X1 is Y, K or S, wherein X2 is Y, S or R, wherein X3 is A, L or H, wherein X4 is R, V or K. In some embodiments, X6 is F, S6 is Y and X7 is K. This sequence includes the 242C/334C/343C/431C mutations (using IMGT numbering).

In some embodiments, the monomeric Fc domain is at least 99% monodimeric and binds the neonatal Fc receptor (FcRn). In other embodiments, the monomeric Fc has a melting temperature (Tm) of about 70° C. or greater, such as about 70, about 71, about 72, about 73, about 75, about 76, about 77, about 78, about 79, or about 80° C. In other embodiments, the Tm is about 70 to about 72° C., or about 70 to about 75° C. In this context, about indicates within 0.2° C.

The monomeric Fc domain can include, or consist of, the amino acid sequence set forth in SEQ ID NO: 44, wherein X1 is Y, K or S, wherein X2 is Y, S or R, wherein X3 is A, L or H, wherein X4 is R, V or K, and wherein X5 is F, X6 is Y and X7 is K. The monomeric Fc domain can include, or consist of, the amino acid sequence set forth in SEQ ID NO: 44, wherein X1 is Y, K or S, wherein X2 is Y, S or R, wherein X3 is A, L or H, wherein X4 is R, V or K, and wherein X5 is R or E, X6 is M, A or K, and wherein X7 is A or Y. The monomeric Fc domain can include, or consist of, the amino acid sequence set forth in SEQ ID NO: 44, wherein X1 is Y, K or S, wherein X2 is Y, S or R, wherein X3 is A, L or H, wherein X4 is R, V or K, and wherein X5 is F, X6 is Y, and/or wherein X7 is K. In other embodiments, The monomeric Fc domain can include, or consist of, the amino acid sequence set forth in SEQ ID NO: 44, wherein X1 is Y, K or S, wherein X2 is Y, S or R, wherein X3 is A, L or H, wherein X4 is R, V or K, and wherein X5 is F, X6 is Y, and wherein X7 is K. These specific amino acid substitutions can be utilized in any combination, although exemplary combinations at X1-X7 of use are shown in FIG. 1D. In these embodiments, the Fc also includes the 242C/334C/343C/431C mutations.

In some embodiments, the monomeric Fc domain includes, or consists of SEQ ID NO: 44, wherein X1 is Y, X2 is Y, X3 is A and X4 is R. Thus, in some non-limiting examples, the monomeric Fc domain includes, or consists of SEQ ID NO: 44, wherein X1 is Y, X2 is Y, X3 is A, X4 is R, and X5 is F, R or E; X6 is Y, M, A, K and X7 is X, A or Y. In other examples, the monomeric Fc domain includes, or consists of SEQ ID NO: 44, wherein X1 is Y, X2 is Y, X3 is A and X4 is R, X5 is F; X6 is Y and X7 is K. In another example, the monomeric Fc domain includes, or consists of SEQ ID NO: 44, wherein X1 is Y, X2 is Y, X3 is A and X4 is R, X5 is R; X6 is M and X7 is A (mFc.1 242C/334C/343C/431C, SEQ ID NO: 45).

In additional embodiments, the monomeric Fc domain includes, or consists of SEQ ID NO: 44, wherein X1 is K, X2 is S, X3 is L and X4 is V. Thus, in additional non-limiting examples, the monomeric Fc domain includes, or consists of SEQ ID NO: 44, wherein X1 is K, X2 is S, X3 is L, X4 is V and X5 is F, R or E; X6 is Y, M, A, K and X7 is X, A or Y. In other examples, the monomeric Fc domain includes, or consists of SEQ ID NO: 44, wherein X1 is K, X2 is S, X3 is L, X4 is V, X5 is F; X6 is Y and X7 is K. In another example, the monomeric Fc domain includes, or consists of SEQ ID NO: 44, wherein X1 is K, X2 is S, X3 is L, X4 is V, X5 is R, X6 is A, and X7 is Y (m.Fc.67 242C/334C/343C/431C, SEQ ID NO: 46).

If further embodiments, the monomeric Fc domain includes, or consists of SEQ ID NO: 44, wherein X1 is S, X2 is R, X3 is H and X4 is K. Thus, in additional non-limiting examples, X1 is S, X2 is R, X3 is H and X4 is K and X5 is F, R or E; X6 is Y, M, A, K and X7 is K, A or Y. In other examples, X1 is S, X2 is R, X3 is H and X4 is K, X5 is F; X6 is Y and X7 is K (mFc.23.4 242C/334C/343C/431C, SEQ ID NO: 47). In another example, X1 is S, X2 is R, X3 is H and X4 is K, X5 is E, X6 is K and X7 is A (mFc.23242C/334C/343C/431C, SEQ ID NO: 48).

In further embodiments, the monomeric Fc is at least 95%, at least 96%, at least 97%, at least 98%, or at least 99% identical to SEQ ID NO: 1, SEQ ID NO: 3, SEQ ID NO: 4, SEQ ID NO: 5, SEQ ID NO: 6, SEQ ID NO: 44, SEQ ID NO: 45, SEQ ID NO: 46, SEQ ID NO: 47 and/or SEQ ID NO: 48, but is not, and does not include, the amino acid sequence set forth as SEQ ID NO: 2.

An isolated CH3 domain is also provided. With regard to an isolated Fc domain, the CH3 domain is generally amino acids 113-127 of the Fc domain (see, for Example, SEQ ID NOs: 1-6). Thus, with regard to an Fc domain, isolated CH3 domains are provided herein that include amino acids 113 to 127 of any of the monomeric Fc molecules disclosed herein (see, for example, FIG. 1D, SEQ ID NO: 1, SEQ ID NO: 3, SEQ ID NO: 4, SEQ ID NO: 5, SEQ ID NO: 6, SEQ ID NO: 44, SEQ ID NO: 45, SEQ ID NO: 46, SEQ ID NO: 47 and/or SEQ ID NO: 48). In specific, non-limiting examples, isolated CH3 domains are provided herein that include amino acids 113-127 of any one of SEQ ID NO: 1, SEQ ID NO: 3, SEQ ID NO: 4, SEQ ID NO: 5, SEQ ID NO: 6, SEQ ID NO: 44, SEQ ID NO: 45, SEQ ID NO: 46, SEQ ID NO: 47 and/or SEQ ID NO: 48. These isolated CH3 domains can be fused to another protein and/or conjugated to an effector molecule to produce a CH3 domain molecule.

The presently disclosed monomeric Fc domains and CH3 domains can be included in fusion proteins, such as with an effector molecule. Thus, these Fc domains and CH domains can be used to produce a variety of monomeric Fc domain molecules or CH3 domain molecules, respectively, that include an effector molecule. Generally a "monomeric Fc domain molecule" includes both a monomeric Fc domain and a heterologous protein, such as an effective molecule. Similarly, a "monomeric CH3 domain molecule" includes both a monomeric CH3 domain and a heterologous protein, such as an effective molecule. These molecules bind the neonatal Fc receptor (FcRn) and are monomeric.

In one embodiment, the effector molecule is a $V_H$ domain, diabody, engineered antibody domain, or an scFv of an antibody that specifically binds any antigen of interest. The $V_H$ domain, diabody, engineered antibody domain, or an scFv can be fused to the N or the C terminus of the monomeric Fc domain or the monomeric CH3 domain. Exemplary molecules are shown in FIG. 6A. The antigen bound by the $V_H$ domain, diabody, engineered antibody domain, or an scFv can be an antigen that is specific to a cancer, infectious disease (such as viral, bacterial, fungal or parasitic infections), autoimmune disease, inflammatory disorders, or any other disease or condition for which antibodies or their fragments can be used as therapeutic agents.

In some embodiments, the antigen is an antigen from a virus, such as a virus from one of the following families: Retroviridae (for example, human immunodeficiency virus (HIV); human T-cell leukemia viruses (HTLV); Picornaviridae (for example, polio virus, hepatitis A virus; hepatitis C virus; enteroviruses, human coxsackie viruses, rhinoviruses, echoviruses; foot-and-mouth disease virus); Calciviridae (such as strains that cause gastroenteritis); Togaviridae (for example, equine encephalitis viruses, rubella viruses); Flaviridae (for example, dengue viruses; yellow fever viruses; West Nile virus; St. Louis encephalitis virus; Japanese encephalitis virus; and other encephalitis viruses); Coronaviridae (for example, coronaviruses; severe acute respiratory syndrome (SARS) virus; Rhabdoviridae (for example, vesicular stomatitis viruses, rabies viruses); Filoviridae (for example, Ebola viruses); Paramyxoviridae (for example, parainfluenza viruses, mumps virus, measles virus, respiratory syncytial virus (RSV)); Orthomyxoviridae (for example, influenza viruses); Bunyaviridae (for example, Hantaan viruses; Sin Nombre virus, Rift Valley fever virus; bunya viruses, phleboviruses and Nairo viruses); Arenaviridae (hemorrhagic fever viruses; Machupo virus; Junin virus); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses; BK-virus); Adenoviridae (most adenoviruses); Herpesviridae (herpes simplex virus (HSV)-1 and HSV-2; cytomegalovirus (CMV); Epstein-Barr virus (EBV); varicella zoster virus (VZV); and other herpes viruses, including HSV-6); Poxviridae (variola viruses, vaccinia viruses, pox viruses); and Iridoviridae (such as African swine fever virus); Filoviridae (for example, Ebola virus; Marburg virus); Caliciviridae (for example, Norwalk viruses) and unclassified viruses (for example, the etiological agents of Spongiform encephalopathies, the agent of delta hepatitis (thought to be a defective satellite of hepatitis B virus); and astroviruses).

In other embodiments, the antigen is from a bacterium, such as *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, or *Actinomyces israelli*.

In other embodiments, the antigen is an antigen from a fungus, such as *Cryptococcus neoformans, Histoplasma capsulatum, Coccidioides immitis, Blastomyces dermatitidis, Chlamydia trachomatis*, or *Candida albicans*. In other embodiments, the infectious disease is caused by a parasite, such as *Plasmodium falciparum* or *Toxoplasma gondii*.

In some embodiments, the antigen is a cancer antigen, such as a solid tumor or a hematogenous cancer antigen. In particular examples, the solid tumor is a sarcoma or a carcinoma, such as fibrosarcoma, myxosarcoma, liposarcoma, chondrosarcoma, osteogenic sarcoma, or another sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, or a CNS tumor (such as a glioma, astrocytoma, medulloblastoma, craniopharyogioma, ependymoma, pinealoma, hemangioblastoma, acoustic neuroma, oligodendroglioma, menangioma, melanoma, neuroblastoma or retinoblastoma).

In some examples, the hematogenous cancer is a leukemia, such as an acute leukemia (such as acute lymphocytic leukemia, acute myelocytic leukemia, acute myelogenous leukemia and myeloblastic, promyelocytic, myelomonocytic, monocytic and erythroleukemia); a chronic leukemia (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia or myelodysplasia.

Tumor antigens are well known in the art and include, for example, carcinoembryonic antigen (CEA), β-human chorionic gonadotropin (β-HCG), alpha-fetoprotein (AFP), lectin-reactive AFP, (AFP-L3), thyroglobulin, RAGE-1, MN-CA IX, human telomerase reverse transcriptase (hTERT), RU1, RU2 (AS), intestinal carboxyl esterase, mut hsp70-2, M-CSF, prostase, prostate-specific antigen (PSA), PAP, NY- ESO-1, LAGE-1a, p53, prostein, PSMA, Her2/neu, survivin and telomerase, prostate-carcinoma tumor antigen-1 (PCTA-1), melanoma-associated antigen (MAGE), ELF2M, neutrophil elastase, ephrinB2 and CD22. The CH2 or CH3 domain molecules can also bind any cancer-related proteins, such IGF-I, IGF-II, IGR-IR or mesothelin. Additional tumor associated antigens are provided below in Table 1.

TABLE 3

Exemplary tumors and their tumor antigens

| Tumor | Tumor Associated Target Antigens |
|---|---|
| Acute myelogenous leukemia | Wilms tumor 1 (WT1), preferentially expressed antigen of melanoma (PRAME), PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | New York esophageous 1 (NY-Eso1) |
| Malignant melanoma | MAGE, MART, Tyrosinase, PRAME GP100 |
| Breast cancer | WT1, herceptin |
| Lung cancer | WT1 |
| Prostate cancer | Prostate-specific antigen (PSA) |
| Colon cancer | Carcinoembryonic antigen (CEA) |
| Renal cell carcinoma (RCC) | Fibroblast growth factor 5 (FGF-5) |

In some embodiments, antigen is associated with an autoimmune disease, such as rheumatoid arthritis, juvenile oligoarthritis, collagen-induced arthritis, adjuvant-induced arthritis, Sjögren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia or pernicious anemia.

In further embodiments, a monomeric Fc domain molecule or a monomeric CH3 domain molecule includes a toxin. Optionally, the monomeric Fc domain molecule or the monomeric CH3 domain molecule can also include a heavy chain variable domain, a diabody, and engineered antibody domain, and/or a scFv in addition to the toxin. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.).

Diphtheria toxin is isolated from *Corynebacterium diphtheriae*. Typically, diphtheria toxin for use in immunotoxins is mutated to reduce or to eliminate non-specific toxicity. A mutant known as CRM 107, which has full enzymatic activity but markedly reduced non-specific toxicity, has been known since the 1970's (Laird and Groman, *J. Virol.* 19:220, 1976), and has been used in human clinical trials. See, U.S. Pat. No. 5,792,458 and U.S. Pat. No. 5,208,021. As used herein, the term "diphtheria toxin" refers as appropriate to native diphtheria toxin or to diphtheria toxin that retains enzymatic activity but which has been modified to reduce non-specific toxicity.

Ricin is the lectin RCA60 from *Ricinus communis* (Castor bean). The term "ricin" also references toxic variants thereof. For example, see, U.S. Pat. No. 5,079,163 and U.S. Pat. No. 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Ribonucleases have also been conjugated to targeting molecules for use as immunotoxins (see Suzuki et al., *Nat. Biotech.* 17:265-70, 1999). Exemplary ribotoxins such as α-sarcin and restrictocin are discussed in, for example, Rathore et al., *Gene* 190:31-5, 1997; and Goyal and Batra, *Biochem* 345 Pt 2:247-54, 2000. Calicheamicins were first isolated from *Micromonospora echinospora* and are members of the enediyne antitumor antibiotic family that cause double strand breaks in DNA that lead to apoptosis (see, e.g., Lee et al., *J. Antibiot* 42:1070-87. 1989). The drug is the toxic moiety of an immunotoxin in clinical trials (see, for example, Gillespie et al., *Ann Oncol* 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., *Agr. Biol. Chem.* 52:1095, 1988; and Olsnes, Methods Enzymol. 50:330-335, 1978).

The monomeric Fc domain or CH3 domain molecule can include a cytokine. Cytokines include, but are not limited to, tumor necrosis factor α (TNFα), interleukin-6 (IL-6), interleukin-10 (IL-10), interleukin-12 (IL-12), macrophage inflammatory protein 2 (MIP-2), KC, and interferon-γ (INF-γ).

The monomeric Fc domains and CH3 domain disclosed herein are of use for extending half-life of any protein of interest. Thus, the monomeric Fc domain molecules and CH3 domain molecules can include any heterologous polypeptide. Suitable proteins include labels, receptors, growth factors, ligands, enzymes, erythropoietin, chemokines, therapeutic proteins and hormones. In some non-limiting examples, the heterologous protein is a human interferon, erythropoietin (EPO), soluble tumor necrosis factor receptor, CTLA-4, soluble interleukin (IL)-4 receptor, or Factor IX.

A peptide linker (short peptide sequence) can optionally be included between the monomeric Fc domain or the CH3 domain and any effector molecule. Suitable peptide linkers are known in the art, and include, for example, glysine and serine residues.

Monomeric Fc domains and CH3 domains can be conjugated to other compounds including, but not limited to, enzymes, paramagnetic beads, colloidal paramagnetic beads, haptens, fluorochromes, metal compounds, radioactive compounds or drugs. The enzymes that can be conjugated to the monomeric Fc domain or CH3 domain include, but are not limited to, alkaline phosphatase, peroxidase, urease and β-galactosidase. The fluorochromes that can be conjugated to the monomeric Fc domain or CH3 domain include, but are not limited to, fluorescein isothiocyanate, tetramethylrhodamine isothiocyanate, phycoerythrin, allophycocyanins and Texas Red. For additional fluorochromes that can be conjugated to the monomeric Fc domain, CH3 domain or fusion protein see Haugland, R. P., *Molecular Probes: Handbook of Fluorescent Probes and Research Chemicals* (1992-1994). The metal compounds that can be conjugated to the monomeric Fc domain or CH3 domain include, but are not limited to, ferritin, colloidal gold, and particularly, colloidal superparamagnetic beads. The haptens that can be conjugated to the monomeric Fc domain or CH3 domain but are not limited to, biotin, digoxigenin, oxazalone, and nitrophenol. Additional reagents are well known in the art. In view of the large number of methods that have been reported for attaching a variety of radiodiagnostic compounds, radiotherapeutic compounds, label (for example, enzymes or fluorescent molecules) drugs, toxins, and other agents to antibodies, one skilled in the art will be able to determine a suitable method for covalently attaching a given agent.

The procedure for attaching an effector molecule to a protein varies according to the chemical structure of the effector. Polypeptides typically contain a variety of functional groups; for example, carboxylic acid (COOH), free amine (—NH$_2$) or sulfhydryl (—SH) groups, which are available for reaction with a suitable functional group on an antibody to result in the binding of the effector molecule. Alternatively, the protein is derivatized to expose or attach additional reactive functional groups. The derivatization may involve attachment of any of a number of linker molecules such as those available from Pierce Chemical Company, Rockford, Ill. The linker can be any molecule used to join the protein to the effector molecule. The linker is capable of forming covalent bonds to both the protein and to the effector molecule. Suitable linkers are well known to those of skill in the art and include, but are not limited to, straight or branched-chain carbon linkers, heterocyclic carbon linkers, or peptide linkers. Where the protein and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the Fc domain or CH3 domain when the immunoconjugate has reached its target site. Therefore, in these circumstances, immunoconjugates will comprise linkages that are cleavable in the vicinity of the target site. Cleavage of the linker to release the effector molecule from the Fc domain or CH3 domain may be prompted by enzymatic activity or conditions to which the immunoconjugate is subjected either inside the target cell or in the vicinity of the target site.

Fc Binding Variants

The monomeric Fc domains, monomeric Fc domain molecules, CH3 domains and CH3 molecules disclosed herein bind FcRn. Binding of the molecules to Fc receptors and/or compliment-related molecules such as C1q, allow for a variety of effector functions, including antibody-dependent cell-mediated cytotoxicity (ADCC), complement dependent cytotoxicity (CDC), phagocytosis, opsonization and opsonophagocytosis, although such binding typically require dimeric Fc. In some embodiments, the monomeric Fc domains, monomeric Fc domain molecules, CH3 domains and CH3 molecules disclosed herein mediate various effector functions (see Table 2 below). However, if some effector functions are not desirable, specific Fc binding site(s) can be mutated to prevent these functions. Thus, in some embodiments, Fc functions (other than FcRn binding) can be removed. Thus, monomeric Fc domains, monomeric Fc domain molecules, CH3 domains and CH3 domain molecules are provided that are at least 90%, 95%, 96%, 97%, 98%, or 99% identical to at least one of SEQ ID NO: 1, SEQ ID NO: 3, SEQ ID NO: 4, SEQ ID NO: 5, SEQ ID NO: 6, SEQ ID NO: 44, SEQ ID NO: 45, SEQ ID NO: 46, SEQ ID NO: 47 and/or SEQ ID NO: 48, wherein the polypeptide binds FcRn and is monomeric.

Each member of the Fc receptor family recognizes immunoglobulins of one or more isotypes through a recognition domain on the Fc domain. Fc receptors are defined by their specificity for immunoglobulin subtypes (for example, Fc receptors for IgG are referred to as FcγR) (U.S. Pre-Grant Publication No. 2006-0134709).

The cell expression patterns and effector functions of Fc receptors are known (see Table 2). Fc receptors allow immune cells to bind to antibodies that are attached to the surface of microbes or microbe infected cells, helping these cells to identify and eliminate microbial pathogens. The Fc receptors bind antibodies at their Fc region, an interaction that activates the cell that possesses the Fc receptor.

TABLE 4

Cell Distribution and Effector Functions of Fc Receptors

| Receptor name | Cell distribution | Effector function |
| --- | --- | --- |
| FcγRI (CD64) | Macrophages | Phagocytosis |
| | Neutrophils | Cell activation |
| | Eosinophils | Activation of respiratory burst |
| | Dendritic cells | Induction of microbe killing |
| FcγRIIA (CD32) | Macrophages | Phagocytosis |
| | Neutrophils | Degranulation (eosinophils) |
| | Eosinophils | |
| | Platelets | |
| | Langerhans cells | |
| FcγRIIB1 (CD32) | B Cells | No phagocytosis |
| | Mast cells | Inhibition of cell activity |
| FcγRIIB2 (CD32) | Macrophages | Phagocytosis |
| | Neutrophils | Inhibition of cell activity |
| | Eosinophils | |
| FcγRIIIA (CD16a) | NK cells | Induction of ADCC |
| FcγRIIIB (CD16b) | Eosinophils | Induction of microbe killing |
| | Macrophages | |
| | Neutrophils | |
| | Mast cells | |
| | Follicular dendritic cells | |
| FcεRI | Mast cells | Degranulation |
| | Eosinophils | |
| | Basophils | |
| | Langerhans cells | |
| FcεRII (CD23) | B cells | Possible adhesion molecule |
| | Eosinophils | |
| | Langerhans cells | |
| FcαRI (CD89) | Monocytes | Phagocytosis |
| | Macrophages | Induction of microbe killing |
| | Neutrophils | |
| | Eosinophils | |
| Fcα/μR | B cells | Endocytosis |
| | Mesangial cells | Induction of microbe killing |
| | Macrophages | |
| FcRn | Monocytes | Transfers IgG from a mother to fetus through the placenta |
| | Macrophages | |
| | Dendritic cells | Transfers IgG from a mother to infant in milk |
| | Epithelial cells | |
| | Endothelial cells | Protects IgG from degradation |
| | Hepatocytes | |

Activation of phagocytes is the most common function attributed to Fc receptors. For example, macrophages begin to ingest and kill an IgG coated pathogen by phagocytosis following engagement of their Fcγreceptors. Another process involving Fc receptors is called antibody-dependent cell-mediated cytotoxicity (ADCC). During ADCC, FcγRIIII receptors on the surface of natural killer (NK) cells stimulate the NK cells to release cytotoxic molecules from their granules to kill antibody covered target cells. However, FcεRI has a different function. FcεRI is the Fc receptor on granulocytes that is involved in allergic reactions and defense against parasitic infections.

In addition, the Fc domains of IgG and IgM antibodies are capable of binding C1q, a component of the classical pathway of complement activation. When IgG or IgM antibodies are bound to the surface of a pathogen, C1q is capable of binding their Fc regions, which initiates the complement cascade, ultimately resulting in the recruitment of inflammatory cells and the opsonization and killing of pathogens. Thus, variants of the present disclosed monomeric Fc domains and CH3 domain are provided herein, that bind FcRn, but do not bind or are mutated to reduce or remove binding to at least one other Fc receptor presented in Table 2, for example FcγRIIIA in order to reduce or eliminate ADCC.

Antigen Binding Fc Domains

The Fc or CH3 domains that are disclosed herein can modified so that they effectively bind any antigen of interest antigen in the absence of other immunoglobulin domains, including heavy chain variable domains, light chain variable domains, heavy chain framework regions, and/or light chain framework regions. For example, the Fc or CH3 domains can be modified such that they can specifically bind an antigen with a kD of about $10^{-6}$, about $10^{-7}$, about $10^{-8}$ or about $10^{-9}$ M or less. In some embodiments, the antigen binding monomeric Fc or CH3 domain molecules do not include a variable heavy chain domain and or a variable light chain domain at the N- and/or C-terminus of the antigen binding Fc or CH3 domain molecule, but specifically binds an antigen. These Fc domain and CH3 domains are monomeric, bind the FcRn receptor, and also bind an antigen of interest.

The Fc or CH3 domains described herein that specifically bind an antigen can include at least one heterologous amino acid sequence from an immunoglobulin variable domain, and/or comprise at least one amino acid substitution in a beta strand of the Fc domain or CH3 domain. The engrafted heterologous amino acid sequence can comprise at least one CDR, or functional fragment thereof (such as an SDR from an antibody that specifically binds an antigen of interest). Thus, in some embodiments, the engineered Fc or CH3 domain molecules comprise one or more CDRs or SDRs from a heterologous immunoglobulin variable domain, but do not include an entire variable domain. Thus engineered Fc and CH3 domains that specifically bind an antigen of interest can include one, two or three CDRs, optionally in combination with or one, two, three, four, five, six, seven, eight or nine amino acid substitutions in a beta strand.

Figure 8A:
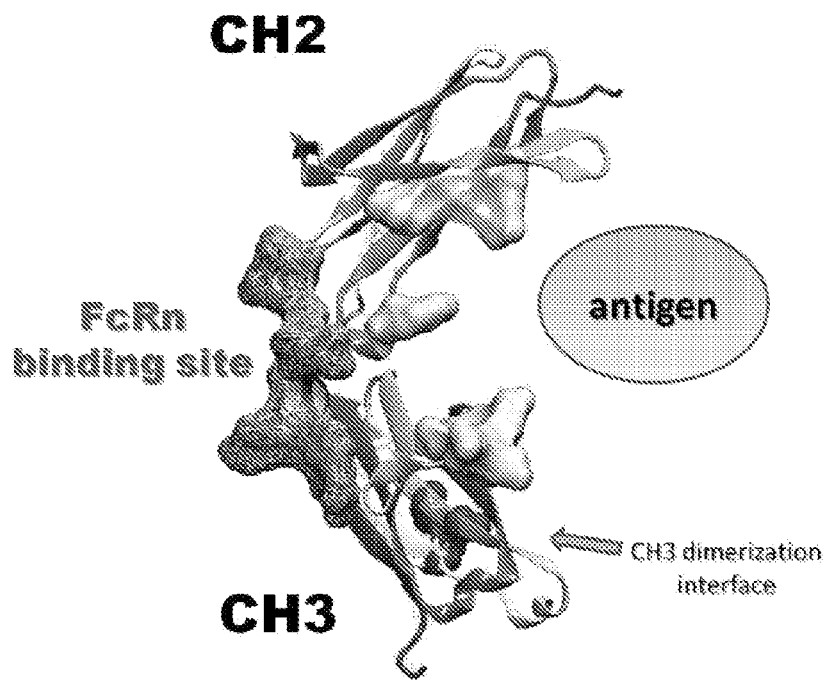
FIG. 8A and FIG. 8B are schematic diagrams of monomeric Fc that bind antigen.
Figure 8B:
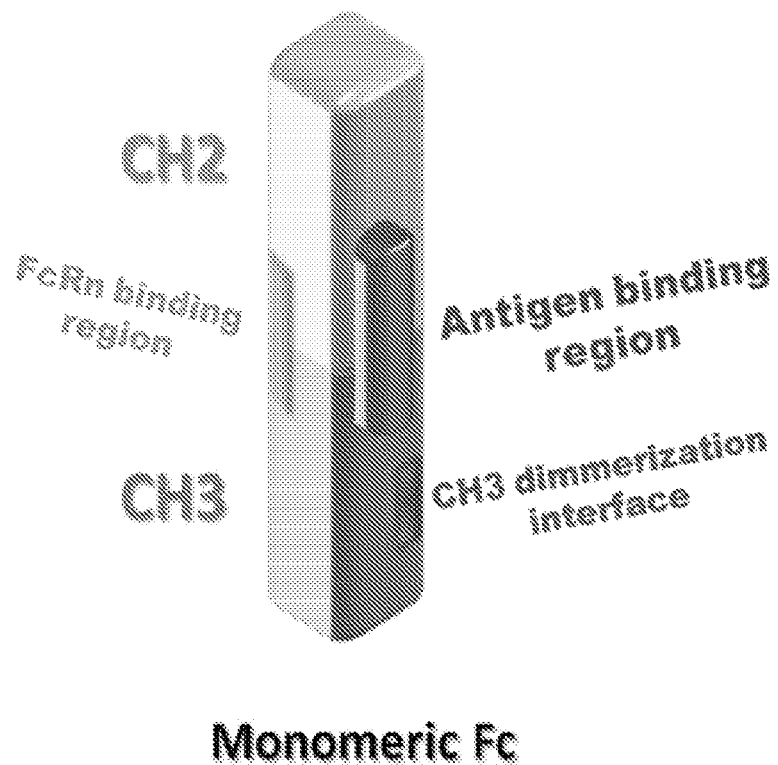

Schematic diagrams of a monomeric Fc domain, illustrating regions that bind antigen, are presented in FIGS. 8A-8B. The monomeric Fc domain that specifically binds antigen also binds FcRn. To achieve antigen binding specificity, the monomeric Fc polypeptide or CH3 polypeptide can include a CDR and/or can include one or more substitutions in a beta strand region of the molecule. In one specific non-limiting example, the monomeric Fc domain or CH3 domain includes only a single CDR sequence inserted in a beta strand.

The amino acid sequence of the human IgG Fc domain is provided as SEQ ID NO: 4. The amino acid residues comprising each of the beta strand for CH2 and CH3 are set forth below. These beta strands together form beta sheets. The amino acid positions are numbered starting with number 1 for the first residue of the Fc domain. However, the IMGT position (see Lefranc et al., Dev. Comp. Immunol. 29: 185-203, 2005, herein incorporated by reference) is shown as well in the tables below.

| Amino Acid Positions of CH2 Domain Beta Strands | | |
|---|---|---|
| Beta Strand | IMGT Position | Residue (SEQ ID NO: 2) |
| A | 239-243 | 9-13 |
| B | 258-266 | 28-36 |
| C | 272-279 | 42-49 |
| C1 | 281-284 | 51-54 |
| D | 288-294 | 58-64 |
| E | 300-307 | 70-77 |
| F | 318-325 | 88-95 |
| G | 332-337 | 102-107 |

| Amino Acid Positions of CH3 Domain Beta Strands | | |
|---|---|---|
| Beta Strand | IMGT Position | Residue (SEQ ID NO: 2) |
| A' | 347-351 | 117-121 |
| B' | 362-373 | 132-143 |
| C' | 377-383 | 147-153 |
| D' | 389-393 | 159-163 |
| E' | 404-413 | 174-183 |
| F' | 423-428 | 193-198 |
| G' | 436-441 | 206-211 |

Figure 3A:
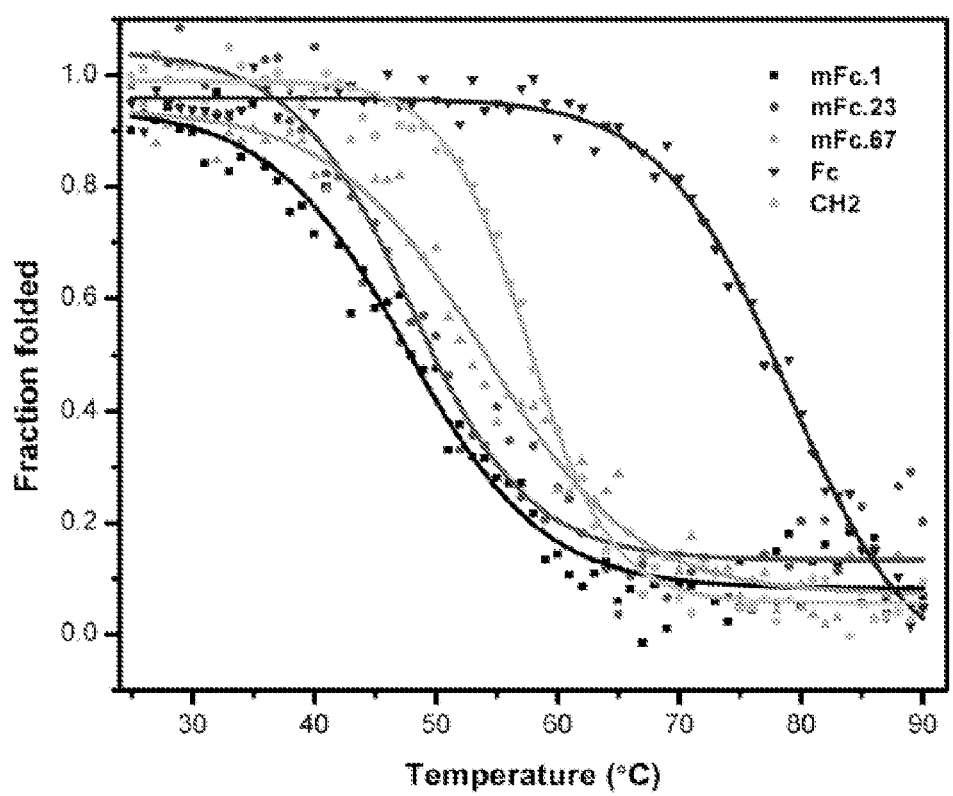
FIGS. 3A and 3B Plots of the change in fraction folded (calculated from CD molar ellipticity at 216 nm) for Fc, CH2, mFc1, mFc.23 and mFc.67. 3C, CD spectra of Fc, mFc.1, mFc.23 and mFc.67 at 25° C. (-) and refolding at 25° C. ( . . . ).
Figure 3B:
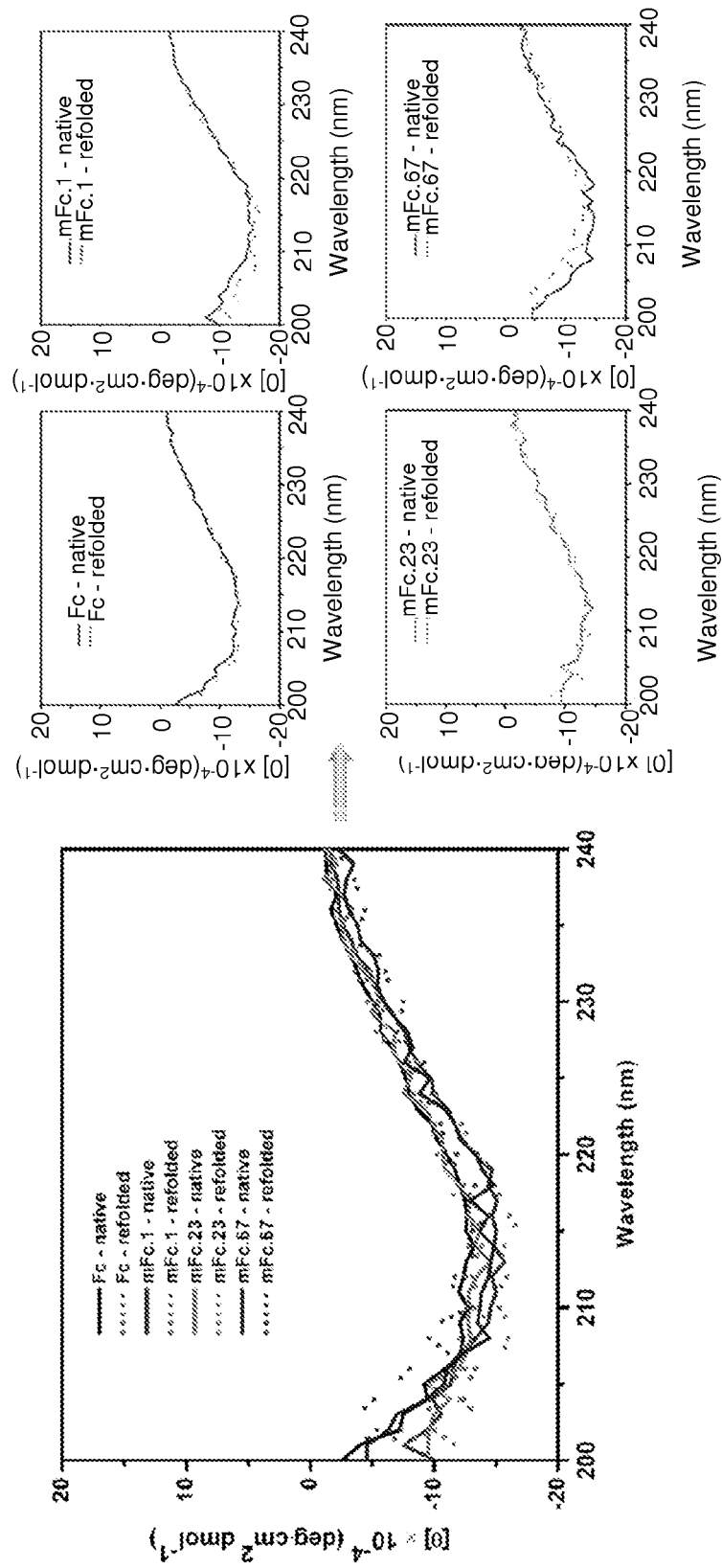

As shown in FIGS. 3A-3C of PCT Publication No. WO2009/099961, a CH2 domain comprises six loop regions: Loop 1, Loop 2, Loop 3, Loop A-B, Loop C-D and Loop E-F. Loops A-B, C-D and E-F are located between beta-strands A and B, C and D, and E and F, respectively. Loops 1, 2 and 3 are located between beta strands B and C, D and E, and F and G, respectively. See Table 1 of PCT Publication No. WO 2009/099961 for the amino acid ranges of the loops in a CH2 domain. Thus, the beta strands and the loop regions of CH2 and CH3 are delineated.

In some embodiments, the monomeric Fc polypeptide or monomeric CH3 domain that specifically binds an antigen includes at least one engrafted CDR or SDR in a beta strand, such as a single CDR or SDR in one beta strand. In other embodiments, the monomeric Fc polypeptide or monomeric CH3 domain that specifically binds an antigen includes at least one engrafted CDR or SDR in a loop region of the CH2 domain or the CH3 domain. The inserted CDR can also be inserted into a region that spans both a beta strand and loop region. Thus, one or more amino acid substitutions can be introduced into one or more beta strands, and/or a CDR can be inserted into the CH3 or CH2 domain into a beta strand and/or loop region to provide antigen specificity.

The length of the engrafted CDR or SDR can vary. Appropriate lengths can be determined empirically, such as by expressing the engineered monomeric Fc domain or CH3 domain and assessing stability and solubility of the protein, as well as by determining binding affinity. Methods of protein expression, determining protein solubility and evaluating antigen binding affinity are well known in the art. Generally, sequences of up to 21 amino acids in length can be successfully engrafted in a beta strand. Thus, the engrafted CDR can be 4 to 21 amino acids in length, such as 9-20 amino acids in length or 8-12 amino acids in length. Thus, in specific examples, the CDR is 4, 5, 6, 7, 8, 9, 10, 11, 12, 13, 14, 15, 16, 17, 18, 19, 20 or 21 amino acids in length.

In several exemplary embodiment, the amino acids from 159 to 163 of SEQ ID NO: 1, 3, 4, 5, or 6 are replaced with a CDR from the $V_H$ domain of a human antibody in a monomeric Fc domain polypeptide, with regard to mFc.23.4, or any IgG1 monomeric Fc, the CDR is grafted at position 159 (N) to 163 (T), which corresponds to IMGT positions 389-393. However, in other embodiments, the CDR is inserted after amino acid 159, 160, 161, 162, or 163 of the D' beta sheet in CH3. CDRs and/or SDRs from a heterologous immunoglobulin variable domain can be engrafted in one or more of any beta sheet in CH3 and/or CH2, in any combination. The CDR and/or SDR can be specific for any antigen of interest.

The beta strand regions in CH2 and CH3 are at most ten amino acids in length. In some embodiments, 0, 1, 2, 3, 4, 5, 6, 7, 8, 9 or 10 amino acids of one of a beta strand are replaced with 5, 6, 7, 8, 9, 10, 11, 12, 13, 14, 15, 16, 17, 18, 19, 20 or 21 amino acids of a CDRs from a heterologous antibody, in any combination. The CDR can be from a $V_L$ or a $V_H$ domain of an antibody. More than one CDR, such as two or three CDRs, can be utilized.

The engrafted CDR can be from any antibody that binds the antigen of interest. Such antibodies include, but are not limited to, pathogen-specific antibodies, cancer-specific antibodies, and autoimmune disease-specific antibodies. In some embodiments, the engineered CH2 or CH3 domain molecules comprise CDR/hypervariable sequence with a known specificity in one of the beta strands. Alternatively, the engineered CH2 domain molecules can comprise randomized CDR peptide sequence or sequences, but specifically bind the antigen of interest.

Mutational analysis of the CDRs can be performed to identify monomeric Fc domain polypeptides and monomeric CH3 domain polypeptides having increased binding affinity. In addition, libraries of monomeric Fc or monomeric CH3 domain molecules comprising randomized or mutated CDR peptide sequences can be generated to identify CH2 or CH3 domain molecules that bind with high affinity to a particular antigen of interest, such as described below.

An antigen-binding monomeric Fc domain or CH3 domain that specifically binds an antigen of interest can include 1 to 20 amino acid substitutions in a beta strand region(s), and specifically bind an antigen of interest. Thus, in some embodiments, a monomeric Fc domain molecule includes 1 to 20 amino acid substitutions in one or more beta strands of CH2 and/or CH3 domains of the amino acid sequence set forth as SEQ ID NO: 1, SEQ ID NO: 3, SEQ ID NO: 4, SEQ ID NO: 5, SEQ ID NO: 6, SEQ ID NO: 44, SEQ ID NO: 45, SEQ ID NO: 46, SEQ ID NO: 47 or SEQ ID NO: 48. In some embodiments one or more amino acid substitutions are included in one or more beta strands of the CH2 domain, such as 1-5 amino acid substitutions. The monomericFc specifically binds an antigen of interest. The monomeric Fc or CH3 that specifically binds the antigen of interest binds FcRn.

In additional embodiments, the monomeric Fc domain is 95%, 96%, 97%, 98%, or 99% identical to SEQ ID NO: 1, SEQ ID NO: 3, SEQ ID NO: 4, SEQ ID NO: 5, SEQ ID NO: 6, SEQ ID NO: 44, SEQ ID NO: 45, SEQ ID NO: 46, SEQ ID NO: 47 and/or SEQ ID NO: 48, wherein any amino acid substitutions are in the beta strand, wherein the Fc is monomeric, binds FcRn, and specifically binds the antigen of interest. In some examples, one or more amino acid substitutions are included in more than one beta strand of the CH3 domain.

In some examples, one or more of amino acids 301 to 305 (IMGT numbering) are substituted, which are in beta sheet F of the CH2 domain. Thus, in some embodiments, a monomeric Fc domain that specifically binds an antigen of interest includes an amino acid substitution at one or more of position 301, 302, 303, 304 and/or 305 using IMGT numbering. In additional examples, one or more of amino acids 389 to 393 are substituted, which are in beta sheet D' of CH3. Thus, in some embodiments, a monomeric Fc domain or a monomeric CH3 domain that specifically binds an antigen of interest includes an amino acid substitution at one or more of position 389, 390, 391, 392, and/or 393. Thus, in some examples, the antigen binding Fc domain can include substitutions at amino acid 71, 72, 73, 74 and/or 75 of SEQ ID NOs: 1, 3, 4, 5, or 6. The antigen binding Fc domain can include substitutions at amino acids 159, 160, 161, 162 and/or 163 of SEQ ID NOs: 1, 3, 4, 5, or 6. The amino acid sequences of exemplary monomeric Fc domains that specifically bind an antigen of interest are shown in SEQ ID NOs: 7-10.

Pathogen-specific monomeric Fc domains and CH3 domains, include for example, antigen binding Fc domains and CH3 domains that specifically bind an antigen from a pathogen such as viruses, bacteria or fungi, protozoa or parasites. In one exemplary embodiment, the antibody specifically binds HIV-1, such as gp120. Cancer-specific antibodies include antibodies that specifically recognize antigen expressed (such as on the cell surface) by the cancer cell, but not by other non-cancer cells. Examples of cancer-specific antibodies, include, but are not limited to, antibodies that recognize lung cancer, breast cancer, prostate cancer, liver cancer, bladder cancer, thyroid cancer, kidney cancer, pancreatic cancer, colorectal cancer, skin cancer, melanoma, neuroblastoma, Ewing's sarcoma, leukemia or lymphoma cells or tissue.

In some embodiments, the antigen is an antigen from a virus, such as a virus from one of the following families: Retroviridae (for example, human immunodeficiency virus (HIV); human T-cell leukemia viruses (HTLV); Picornaviridae (for example, polio virus, hepatitis A virus; hepatitis C virus; enteroviruses, human coxsackie viruses, rhinoviruses, echoviruses; foot-and-mouth disease virus); Calciviridae (such as strains that cause gastroenteritis); Togaviridae (for example, equine encephalitis viruses, rubella viruses); Flaviridae (for example, dengue viruses; yellow fever viruses; West Nile virus; St. Louis encephalitis virus; Japanese encephalitis virus; and other encephalitis viruses); Coronaviridae (for example, coronaviruses; severe acute respiratory syndrome (SARS) virus; Rhabdoviridae (for example, vesicular stomatitis viruses, rabies viruses); Filoviridae (for example, Ebola viruses); Paramyxoviridae (for example, parainfluenza viruses, mumps virus, measles virus, respiratory syncytial virus (RSV)); Orthomyxoviridae (for example, influenza viruses); Bunyaviridae (for example, Hantaan viruses; Sin Nombre virus, Rift Valley fever virus; bunya viruses, phleboviruses and Nairo viruses); Arena viridae (hemorrhagic fever viruses; Machupo virus; Junin virus); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses; BK-virus); Adenoviridae (most adenoviruses); Herpesviridae (herpes simplex virus (HSV)-1 and HSV-2; cytomegalovirus (CMV); Epstein-Barr virus (EBV); varicella zoster virus (VZV); and other herpes viruses, including HSV-6); Poxviridae (variola viruses, vaccinia viruses, pox viruses); and Iridoviridae (such as African swine fever virus); Filoviridae (for example, Ebola virus; Marburg virus); Caliciviridae (for example, Norwalk viruses) and unclassified viruses (for example, the etiological agents of Spongiform encephalopathies, the agent of delta hepatitis (thought to be a defective satellite of hepatitis B virus); and astroviruses). In one specific, non-limiting example, the monomeric Fc domain specifically binds gp120, but does not include a variable heavy chain domain at the N- or C-terminus.

In other embodiments, the antigen is from a bacterium, such as *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira*, or *Actinomyces israelli*.

In other embodiments, the antigen is an antigen from a fungus, such as *Cryptococcus neoformans, Histoplasma capsulatum, Coccidioides immitis, Blastomyces dermatitidis, Chlamydia trachomatis*, or *Candida albicans*. In other embodiments, the infectious disease is caused by a parasite, such as *Plasmodium falciparum* or *Toxoplasma gondii*.

In some embodiments, the antigen is a cancer antigen, such as a solid tumor or a hematogenous cancer antigen. In particular examples, the solid tumor is a sarcoma or a carcinoma, such as fibrosarcoma, myxosarcoma, liposarcoma, chondrosarcoma, osteogenic sarcoma, or another sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, or a CNS tumor (such as a glioma, astrocytoma, medulloblastoma, craniopharyogioma, ependymoma, pinealoma, hemangioblastoma, acoustic neuroma, oligodendroglioma, menangioma, melanoma, neuroblastoma or retinoblastoma).

In some examples, the hematogenous cancer is a leukemia, such as an acute leukemia (such as acute lymphocytic leukemia, acute myelocytic leukemia, acute myelogenous leukemia and myeloblastic, promyelocytic, myelomonocytic, monocytic and erythroleukemia); a chronic leukemia (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia or myelodysplasia.

Tumor antigens are well known in the art and include, for example, carcinoembryonic antigen (CEA), β-human chorionic gonadotropin (β-HCG), alpha-fetoprotein (AFP), lectin-reactive AFP, (AFP-L3), thyroglobulin, RAGE-1, MN-CA IX, human telomerase reverse transcriptase (hTERT), RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), melanoma-associated antigen (MAGE), ELF2M, neutrophil elastase, ephrinB2 and CD22. The CH2 or CH3 domain molecules can also bind any cancer-related proteins, such IGF-I, IGF-II, IGR-IR or mesothelin. Additional tumor associated antigens are provided below in Table 1 (see above).

In some embodiments, antigen is associated with an autoimmune disease, such as rheumatoid arthritis, juvenile oligoarthritis, collagen-induced arthritis, adjuvant-induced arthritis, Sjögren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia or pernicious anemia.

Antigen binding monomeric Fc domains or CH3 domains that specifically bind a first antigen of interest do not include a variable domain, such as a heavy chain variable domain and/or a light chain variable domain at the N- or C-terminus, but bind the first antigen of interest. Bi-specific molecules including these antigen binding monomeric Fc domains or CH3 domains can be produced. In some embodiments, an antigen binding monomeric Fc domains or CH3 domains that specifically binds a first antigen of interest is fused to a variable heavy chain domain or a scFc that specifically binds a second antigen of interest to produce a bi-specific molecule that specifically binds both the first antigen of interest and the second antigen of interest. Thus, an Fc domain molecule or CH3 domain molecule is produced that is bi-specific, as it binds both the first antigen of interest the second antigen of interest.

Monomeric Fc domain molecules that specifically bind an antigen are provided herein. These monomeric Fc domain molecules in include a monomeric Fc domain that specifically bind an antigen and an effector molecule. The monomeric Fc domain molecules also bind the FcRn receptor. Monomeric CH3 domain molecules that specifically bind an antigen are provided herein. These monomeric CH3 domain molecules in include a monomeric CH3 domain that specifically binds an antigen and an effector molecule. The monomeric CH3 domain molecules also bind the FcRn receptor. The effector molecule can be any effector molecule disclosed herein (see above). As noted above, monomeric Fc domains and CH3 domains can be conjugated to agents including, but not limited to, cytokines, receptors, enzymes, paramagnetic beads, colloidal paramagnetic beads, haptens, fluorochromes, metal compounds, radioactive compounds or drugs.

In some embodiments, the antigen binding Fc domain polypeptide or CH3 domain can be fused to a toxin, as described above. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.).

In yet other embodiments, the antigen binding Fc domain polypeptide or CH3 domain can be fused to a label, as described above. These labels include enzymes, paramagnetic beads, colloidal paramagnetic beads, haptens, fluorochromes, metal compounds, radioactive compounds or drugs. The enzymes include, but are not limited to, alkaline phosphatase, peroxidase, urease and β-galactosidase. The fluorochromes include, but are not limited to, fluorescein isothiocyanate, tetramethylrhodamine isothiocyanate, phycoerythrin, allophycocyanins and Texas Red. The metal compounds include, but are not limited to, ferritin, colloidal gold, and particularly, colloidal superparamagnetic beads. The haptens include, but are not limited to, biotin, digoxigenin, oxazalone, and nitrophenol. Additional reagents are well known in the art and are described in more detail above.

Nucleic Acids, Vectors and Host Cells

Nucleic acid sequences encoding the monomeric Fc domains, monomeric Fc domain molecules, monomeric CH3 domains and monomeric CH3 domain molecules disclosed herein (including those that specifically bind an antigen of interest) can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids sequences encoding a monomeric Fc domains, monomeric Fc domain molecules, antigen-binding monomeric Fc domains, antigen-binding monomeric CH3 domains, monomeric CH3 domains and monomeric CH3 domain molecules can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, a monomeric Fc domain molecule or CH3 domain molecule of use (such as, but not limited to, an antigen-binding form) is prepared by inserting the cDNA which encodes the Fc domain or CH3 domain into a vector which comprises the cDNA encoding an effector molecule (EM). The insertion is made so that the variable region and the EM are read in frame so that one continuous polypeptide is produced. Thus, the encoded polypeptide contains a functional monomeric Fc domain or CH3 domain and a functional EM region. In one embodiment, cDNA encoding an effector molecule, such as, but not limited to a cytotoxin, antibody variable domain (for example, a $V_H$ or an scFV), cytokine, or scFv, or combinations thereof is ligated to a cDNA encoding the monomeric Fc domain or CH3 domain so that the EM is located at the carboxyl terminus of the monomeric Fc domain or CH3 domain. In one example, cDNA encoding a *Pseudomonas* exotoxin ("PE"), is ligated to a monomeric Fc domain or CH3 domain so that the EM is located at the amino terminus of the molecule. In another example, a cDNA encoding a cytokine is ligated to a monomeric Fc domain or CH3 domain so that the cytokine is located at the amino terminus of the molecule. Similarly, a cDNA encoding a heavy chain variable domain or an scFv, can be utilized.

Once the nucleic acids encoding the monomeric Fc domain, CH3 domain, or fusion protein thereof (e.g., the monomeric Fc domain molecule or the CH3 domain molecule) or antigen binding form thereof, are isolated and cloned, the protein can be expressed in recombinantly engineered cells such as bacteria, plant, yeast, insect or mammalian cells. For example, one or more DNA sequences encoding the monomeric Fc domains, monomeric Fc domain molecules, monomeric CH3 domains and monomeric CH3 domain molecules can be expressed in vivo by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Alternatively the DNA sequences encoding the monomeric Fc domains and antigen binding forms thereof, monomeric Fc domain molecules, monomeric CH3 domains and antigen binding forms thereof, and monomeric CH3 domain molecules can be expressed in vitro.

Polynucleotide sequences encoding the monomeric Fc domains and antigen binding forms thereof, monomeric Fc domain molecules, monomeric CH3 domains and antigen binding forms thereof, and monomeric CH3 domain molecules can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (such as ATG) in front of a protein-encoding gene, splicing signal for introns, maintenance of the correct reading frame of that gene to permit proper translation of mRNA, and stop codons.

The polynucleotide sequences encoding the monomeric Fc domains and antigen binding forms thereof, monomeric Fc domain molecules, monomeric CH3 domains and antigen binding forms thereof, and monomeric CH3 domain molecules can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques known to those skilled in the art. Where the host is prokaryotic, such as $E.$ $coli$, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the immunotoxin, antibody, or fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide (such as the monomeric Fc domains and antigen binding forms thereof, monomeric Fc domain molecules, monomeric CH3 domains and antigen binding forms thereof, and monomeric CH3 domain molecules) can be carried out by conventional means including preparative chromatography and immunological separations. Once expressed, the recombinantly expressed polypeptide can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin. In some embodiments, the Fc domain, CH3 domain, or fusion protein thereof is at least about 99% monomeric.

Methods for expression of a protein and/or refolding to an appropriate active form, from bacteria such as *E. coli* have been described and are well-known and are applicable to the antibodies disclosed herein. See, Buchner et al., *Anal. Biochem.* 205:263-270, 1992; Pluckthun, Biotechnology 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Renaturation can be accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

In addition to recombinant methods, the monomeric Fc domains, monomeric Fc domain molecules, monomeric CH3 domains, and monomeric CH3 domain molecules disclosed herein, including antigen binding forms, can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis,* 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (e.g., by the use of the coupling reagent N, N'-dicycylohexylcarbodiimide) are well known in the art.

Fc and CH3 Domain Molecule Libraries

Libraries of engineered Fc or CH3 domain molecules comprising randomly inserted or mutated CDR amino acid sequences can be produced. The libraries can be used to screen for Fc or CH3 domain molecules having high affinity for a particular antigen of interest, and include substitutions in the beta strands. In one embodiment, the libraries are phage display libraries. Antibody phage display libraries, and methods of generating such libraries, are well known in the art (see, for example, U.S. Pat. Nos. 6,828,422 and 7,195,866, incorporated herein by reference). In some embodiments, the libraries include nucleic acids encode monomeric Fc domains that are at least 95%, 96%, 97%, 98% or 99% identical to SEQ ID NO: 1, 3, 4, 5 and/or 6.

The development of libraries of polypeptides, including antibodies, has been described (U.S. Pat. No. 6,828,422). To generate a library of polypeptides (such as a library of Fc or CH3 domain molecules), nucleic acid sequences suitable for the creation of the libraries must first be generated. To generate such randomized nucleic acid sequences, typically error-prone PCR is used. Mutations are introduced randomly the molecules. For example, a collection (such as two or three or more) of homologous proteins is identified, a database of the protein sequences is established and the protein sequences are aligned to each other. In the case of Fc domain molecules, a collection of human Fc domain sequences are identified and used to create the database using mutations. Thus, in some embodiments, error prone PCR is used to produce a library of molecules homologous to mFc.1, mFc.23, mFc.23.4 or mFc. 67.

The database is used to define subgroups of protein sequences which demonstrate a high degree of similarity in the sequence and/or structural arrangement. For each of the subgroups, a polypeptide sequence comprising at least one consensus sequence is deduced which represents the members of this subgroup (such as a subgroup of Fc domains or CH3 domains). The complete collection of polypeptide sequences represents the complete structural repertoire of the collection of homologous proteins (the Fc domains or CH3 domains). These artificial polypeptide sequences can be analyzed according to their structural properties to identify unfavorable interactions between amino acids within the polypeptide sequences or between the polypeptide sequences and other polypeptide sequences. Such interactions can be removed by changing the consensus sequence accordingly.

Next, the polypeptide sequences are analyzed to identify sub-elements, including domains, loops, β-sheets, α-helices. The amino acid sequence is back translated into a corresponding coding nucleic acid sequence which is adapted to the codon usage of the host planned for expressing the described nucleic acid sequences. A set of cleavage sites is set up such that each of the sub-sequences encoding the sub-elements identified as described above, is flanked by two sites which do not occur a second time within the nucleic acid sequence. This can be achieved by either identifying a cleavage site already flanking a sub-sequence or by changing one or more nucleotides to create the cleavage site, and by removing that site from the remaining part of the gene. The cleavage sites should be common to all corresponding sub-elements or sub-sequences, which allows for the creation of a fully modular arrangement of the sub-sequences in the nucleic acid sequence and of the sub-elements in the corresponding polypeptide.

The nucleic acid sequences described above are synthesized using any one of several methods well known in the art, such as, for example, by total gene synthesis or by PCR-based approaches.

In one embodiment, the nucleic acid sequences are cloned into a vector. The vector can be a sequencing vector, an expression vector or a display vector (such as a phage display), which are well known in the art. Vectors can comprise one nucleic acid sequence, or two or more nucleic sequences, either in a different or the same operon. If in the same operon, the nucleic acid sequences can be cloned separately or as contiguous sequences.

In one embodiment, one or more sub-sequences (such as amino acid residues within a beta strand), of the nucleic acid sequences are replaced by different sequences, such as CDR or SDR sequences. The sub-sequence can be, for example, the A', B', C', D', E', F', or G' beta strand of a CH3 domain. This can be achieved by excising the sub-sequences using the cleavage sites adjacent to or at the end of the sub-sequence, such as by an appropriate restriction enzyme, and replacing the sub-sequence by a different sequence compatible with the cleaved nucleic acid sequence. In a further embodiment, the different sequences replacing the initial sub-sequence(s) (also referred to as "engrafted sequences") are genomic or rearranged genomic sequences, for example CDRs or SDRs from a heterologous antibody. In some embodiments, the heterologous sequences are random sequences. The introduction of random sequences introduces variability into the polypeptides (form example, Fc domains, CH3 domains, Fc domain molecules or CH3 domain molecules) to create a library. The random sequences can be generated using any of a number of methods well known in the art, such as by using a mixture of mono- or tri-nucleotides during automated oligonucleotide synthesis or by error-prone PCR. The random sequences can be completely randomized or biased toward or against certain codons according to the amino acid distribution at certain positions in known protein sequences. Additionally, the collection of random sub-sequences can comprise different numbers of codons, giving rise to a collection of sub-elements having different lengths.

The nucleic acid sequences can be expressed from a suitable vector under appropriate conditions well known in the art. In one embodiment, the polypeptides expressed from the nucleic acid sequences are screened. The polypeptides can further be optimized. Screening can be performed by using any method well known in the art, such as phage-display, selectively infective phage, polysome technology to screen for binding, assay systems for enzymatic activity or protein stability. Polypeptides (such as Fc domains, CH3 domains, Fc domain molecules or CH3 domain molecules) having the desired property can be identified by sequencing the nucleic acid sequence or amino acid sequence, or by mass spectrometry. The desired property the polypeptides are screened for can be, for example, optimized affinity or specificity for a target molecule. The property can also be FcRn binding.

In some embodiments, phagemid vectors can be used to simultaneously express a large number of nucleic acid sequences, such as those encoding a library of Fc domains, CH3 domains, Fc domain molecules or CH3 domain molecules (see, for example, U.S. Patent Application Publication No. 2008/0312101). The libraries of phage particles can be screened using any screening assay known to be applicable with phage. For example, the phage can be exposed to a purified antigen, soluble or immobilized (e.g. on a plate or on beads) or exposed to whole cells, tissues, or animals, in order to identify phage that adhere to targets present in complex structures, and in particular in physiologically or therapeutically relevant locations (e.g. binding to cancer cells or to an antigen on a viral particle). The particles can also be screened to identify only those molecules that are monomeric.

The selected phagemid vectors in which a heterologous sequence has been cloned, expressed, and specifically isolated on the basis of its binding for a specific ligand, can be extracted from the bacterial cells, and sequenced, PCR-amplified, and/or recloned into another appropriate vector, for example for the large scale recombinant production in bacterial, plant, yeast, or mammalian cells.

The detection of the interaction with the specific target antigen can be performed by applying standard panning methods, or by applying more sophisticated biophysical technologies for assessment of interactions between the displayed monomeric Fc or CH3 binding molecule and its target antigen, such as fluorescence-based spectroscopy or microscopy, phosphatase reaction, or other high-throughput technologies. Thus, methods are provided of identifying a monomeric Fc domain or CH3 domain that specifically binds a target antigen, that include contacting the library with a target antigen to select recombinant monomeric Fc domains or CH3 domains that specifically bind the target antigen.

Once monomeric Fc or CH3 domain-expressing phage particles that specifically bind a target antigen have been selected, the recombinant phage and the relevant DNA sequence can be isolated and characterized according to the methods known in the art (e.g. separated from the phagemid vector using restriction enzymes, directly sequenced, and/or amplified by PCR). These sequences can be then transferred into more appropriate vectors for further modification and/or expression into prokaryotic or eukaryotic host cells. The DNA sequence coding for the monomeric Fc or CH3 domain, once inserted into a suitable vector, can be introduced into appropriate host cells by any suitable means (transformation, transfection, conjugation, protoplast fusion, electroporation, calcium phosphate precipitation, direct microinjection, etc.) to transform the cells.

This collection of DNA molecules can then be used to create libraries of monomeric Fc or CH3 domain molecules. The affinity of the monomeric Fc or CH3 domain molecules can be optimized using the methods described above. The libraries can be used to identify one or more monomeric Fc or CH3 domain molecules that bind to a target and/or bind FcRn. Identification of the desired monomeric Fc or CH3 domain molecules comprises expressing the monomeric Fc or CH3 domain molecules and then screening them to isolate one or more molecules that bind to a given target molecule with the desired affinity.

If necessary, the modular design of the DNA molecules allows for excision of one or more genetic sub-sequences and replacement with one or more second sub-sequences encoding structural sub-elements. Thus, the expression and screening steps can then be repeated until a monomeric Fc or CH3 domain molecule having the desired affinity is generated, with one or more replacements in specific sub-sequences, such as those that encode a beta strand.

In one embodiment is a method in which one or more of the genetic subunits (for example, one or more CH2 or CH3 beta strands regions (see above) are replaced by a random collection of sequences (the library) using the cleavage sites. The resulting library is then screened against any chosen antigen. Monomeric Fc or CH3 domain molecules with the desired properties (such as having the desired binding affinity) are selected, collected and can be used as starting material for the next library.

In another embodiment, monomeric Fc domain molecules or CH3 domain molecules can be generated by providing a DNA sequence which encodes either the monomeric Fc domain or the CH3 domain, as described above, and an additional moiety. Such moieties include, but are not limited to, effector molecules, such as immunotoxins, cytokines, receptors, enzymes, therapeutic molecules, and labels, and/or tags (such as for detection and/or purification).

Also provided herein are the nucleic acid sequences, vectors containing the nucleic acid sequences, host cells containing the vectors, and polypeptides, generated according to the methods described above.

Further provided are kits comprising one or more of the nucleic acid sequences, recombinant vectors, polypeptides, and/or vectors according to the methods described above, and suitable host cells for producing the polypeptides.

Use of Fc and CH3 Domain Molecules for Diagnosis or Treatment

Antigen binding monomeric Fc domains, antigen binding monomeric CH3 domains, Fc domain molecules, and CH3 domain molecules a have enormous potential for diagnosis and/or treatment of any of a number of diseases or conditions for which an antibody is of use. For example, they can be used for the treatment of cancer, infectious disease (such as viral, bacterial, fungal or parasitic infections), autoimmune disease, inflammatory disorders, or any other disease or condition for which antibodies or their fragments can be used as therapeutic agents. In some embodiments, for the treatment of a disease or disorder, the monomeric Fc domain molecule or CH3 domain molecule include a variable heavy chain domain that specifically binds an antigen associated with the disorder, such as a tumor associated antigen or an antigen from a pathogen. In other embodiments, an antigen binding Fc domain or CH3 domain is utilized that does not include a variable heavy chain domain at the N-terminus of the C-terminus. However, one of skill in the art will readily appreciate that other effector molecules can be used to treat a specific disorder, such as, but not limited to, monomeric Fc molecules and CH3 molecules that include a cytokine.

Generally the methods include administering to the subject a therapeutically effective amount of the antigen binding monomeric Fc domain, antigen binding monomeric CH3 domain, Fc domain molecule, or CH3 domain molecules, thereby treating the subject.

In some embodiments, the subject has an infectious disease. The infectious disease can be caused by a virus, such as a virus from one of the following families: Retroviridae (for example, human immunodeficiency virus (HIV); human T-cell leukemia viruses (HTLV); Picornaviridae (for example, polio virus, hepatitis A virus; hepatitis C virus; enteroviruses, human coxsackie viruses, rhinoviruses, echoviruses; foot-and-mouth disease virus); Calciviridae (such as strains that cause gastroenteritis); Togaviridae (for example, equine encephalitis viruses, rubella viruses); Flaviridae (for example, dengue viruses; yellow fever viruses; West Nile virus; St. Louis encephalitis virus; Japanese encephalitis virus; and other encephalitis viruses); Coronaviridae (for example, coronaviruses; severe acute respiratory syndrome (SARS) virus; Rhabdoviridae (for example, vesicular stomatitis viruses, rabies viruses); Filoviridae (for example, Ebola viruses); Paramyxoviridae (for example, parainfluenza viruses, mumps virus, measles virus, respiratory syncytial virus (RSV)); Orthomyxoviridae (for example, influenza viruses); Bunyaviridae (for example, Hantaan viruses; Sin Nombre virus, Rift Valley fever virus; bunya viruses, phleboviruses and Nairo viruses); Arena viridae (hemorrhagic fever viruses; Machupo virus; Junin virus); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses; BK-virus); Adenoviridae (most adenoviruses); Herpesviridae (herpes simplex virus (HSV)-1 and HSV-2; cytomegalovirus (CMV); Epstein-Barr virus (EBV); varicella zoster virus (VZV); and other herpes viruses, including HSV-6); Poxviridae (variola viruses, vaccinia viruses, pox viruses); and Iridoviridae (such as African swine fever virus); Filoviridae (for example, Ebola virus; Marburg virus); Caliciviridae (for example, Norwalk viruses) and unclassified viruses (for example, the etiological agents of Spongiform encephalopathies, the agent of delta hepatitis (thought to be a defective satellite of hepatitis B virus); and astroviruses). In one specific non-limiting example, the infectious disease is caused by HIV, and the antigen binding monomeric Fc domain, antigen binding monomeric CH3 domain, Fc domain molecule, or CH3 domain molecules specifically binds gp120.

In other embodiments, the infectious disease is caused by a type of bacteria, such as *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria* gonorrhoeae, Neisseria meningitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic sps.), Streptococcus pneumoniae, pathogenic Campylobacter sp., Enterococcus sp., Haemophilus influenzae, Bacillus anthracis, corynebacterium diphtheriae, corynebacterium sp., Erysipelothrix rhusiopathiae, Clostridium perfringers, Clostridium tetani, Enterobacter aerogenes, Klebsiella pneumoniae, Pasturella multocida, Bacteroides sp., Fusobacterium nucleatum, Streptobacillus moniliformis, Treponema pallidium, Treponema pertenue, Leptospira, or Actinomyces israelii.

In other embodiments, the infectious disease is caused by a fungus, such as Cryptococcus neoformans, Histoplasma capsulatum, Coccidioides immitis, Blastomyces dermatitidis, Chlamydia trachomatis, or Candida albicans. In other embodiments, the infectious disease is caused by a parasite, such as Plasmodium falciparum or Toxoplasma gondii.

In some embodiments, the subject has cancer. The cancer can be a solid tumor or a hematogenous cancer. Thus, a method is provided for treating a cancer in a subject. The methods can result in reducing tumor burden, and/or decreasing metastasis.

In particular examples, the solid tumor is a sarcoma or a carcinoma, such as fibrosarcoma, myxosarcoma, liposarcoma, chondrosarcoma, osteogenic sarcoma, or another sarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, or a CNS tumor (such as a glioma, astrocytoma, medulloblastoma, craniopharyogioma, ependymoma, pinealoma, hemangioblastoma, acoustic neuroma, oligodendroglioma, menangioma, melanoma, neuroblastoma or retinoblastoma).

In some examples, the hematogenous cancer is a leukemia, such as an acute leukemia (such as acute lymphocytic leukemia, acute myelocytic leukemia, acute myelogenous leukemia and myeloblastic, promyelocytic, myelomonocytic, monocytic and erythroleukemia); a chronic leukemia (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia or myelodysplasia.

In some embodiments, Fc domain or CH3 domain molecule is included in fusion protein specifically binds a tumor antigen. Tumor antigens are well known in the art and include, for example, carcinoembryonic antigen (CEA), α-human chorionic gonadotropin (α-HCG), alpha-fetoprotein (AFP), lectin-reactive AFP, (AFP-L3), thyroglobulin, RAGE-1, MN-CA IX, human telomerase reverse transcriptase (hTERT), RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), melanoma-associated antigen (MAGE), ELF2M, neutrophil elastase, ephrinB2 and CD22. The CH2 or CH3 domain molecules can also bind any cancer-related proteins, such IGF-I, IGF-II, IGR-IR or mesothelin. Additional tumor associated antigens are provided below in Table 1 above.

Methods are also provided for threating an autoimmune disorder in a subject. In some embodiments, the autoimmune disease is rheumatoid arthritis, juvenile oligoarthritis, collagen-induced arthritis, adjuvant-induced arthritis, Sjögren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia or pernicious anemia.

The wide utility of monomeric Fc and CH3 domain molecules, antigen-binding monomeric Fc domains and antigen binding monomeric CH3 domains, is due at least in part to their small size, which allows for efficient penetration in tissues, including solid tumors and lymphoid tissue where HIV replicates, and also permits efficient neutralization of pathogens, such as viruses (for example, HIV) that rapidly evolve to avoid neutralization by immunoglobulins generated by the host immune system.

Engineered Fc or CH3 domains molecules are also useful for treatment due to their amenability for creating high-affinity binding antibodies to any antigen of interest. As described herein, the Fc or CH3 domain molecules can further comprise an effector molecule with therapeutic properties (such as, for example, a drug, enzyme or toxin). These molecules bind FcRn, and are stable and have a long half-life.

Fc and CH3 domain molecules are usually administered to a subject as compositions comprising one or more pharmaceutically acceptable carriers. Such carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight, general condition of the subject, the particular bleeding disorder or episode being treated, the particular CH2 or CH3 domain molecule being used and its mode of administration. An appropriate dose can be determined by one of ordinary skill in the art using only routine experimentation.

Provided herein are pharmaceutical compositions which include a therapeutically effective amount of an monomeric Fc domain molecule, monomeric CH3 domain molecule, antigen binding monomeric Fc domain, or antigen binding CH3 domain, alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

Use of Fc Domains and CH3 Domains for Detection

Methods of determining the presence or absence of a polypeptide with specific binding agents, such as antibodies and functional fragments thereof, are well known in the art. These methods can be adapted for use with other specific binding agents, such as an Fc or CH3 domain molecules, or antigen binding forms of an Fc domain or CH3 domain. In some examples, an Fc or CH3 domain molecules, or antigen binding forms of an Fc domain or CH3 domain, can be conjugated to other compounds including, but not limited to, enzymes, magnetic beads, colloidal magnetic beads, haptens, fluorochromes, metal compounds, radioactive compounds or drugs. The Fc or CH3 domain molecules that include a specific binding agent, such as, but not limited to, an antibody heavy chain variable domain or an scFv, or antigen binding forms of an Fc domains or CH3 domains, can also be utilized in immunoassays such as but not limited to radioimmunoassays (RIAs), enzyme linked immunosorbent assays (ELISA), immunohistochemical assays, Western blot or immunoprecipitation assays. These assays are well known in the art (see Harlow & Lane, *Antibodies, A Laboratory Manual*, Cold Spring Harbor Publications, New York (1988), for a description of immunoassay formats).

In one embodiment, a diagnostic kit comprising an immunoassay is provided. Although the details of the immunoassays may vary with the particular format employed, the method for detecting an antigen in a biological sample generally includes the steps of contacting the biological sample with a monomeric Fc or CH3 domain molecule, or antigen binding form of an Fc domain or CH3 domain, which specifically reacts, under immunologically reactive conditions, to the antigen of interest. In some embodiments, the Fc or CH3 domain molecule includes a VH domain, diabody, engineered antibody domain or scFv. The Fc or CH3 domain molecule, or antigen binding form of a monomeric Fc domain or CH3 domain, is allowed to specifically bind under immunologically reactive conditions to form an immune complex, and the presence of the immune complex (bound antigen) is detected directly or indirectly.

The Fc or CH3 domain molecules that specifically bind an antigen of interest, or antigen binding forms of a monomeric Fc domain or CH3 domain, as disclosed herein, can also be used for fluorescence activated cell sorting (FACS). A FACS assay employs a plurality of color channels, low angle and obtuse light-scattering detection channels, and impedance channels, among other more sophisticated levels of detection, to separate or sort cells (see U.S. Pat. No. 5,061,620). FACS can be used to sort cells that are antigen positive, by contacting the cells with an appropriately labeled Fc or CH3 domain molecule, or antigen binding form of a monomeric Fc domain or CH3 domain. However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Additional separation procedures may include magnetic separation, using, for example, Fc or CH3 domain molecule-coated magnetic beads, affinity chromatography, cytotoxic agents, either joined to an Fc or CH3 domain molecule or used in conjunction with complement, and "panning," which utilizes an antigen binding form, or Fc or CH3 domain molecule, attached to a solid matrix, or another convenient technique. The attachment of specific binding agents to magnetic beads and other solid matrices, such as agarose beads, polystyrene beads, hollow fiber membranes and plastic Petri dishes, allow for direct separation. Cells that are bound by the specific binding agent, such as an Fc or CH3 domain molecule, can be removed from the cell suspension by simply physically separating the solid support from the cell suspension. The exact conditions and duration of incubation of the cells with the solid phase-linked antigen binding Fc domain, antigen binding CH3 domain, or Fc or CH3 domain molecules, will depend upon several factors specific to the system employed. The selection of appropriate conditions, however, is well known in the art.

Unbound cells then can be eluted or washed away with physiologic buffer after sufficient time has been allowed for the cells expressing an antigen of interest to bind to the solid-phase linked binding agent. The bound cells are then separated from the solid phase by any appropriate method, depending mainly upon the nature of the solid phase and the Fc or CH3 domain molecule employed, and quantified using methods well known in the art. In one specific, non-limiting example, bound cells separated from the solid phase are quantified by FACS.

Monomeric Fc or CH3 domains, or monomeric Fc or CH3 domain molecules can be conjugated to biotin, which then can be removed with avidin or streptavidin bound to a support, or fluorochromes, which can be used with FACS to enable cell separation and quantitation, as known in the art.

As noted above, Fc or CH3 domain molecules, or antigen binding forms of monomeric Fc domains or CH3 domains, can be conjugated to other compounds including, but not limited to, enzymes, paramagnetic beads, colloidal paramagnetic beads, haptens, fluorochromes, metal compounds, radioactive compounds or drugs. The enzymes that can be conjugated include, but are not limited to, alkaline phosphatase, peroxidase, urease and β-galactosidase. The fluorochromes that can be conjugated to the Fc domain or CH3 molecules include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals* (1992-1994). The metal compounds that can be conjugated include, but are not limited to, ferritin, colloidal gold, and particularly, colloidal superparamagnetic beads. The haptens that can be conjugated include, but are not limited to, biotin, digoxigenin, oxazalone, and nitrophenol. Additional reagents are well known in the art.

The disclosure is illustrated by the following non-limiting Examples.

EXAMPLES

The experiments disclosed herein described antigen binding molecules wherein the size of Fc has been decreased. These monomeric Fc domains were identified by using a novel screening strategy to develop functional and highly soluble Fc monomers. Fc dimerization is mainly mediated by a large hydrophobic interface in its CH3 domain, which involves at least 16 residues in each polypeptide chain that make intermolecular interactions. When the compulsory complex is broken, it can cause exposure of a hydrophobic surface and thus make the molecules suffer from poor solubility, instability and/or aggregation. To solve this problem, a large phage library was constructed in which more than $10^9$ human IgG1 Fc individuals were displayed with extensive mutations in CH3 dimer interface. This library was first selected by protein G, to screen soluble and well folded variants, and then functional clones were further enriched by panning directly against human FcRn for several rounds.

Four monomeric Fc proteins, mFc.1, mFc.23, mFc.23.4 and mFc.67, were generated which are >99% monomeric as indicated by size exclusion chromatography. These novel antibody formats are relatively stable, and also represent the smallest functional fragments (~27 kD) in IgG that retain binding to FcRn comparable to that of Fc. A preliminary investigation has shown that a VH-monomeric Fc fusion protein is still monomeric and functional, suggesting that using monomeric Fc to replace dimeric wild-type Fc for generating fusion proteins is very promising. Moreover, monomeric Fc can be high efficiently expressed in *E. Coli*, with a yield of 15-20 mg purified proteins per liter culture which is twice that of wild-type Fc. These monomeric Fc can be used as scaffolds for antibody engineering. These antigen binding molecules have small size, long half-life and antigen-binding ability.

Example 1

Materials and Methods

Library Construction and Selection of Monomeric Fc Clones:

A large phage display library (~1.3×10⁹ individuals) was constructed by randomly mutating seven residues located at the CH3 dimer interface of human IgG1 Fc (L351, T366, L368, P395, F405, Y407, K409). Amplified libraries with $10^{12}$ phage-displayed Fc mutants were applied to a pre-equilibrated protein G column (Roche, Indianapolis, Ind.). The resins were washed extensively with PBS, and the bounded phages were eluted by 0.1 M HCl-glycine (pH 2.2). The elution was then neutralized with 1 M Tris-base, mixed with TG1 cells for 1 hour (h) at 37° C., and the phages capable of binding to protein G were amplified from the infected cells and used in the biopanning against FcRn. The human FcRn, containing both 0 and a chains in 1:1 molar ratio, was expressed in mammalian cells and purified as a soluble protein as previously described. Libraries with $10^{12}$ phages were mixed with PBS (pH 6.0), incubated in ELISA wells coated with FcRn for 2 h at 37° C. After incubation the wells were washed 10 times for the first round and 20 times for the later rounds with PBS (pH 6.0) containing 0.05% Tween 20, and the bound phages were eluted with PBS (pH 7.4), amplified by infecting TG1 cells along with helper phage M13K07 (Invitrogen, Carlsbad, Calif.). 80 clones were randomly picked from the fifth selection round, transferred into HB2151 cells, inoculated into 3 mL 2YT medium containing 100 µg/mL ampicillin, and incubated for 2 h at 37° C. with shaking at 250 rpm. After the addition of 1.5 µL IPTG, bacteria were grown for 3 additional hours, harvested by centrifugation. The pellet was resuspended in PBS buffer containing 5 µU polymixin B (Sigma-Aldrich), incubated at room temperature for 30 min, and centrifuged at 10,000 rpm for 10 min. The supernatant were separated by non-reducing SDS-PAGE without boil and then analyzed by western blot. spectra were recorded at 25° C. for native structure measurements. The clones which did not have ~54 kD bands on the western blot were selected for further characterization.

Expression and Purification of Monomeric Fc Proteins: The selected clones (mFc.1, mFc.23 and mFc.67) were sequenced, and plasmids extracted from these clones were used for transformation of HB2151 cells. A single and freshly transformed colony was inoculated into 200 mL SB medium with 100 µg/mL ampicillin, and incubated at 37° C. with vigorous shaking at 250 rpm. When optical density of the culture at 600 nm reached around 0.6, expression was induced by the addition of IPTG to a final concentration of 1 mM, and the culture was further incubated at 30° C. for 6 h. Then, cells were harvested by centrifugation at 6,000 rpm for 15 min and resuspended in phosphate buffered saline (PBS). Polymixin B (Sigma-Aldrich, St. Louis, Mo.) (0.5 mu/mL) was added to the suspension (1:1000). After 30 min incubation with rotation at 50 rpm at room temperature, the culture was centrifuged at 12,000 rpm for 15 min at 4° C. The supernatant was used for further purification by Ni-NTA resin (Qiagen, Valencia, Calif.) according to manufacturer's protocols. Protein purity was estimated as >95% judged by SDS-PAGE and protein concentration was measured spectrophotometrically (NanoVue, GE Healthcare).

Size Exclusion Chromatography: The molecular composition of purified proteins was analyzed by size exclusion chromatography (SEC) using an FPLC AKTA BASIC pH/C system (GE Healthcare) with a Superdex 75 10/300 GL column (GE Healthcare). PBS (pH 7.4) was selected as running buffer and a flow rate of 0.5 mL/min was used. Eluting protein was monitored at 280 nm. The molecular mass standards used were ribonuclease A (13.7 kDa), chymotrypsinogen A (25 kDa), ovalbumin (44 kDa), bovine serum albumin (67 kDa) and aldolase (158 kDa).

Reverse Mutation: The reverse mutation assay was conducted using a selected monomeric Fc clone mFc.23 as template, in which the dependent residues were mutated back to their original counterparts in wild-type Fc. Six mFc.23 mutants, 351L, 366T, 368L, 366T/368L, 395P and 405F/407Y/409K were all generated by the overlap-extension PCR method. Each mutation was confirmed by automated DNA sequencing. The reverse mutations were expressed and purified using a similar procedure as for monomeric Fc proteins described above.

Circular Dichroism: The circular dichroism (CD) spectra of CH2, Fc and monomeric Fc proteins were collected from 190 to 250 nm (0.1 cm path length), with an AVIV Model 202 spectropolarimeter (Aviv Biomedical). The protein samples were dissolved in PBS, pH 7.4 at the final concentration of 0.4 mg/mL. Firstly, spectra were recorded at 25° C. for native structure measurements. For evaluation of the refolding, the samples were heated slowly to 90° C. (1° C./min), kept at 90° C. for 10 min, then rapidly cooled down to 25° C. (10° C./min) and the spectra were recorded again. For evaluation of thermal stability, CD signals at 216 nm were recorded and the instrument was programmed to acquire spectra at 1° C. internals over the range 25-90° C.

Spectrofluorometry: Fluorescence spectra were measured using a Fluoromax-3 spectrofluorometer (HORIBA Jobin Yvon Inc., NJ). For urea denaturation tests, Fc and monomeric Fc proteins were dissolved in urea-containing buffers (50 mM Tris-Cl, 450 mM NaCl, pH 8.0, 0 to 8 M Urea), to give a final protein concentration of 10 μg/mL. The samples were kept overnight at 4° C. and fluorescence measurements were performed with the excitation wavelength at 280 nm. The emission spectra were recorded from 320 to 380 nm, and fluorescence intensity at 343 nm was used for quantitative evaluation of urea unfolding.

Serum Stability Assay: Normal human serum was collected from healthy human donors approved by NCI-Frederick Research Donor Program (RDP). Wild-type human Fc (30 μg) and monomeric Fc proteins (15 μg) were incubated with normal human serum in PBS at 37° C. An aliquot was taken out at each time point and immediately stored at −80° C. Western blotting and ELISA assays were applied to check the serum stability. For Western blotting, samples were electrophoresed through SDS-PAGE and transferred onto a 0.2 μm nitrocellulose membrane (Bio-Rad). The membrane was blocked with 3% milk in PBS for 1 h at room temperature, and then incubated with anti-His Tag monoclonal (ABM, Vancouver, Canada) for 1 h. Washing with PBST was followed by incubation with anti-mouse IgG-alkaline phosphatase antibody (Sigma-Aldrich). The BCIP/NBT substrate solution (Sigma-Aldrich) was used for detection. For ELISA test, wells were coated with 50 uL of anti-Fc Fab (Sigma-Aldrich), blocked in 100 uL protein-free blocking buffer (Thermo Scientific) for 1 h at 37° C. After five washes with PBST, wells were incubated with samples for 2 h at 37° C. Following six washes with PBST, 50 uL horseradish peroxidase (HRP)-conjugated anti-FLAG tag antibody (Sigma-Aldrich) were added and incubated for 1 h at 37° C. The assay was developed with ABTS substrate (Roche, Indianapolis, Ind.) and monitored at 405 nm.

Binding ELISA: Antigens were coating on ELISA plate wells at 50 ng per well in PBS overnight at 4° C., blocked with protein-free blocking buffer for 1 h at 37° C. Threefold serially diluted protein was added and incubated at 37° C. for 2 h. The plates were washed with PBST, and HRP-conjugated anti-Fc antibody in PBS was incubated with wells for 1 h at 37° C. After extensive washes with PBST, the binding was detected with the addition of ABTS substrate, and signals were read at 405 nm. For FcRn binding test at pH 6.0, all proteins were prepared in PBS with pH adjusted to 6.0 by HCl, and PBST with pH 6.0 was used for washing the wells. The Fc I253A/S254A/H435A/Y436A mutant was constructed as a negative control for FcRn binding using overlap-extension method.

Surface Plasmon Resonance (SPR) Experiments: The interaction of monomeric Fc with immobilized FcRn was monitored by SPR detection using a BIAcore X100 instrument (GE Healthcare). Purified human FcRn was diluted in 10 mM Na-acetate buffer, pH 5.0, and immobilized on a CM5 biosensor chip using amine coupling kit. The running buffer was PBS with 0.005% Tween 20 for testing binding at pH 7.4, or PBS pH 6.0 with 0.005% Tween 20 for binding at pH 6.0. The proteins diluted with running buffer was let flow through the cells, at concentration ranging from 125 nM to 2000 nM. After 10 min of dissociation, the chip was regenerated with pH 8.0 buffer (100 mM Tris, pH 8.0, 50 mM NaCl). Another test with a protein concentration of 500 nM was repeated to monitor the regeneration efficiency.

Construction of m36 Fusion Proteins: The following primers were used:

```
Omp,
                                       (SEQ ID NO: 11)
5'-AAGACAGCTATCGCGATTGCAG-3';

gIIIF,
                                       (SEQ ID NO: 12)
5'-ATCACCGGAACCAGAGCCACCAC-3';;

m36R,
                                       (SEQ ID NO: 13)
5'-TGAGGAGACGGTGACCAGGGTGCCCTG-3';

mFcF,
                                       (SEQ ID NO: 14)
5'-CTGGTCACCGTCTCCTCAGCACCTGAACTCCTGGG-3';

mFcCH3F,
                                       (SEQ ID NO: 15)
5'-CTGGTCACCGTCTCCTCACCCCGAGAACCACAGGTGTAC-3'.
```

The m36 gene was amplified by PCR (primer: Omp and m36R) with m36-encoding plasmid pCom36 as a template. The mFc.67 gene (primer: mFcF and gIIIF) and mFc.67 CH3 domain gene (primer: mFcCH3F and gIIIF) were amplified from mFc.67 plasmid which was constructed in pComb3x vector. M36 fragment was joined to mFc.67 or CH3 domain of mFc.67 by overlap-extension PCR, and the products were digested with SfiI enzyme, cloned into pComb3x vector. The fusion proteins were expressed and purified using a similar procedure as for monomeric Fc proteins described above.

Example 2

Screening a Large Fc Mutation Library for Monomeric Fc

A combination of structure-based rational protein design combined with multiple screening strategies of Fc mutant libraries was utilized to identify monomeric Fcs (mFcs). Fc dimerization is mainly mediated by a large (1000 Å buried surface), tightly packed interface between the two CH3 domains (FIG. 1A). This interface is composed of multiple regions containing at least 16 residues in each chain, most of which are hydrophobic. Four regions were identified in the CH3 domain of human IgG1 contributing to the interchain interactions with the following critical contact residues: L351, T366 and T368, P395, F405, Y407 and K409 (FIG. 1B). This is in agreement with previous studies, e.g. significant destabilizing effects were found by mutation of the above seven residues in human IgG1 CH3. Two problems must be solved to generate the soluble Fc monomer: breaking strong interactions between these residues and prevention of protein aggregation due to exposure of hydrophobic residues.

It was hypothesized that functional and highly soluble Fc monomers could be produced by panning and screening for proper folding, binding to FcRn and solubility of a large Fc library with extensive mutations in the hydrophobic interface. Thus, a phage library was constructed by randomly mutating the above seven residues (L351, T366, L368, P395, F405, Y407, K409) in human IgG1 Fc. Initially this library was panned directly against human single-chain soluble FcRn. Buffer with pH 6.0 was used for washing and buffer with pH 7.4 was used for elution to select pH-dependent binders. However, there was no enrichment after two rounds of panning. It is likely that functional binders were masked by ubiquitous misfolded molecules in the library. Thus, this library was first panned against protein G resulting in a library enriched for phage-displayed soluble and well-folded mFcs. This library was further panned against human FcRn for 5 rounds as described above. To select for highly expressed monomers 80 clones from the final enriched library were expressed in *E. Coli* and screened by using non-reducing SDS-PAGE and Western blot. This panning/screening procedure is schematically depicted in FIG. 1C.

Figure 2B:
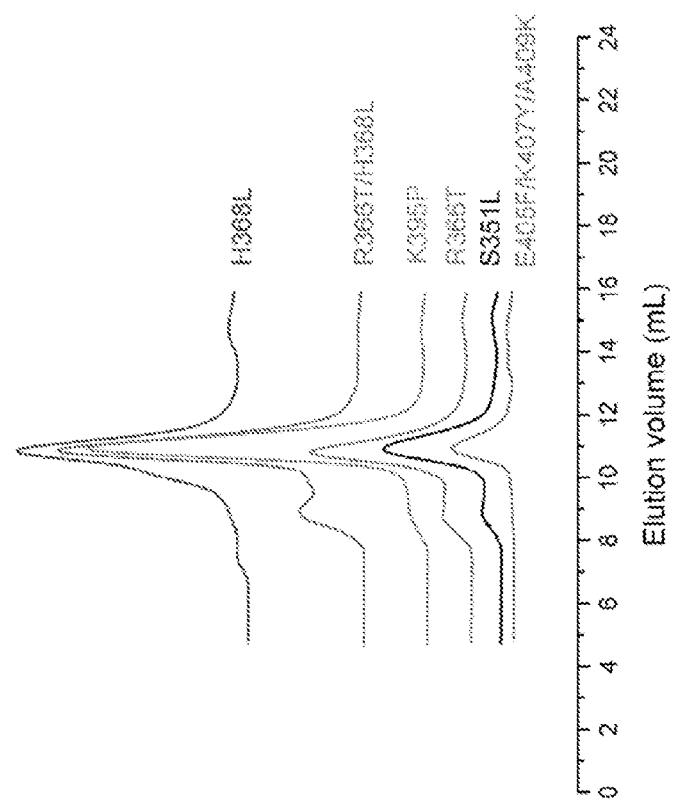
FIG. 2B Size exclusion chromatography of the 351L, 366T, 368L, 366T/368L, 395P and 405F/407Y/409K (IMGT numbering) mutants of mFc.23. The inset shows a standard curve for the gel filtration standards.
Figure 2A:
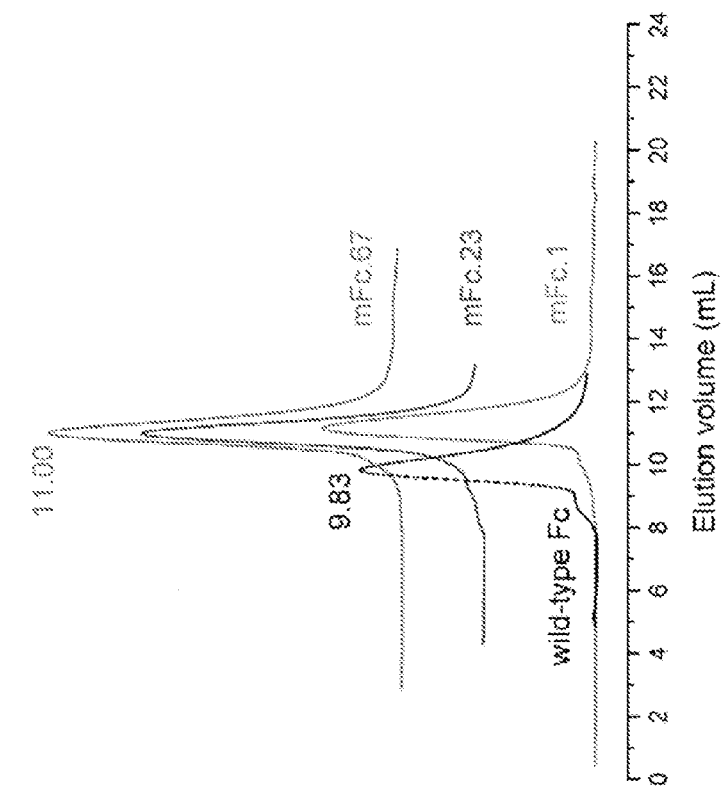
FIG. 2A Size exclusion chromatography of wild-type IgG1 Fc, mFc.1, mFc.23, mFc.67.

Finally, three monomeric Fc proteins, mFc.1 (SEQ ID NO: 3), mFc.23 (SEQ ID NO: 5) and mFc.67 (SEQ ID NO: 4) were successfully developed. A sequence alignment of these three proteins is provided in FIG. 1D. The mFc.1 and mFc.23 contain seven mutations in CH3 dimer interface while mFc.67 contains six. Although they include different mutations, all of them were expressed in *E. Coli* with high efficiency. Purified monomeric Fc were obtained with yields of 15-20 mg homogenous protein per liter culture. This is surprisingly even better than that of wild-type Fc, which is no more than 10 mg per liter culture. Size exclusion chromatography results in only one peak corresponding to pure monomer with molecular weight of approximately 27 kD (FIG. 2A).

Example 3

Mutations in Monomeric Fc are Essential to Maintain a Soluble Monomer

To determine which residues are important to Fc dimer formation, a reverse mutation assay was conducted, in which the point mutations in mFc.23 were changed back to their original counterparts in wild-type Fc. Six mFc.23 mutants, S351L, R366T, H368L, R366T/H368L, K395P and E405F/K407Y/A409K were generated. They were expressed and purified using a similar procedure as for monomeric Fc proteins, and then analyzed by size exclusion chromatography (FIG. 2B). Some shoulder peaks appeared near monomer peaks for the reverse mutants S351L, R366T and R366T/H368L, suggesting formation of small proportion of dimers. Although only a single peak was observed for H368L or K395P, the shape of the peak became broad and distorted.

The E405F/K407Y/A409K mutant of mFc.23 (mFc.23.4) appeared completely monomeric. Taken together, these results suggest that four amino acid residues/mutations are essential for formation of mFc.

Example 4

Stability of mFc

To test the thermal stability of the mFcs, their CD spectra as a function of temperature were measured. CD ellipticity at 216 nm plotted against temperature was used to establish the thermal stability of the proteins (FIG. 3A). The midpoint transition temperatures (Tms) for Fc, mFc.1, mFc.23, and mFc.67 were 75.1±0.5° C., 45.0±0.6° C., 45.2±0.6° C. and 51.0±0.5° C., respectively. The thermal refolding was reversible, indicated by the fact that CD spectra of the samples on cooling down from 90° C. almost totally matched the original measurements (FIG. 3B).

The stability was further tested by urea denaturation experiments monitored by fluorescence spectroscopy. The 50% unfolding of Fc occurred at higher urea concentrations (5.8 M) than that of mFc.1 (4.1 M), mFc.23 (4.1 M), mFc.67 (4.3 M) and CH2 (4.2 M).

Figure 4B:
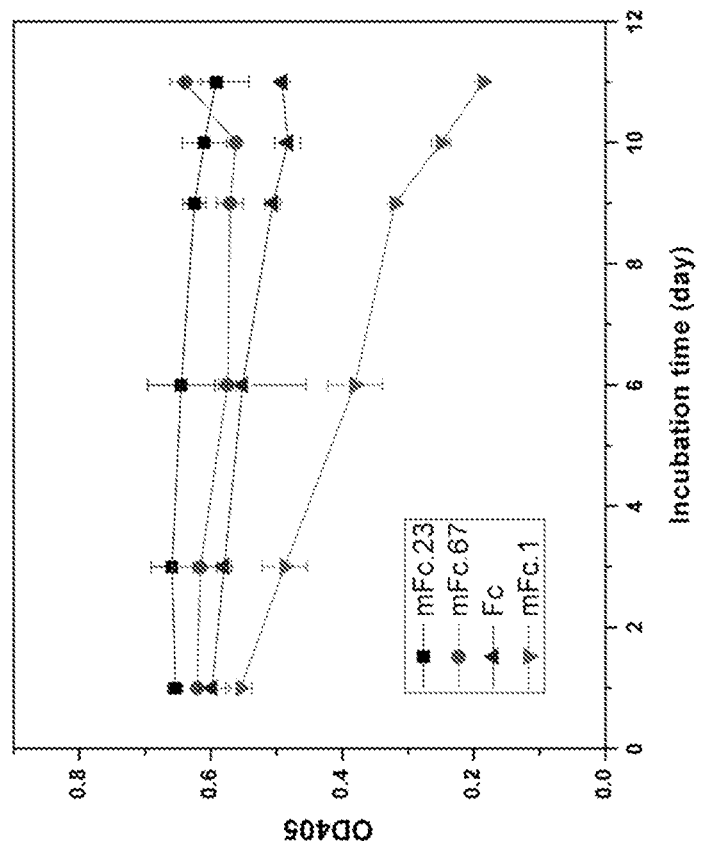
FIG. 4B Serum stability of Fc, mFc.1, mFc.23 and mFc.67 as measured by ELISA. For the ELISA, plates were coated with anti-Fc $F(ab')_2$ and anti-FLAG HRP conjugate was used for detection.
Figure 4A:
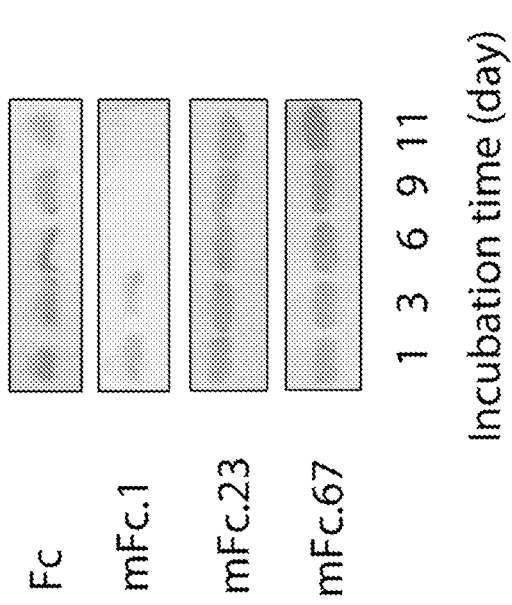
FIG. 4A Serum stability of Fc, mFc.1, mFc.23 and mFc.67 as measured by Western blot.

The serum stability of the monomeric Fc proteins was evaluated. Samples were incubated with human serum at 37° C., and an aliquot was taken out at each time point and stored at −80° C. before Western blot analysis (FIG. 4A). While the band disappeared for mFc.1 after 3 days' incubation, the bands were not evidently diminished for Fc, mFc.23 and mFc.67 even after an 11-day's incubation. We further assess the protein degradation by ELISA. Anti-Fc Fab was coated on ELISA plates to capture Fc and monomeric Fc, and anti-FLAG-HRP conjugate were used for detection. From FIG. 4B, it is evident that Fc, mFc.23 and mFc.67 were degraded more slowly than mFc.1. Without being bound by theory, some mutations in mFc.1 could make it easier to be cleaved by proteases in human serum. The ELISA signals did not decrease too much even for the samples after 11 days' incubation, suggesting that Fc, mFc.23 and mFc.67 have high serum stability.

Example 5

Monomeric Fc Bind FcRn

Figure 5A:
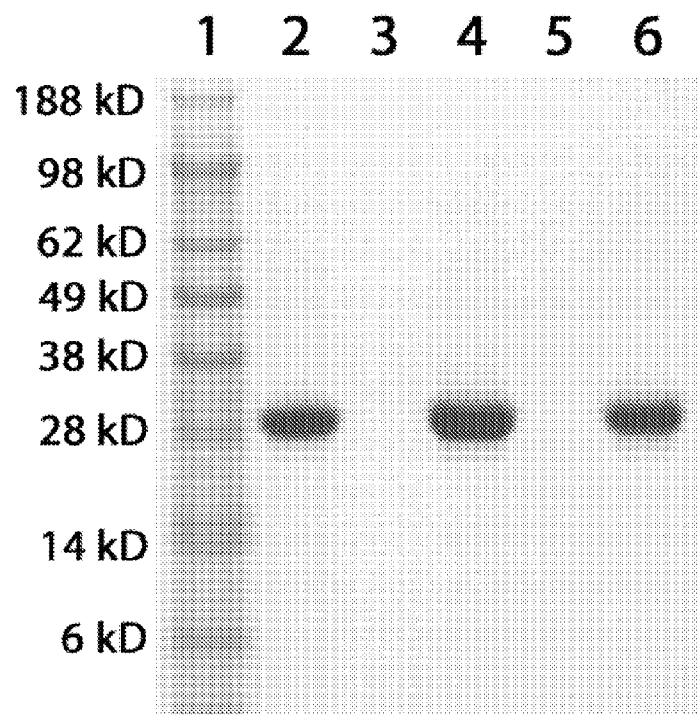
FIG. 5A The flow-through and elution of mFc.1 from protein A and protein G columns were analyzed by SDS-PAGE.

To test whether these monomeric Fc are functional and behave in a similar way as wild-type Fc, it was first checked if they could still bind protein A and protein G. A monomeric Fc, mFc.1, was applied to a pre-equilibrated protein A and a protein G column, respectively. The flow-through and elution from the columns were analyzed by SDS-PAGE (FIG. 5A). Clearly, all proteins were bound to the columns, indicating monomeric Fc could bind strongly to protein A and protein G.

It was then examined whether monomeric Fc could functionally bind FcRn. The pH-dependence of the binding was examined using ELISA. As can be seen in FIG. 5B, all three mFcs exhibited comparable human FcRn binding activities to wild-type Fc at pH 6.0. Binding was greatly reduced at pH 7.4. A mutated Fc, in which four residues in the FcRn binding interface of Fc were mutated to alanine (Fc I253A/S254A/H435A/Y436A mutant), did not bind FcRn, confirming that the experimental system was functional.

To further confirm the pH-dependent binding of monomeric Fc to FcRn and to obtain relatively reliable binding constants, surface plasmon resonance (SPR) experiments were performed. Human FcRn was immobilized on a CM5 bio sensor chip followed by analysis of the interaction using BIAcore X100. The binding was performed under pH 6.0 and pH 7.4, respectively, and the chip was regenerated with pH 8.0 buffer. At pH 6.0, the calculated binding affinity ($K_D$) of wild-type Fc, mFc.1, mFc.23 and mFc.67 to human FcRn was 126, 204, 59 and 111 nM, respectively. As shown in FIG. 5C, the mFc displayed a similar behavior to wild-type Fc. Both the mFcs and wild-type Fc did not show any detectable binding to FcRn at pH 7.4. Taken together, these results demonstrate that the mFc maintained the characteristic pH dependence of binding to FcRn.

Example 6

Monomeric Fc in Fusion Proteins

Figure 6B:
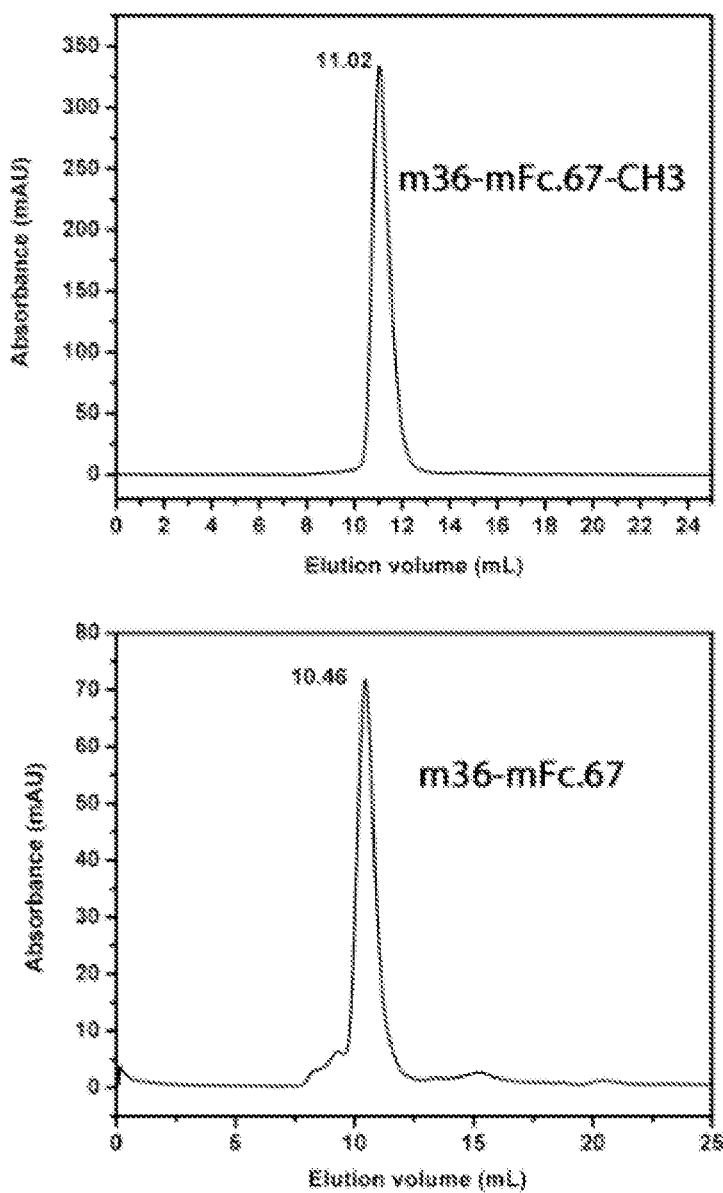
FIG. 6B Size exclusion chromatography of m36-mFc.67$^{cH3}$ and m36-mFc.67 fusion proteins.

It was determined if the monomeric Fc can be used to produce fusion proteins. M36, a human antibody variable domain (VH) that can target HIV-1 envelope glycoprotein (Env), was used to construct fusion proteins with a monomeric Fc, mFc.67. Two versions of fusion proteins were generated, as shown in FIG. 6A, one is m36 with mFc.67 (MW ~27 kD) and the other is m36 with only the CH3 domain of mFc.67 (MW ~39 kD). Both molecules were efficiently expressed in *E. Coli*, with yields of ~20 mg/L for m36-mFc.67$^{CH3}$ fusion protein and 5-10 mg/L for m36-mFc.67 fusion protein. Size exclusion chromatography results indicated that they are both in pure monomeric forms (FIG. 6B).

Figure 6C:
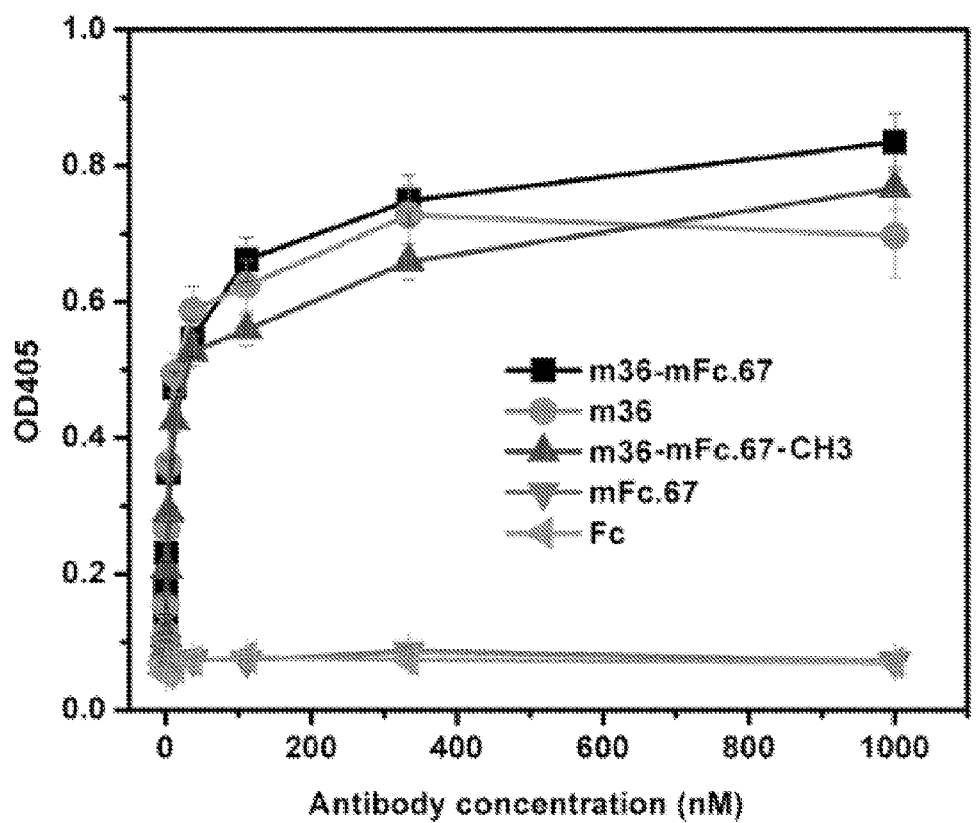
FIG. 6C Binding of m36 and fusion proteins to gp120$_{BaL}$-CD4 measured by ELISA.
Figure 7A:
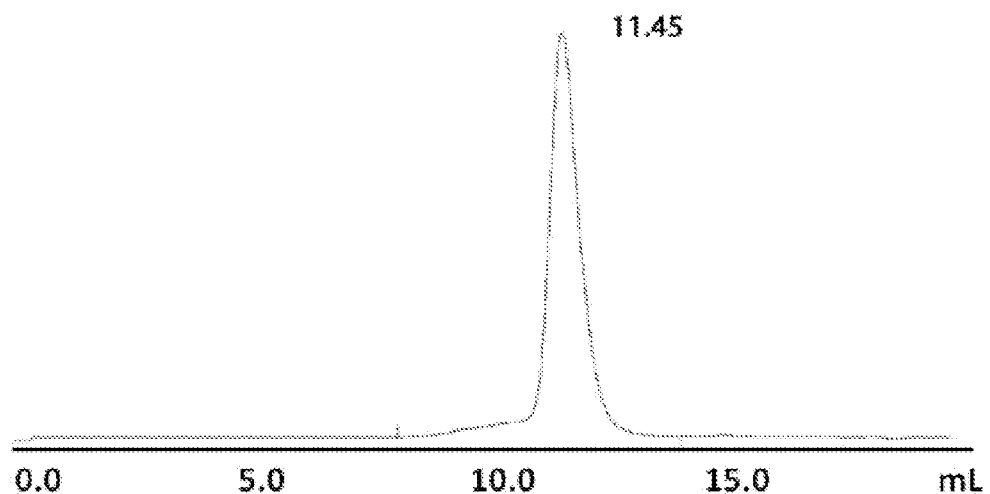
FIG. 7A Monomeric Fc mFc.23.4 (mFc.23 405F/407Y/409K reverse mutant) can be kept at high concentration (100 mg/mL).
Figure 7B:
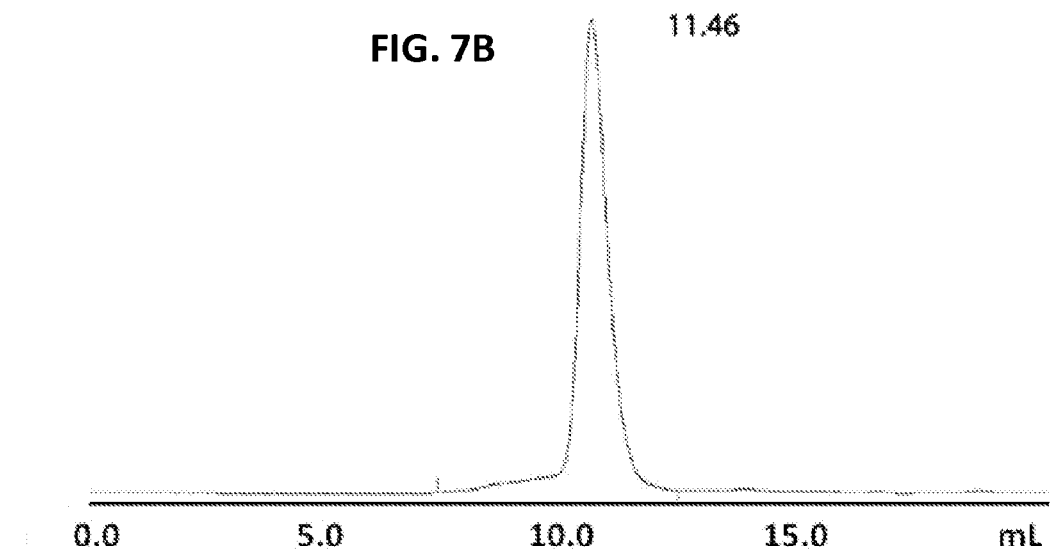
FIG. 7B The mFc.23.4 protein solution (100 mg/mL) was kept at room temperature for one week and there was no precipitate at all and the protein was still pure monomeric, as indicated by SEC. The molecular composition of purified proteins was analyzed by size exclusion chromatography (SEC) using an FPLC AKTA BASIC pH/C system (GE Healthcare) with a Superdex 75 10/300 GL column (GE Healthcare).

It was assessed whether the effector molecules in monomeric Fc fusion proteins are still active. M36 exhibits potent broadly neutralizing activity against HIV-1 by targeting a highly conserved CD4 binding-induced structure on the envelope glycoprotein gp120. As shown in FIG. 6C, m36 and the two fusion proteins, m36-mFc.67 and m36-mFc.67$^{CH3}$, exhibited comparable binding to gp120$_{Bal}$-CD4 as measured by ELISA. Wild-type Fc and mFc.67 monomer did not show any binding ability. These results confirmed that monomeric Fc can be used to develop functional fusion proteins.

Thus, several monomeric Fc were generated using the combination of rational design and multiple screening methods. It has been determined that a surprisingly large number of proteins are in oligomeric states in nature, and many among them are "compulsory complexes" in which free monomers are not available. Although much effort has been put into the breaking of such oligomers in order to move an existing oligomeric protein into a new functional realm, in most cases the engineered monomers were insoluble or poor structured.

Without being bound by theory, poor monomer quality may come from the exposure of oligomerization interface, and the replacement of residues responsible for oligomer formation is likely to make little impact on the biological functions of a monomer. In this regard, very large libraries could be constructed and desired monomer could be selected by directed evolution. A multiple screening strategy provides multiple evolutionary pressure. In the present case, screening of the library directly against FcRn did not yield any monomers, but an additional screening against protein G, before the FcRn screening, successfully produced some highly soluble and functional monomers. In fact, the work disclosed herein is a rare example where the yield of monomer protein even surpasses that of the wild-type. This screening strategy could be extended to other cases of monomer development, and expand the arsenal of protein engineering.

A significant application of monomeric Fc is for the so-called "monomeric Fc fusion" technology where a monovalency of the active protein is presented but currently it is fused to dimeric wild-type Fc. This "monomeric" technology is different from the traditional dimeric Fc fusion molecules, which contain two effector molecules. Better tissue penetration offered by this smaller construction, and a reduced steric hindrance which can make effector protein and/or Fc part more effective. For example, Peters et al. found that "monomeric" factor IX (FIX)-Fc fusion protein has not only extended half-life than the FIXFc dimer, but also greatly enhanced pharmacokinetics, with a 10-fold increase in $C_{max}$ and more than 12-fold increase in AUC (Peters, R. T., et al., Blood, 2010. 115(10): p. 2057-64). The experiments described herein document that monomeric Fc, which is only half the size of Fc dimer but retains FcRn binding ability, can replace dimeric Fc and generate real monomeric Fc fusion proteins. This construction includes only one effector molecule and one Fc monomer, so that size is largely reduced compared to the "monomeric" proteins that are currently available.

Monomeric Fc represents a novel antibody format in the field of therapeutic antibodies. Currently, monoclonal antibodies have enjoyed widespread therapeutic applications, and represent the largest class of biological drugs. However, antibody therapeutics have well-demonstrated difficulty in penetrating tissues due to their large size. A variety of small antibody formats, such as Fab, Fv, scFv, VH and VHH, have been developed but at the expense of their in vivo half-lives. It is disclosed herein that fusion proteins of variable domains that bind an antigen can be made with a monomeric Fc. The resulting fusion proteins have prolonged half-life and molecular weight of ~40 kD, only one fourth that of full-size IgG.

The monomers disclosed herein can be expressed in *E. Coli* with high efficiency, are relatively stable, and retain the ability to bind FcRn in a pH dependent manner. These proteins are building blocks for monomeric Fc based antibody engineering, so that antigen binding molecules are produced that have a small size, long in vivo half-life, as high binding affinity for any antigen of interest.

Example 7

Antigen Binding Monomeric Fc mFcs themselves can serve as novel antibody formats and be used as scaffolds for construction of libraries containing diverse binders to various antigens. They are relatively stable, can bind FcRn in a pH-dependent manner, and can be produced in large quantities in bacteria. More importantly, compared to wild-type Fc a large surface area is exposed in Fc monomer due to the breaking of CH3 dimerization interface. This provides more accessibility for protein engineering by designed point mutations and CDR-grafting onto monomeric Fc framework. Binders generated from such design have molecular weight of approximately 27 kD, similar to that of scFv but possess much longer in vivo half-life. Schematic diagrams of monomeric Fc that bind an antigen are provided in FIG. 8.

The material and methods for libraries construction and panning are:

Library Construction: Large phage display libraries (each with more than 10 to 10 individuals) were constructed by three different ways: (a) randomly mutating residues in the CH2 domain of monomeric Fc (K246, R301, V303, V305); (b) randomly mutating residues in CH2 domain (K246, R301, V303, V305) as well as CH3 domain (residues 389 to 393, NNYKT) of monomeric Fc; (c) randomly mutating residues in CH2 domain (K246, R301, V303, V305), and naturally occurring heavy chain CDR3s were grafted into CH3 domain (residues 389 to 393) of monomeric Fc.

Naturally occurring heavy-chain CDR3s were grafted from five template libraries. These template libraries include: (a) a naïve human Fab library ($5 \times 10^9$ members) from peripheral blood B cells of 10 healthy donors; (b) a naïve human Fab library ($1.5 \times 10^{10}$ members) from peripheral blood B cells of 22 healthy donors, spleens of 3 donors, and lymph nodes of 34 healthy donors; (c) two naïve human Fab libraries ($6 \times 10^8$ and $7.2 \times 10^8$ members, respectively) from cord blood of two healthy babies, respectively; and (d) an immune human Fab library from the bone marrow of three long-term non-progressors whose sera exhibited the broadest and most potent HIV-1 neutralization among 37 HIV-infected individuals. The grafted CDR3s were inserted into CH3 domain of mFc to replace the residues 389 to 393 (NNYKT).

The primers used for CDR3s grafting are shown below.

Overlapping PCR was used to introduce random mutations to monomeric Fc to generate the libraries. The primers used were described in Table 2. PCR fragments were subjected to SfiI digestion and ligated to the pCOM3X vector. The ligated product was desalted and transformed to the electrocompetent TG1 cells using an electroporator.

Antibody Selection by Phage Display: Purified gp120 or nucleolin was labeled with biotin first and used for panning of the libraries constructed above. Briefly, amplified phage ($10^{12}$ plaque-forming unit) preabsorbed with MYONE™ streptavidin T1 beads (Invitrogen) was incubated with 4 μg of biotin-antigen for 2 hours. Specific phages were captured by fresh streptavidin beads. After extensive washes of the beads with PBS+0.05% TWEEN® 20, phage was rescued by exponentially growing TG1 bacteria and helper phage. Four to six rounds of sequential panning was performed. Clones that bound to antigens were identified by using monoclonal phage ELISA.

Primers Used for CDR3 Grafting

```
NewCDR3MFC IF-1
                                       (SEQ ID NO: 16)
5'-ATCGCCGTGGAGTGGGAG AGC GTW TAT TAC TGT-3'

NewCDR3MFC IF-2
                                       (SEQ ID NO: 17)
5'-ATCGCCGTGGAGTGGGAG AGC DTG TAT TAC TGT-3'

NewCDR3MFC IIF
                                       (SEQ ID NO: 18)
5'-ATCGCCGTGGAGTGGGAG AGC AAT TAT TAC TGT-3'

NewCDR3MFC IIIF
                                       (SEQ ID NO: 19)
5'-ATCGCCGTGGAGTGGGAG AGC AAT GGG TAC TGT-3'

NewCDR3MFC IVF
                                       (SEQ ID NO: 20)
5'-ATCGCCGTGGAGTGGGAG AGC AAT GGG CAG TGT-3'

NewCDR3MFC VF
                                       (SEQ ID NO: 21)
5'-ATCGCCGTGGAGTGGGAG AGC AAT GGG CAG GGT-3'

NewCDR3MFC IR-1
                                       (SEQ ID NO: 22)
5'-GAAGGAGCCGTCGGAGTC CAG YCC TTG GCC CCA-3'

NewCDR3MFC IR-2
                                       (SEQ ID NO: 23)
5'-GAAGGAGCCGTCGGAGTC CAG BCC CTG GCC CCA-3'

NewCDR3MFC IIR-1
                                       (SEQ ID NO: 24)
5'-GAAGGAGCCGTCGGAGTC CAG CAC TTG GCC CCA-3'

NewCDR3MFC IIR-2
                                       (SEQ ID NO: 25)
5'-GAAGGAGCCGTCGGAGTC CAG CAC CTG GCC CCA-3'

NewCDR3MFC IIIR
                                       (SEQ ID NO: 26)
5'-GAAGGAGCCGTCGGAGTC CAG CAC GGG GCC CCA-3'

NewCDR3MFC IVR
                                       (SEQ ID NO: 27)
5'-GAAGGAGCCGTCGGAGTC CAG CAC GGG GAC CCA-3'

NewCDR3F1
                                       (SEQ ID NO: 28)
5'-GCCGTGGAGTGG GAG GCC GTW TAT TAC TGT-3'

NewCDR3F2
                                       (SEQ ID NO: 29)
5'-GCCGTGGAGTGG GAG GCC DTG TAT TAC TGT-3'

NewCDR3R1
                                       (SEQ ID NO: 30)
5'-GGAGCCGTCGGA GTC GGT YCC TTG GCC CCA-3'

NewCDR3R2
                                       (SEQ ID NO: 31)
5'-GGAGCCGTCGGA GTC GGT BCC CTG GCC CCA-3'

CDR3MFC END-R
                                       (SEQ ID NO: 32)
5'-CTG CCC ATT GCT CTC CCA C-3'

CDR3MFC END-F
                                       (SEQ ID NO: 33)
5'-GTC CCC GTG CTG GAC TCC G-3'

In the following primers, N = A + G + T + C,
B = T + C + G, V = A + C + G
Mut1
                                       (SEQ ID NO: 34)
5'-GACTGACGGTCCCCCCAGGAGTTCAGGTG-3'

Mut2
                                       (SEQ ID NO: 35)
5'-ggga ccgtcagtc NNB ctc NNB ccc cca NNB ccc
aaggacaccc-3'

Mut3
                                       (SEQ ID NO: 36)
5'-Tcacgtccaccac VNN gca VNN gacctcaggggtc-3'

Mut4
                                       (SEQ ID NO: 37)
5'-GTGGT GGACGTGAGC CACGAAGACC-3'
```

-continued

Mut5
(SEQ ID NO: 38)
5'-GTACGTGCTGTTGTACTGCTCC-3'

Mut6
(SEQ ID NO: 39)
5'-caacagcacgtac NNB gtg NNB agcgtcctcaccg-3'

Mut7
(SEQ ID NO: 40)
5'-TTTGGAGATGGTTTTCTC-3'

Mut8
(SEQ ID NO: 41)
5'-GAAAACCATCTCCAAANNBNNBNNBNNBCCCCGAGAACCACAGG-3'

Mut9
(SEQ ID NO: 42)
5'-CACGGGGACCGTGGTCTTGTAG-3'

Mut10
(SEQ ID NO: 43)
5'-ACC ACG GTC CCC GTG NNB NNB NNB NNB GGC TCC TTC AGG CTC G-3'

Primers Used for Constructing mFc Mutation Libraries

Monomeric Fc domains were generated wherein one or two residues around amino acid 16 (K), amino acid 71 (R) to 75 (V), 159 (N) to 163 (T) were mutated. In some cases, a CDR was inserted between residues 159 (N) to 163 (T), which are in CH3 domain to replace the original amino acids. It should be noted that residue 16 corresponds to residue 246 in IgG1 numbering system, etc. The sequences of the antigen binders are shown in FIG. 9.

Figure 10:
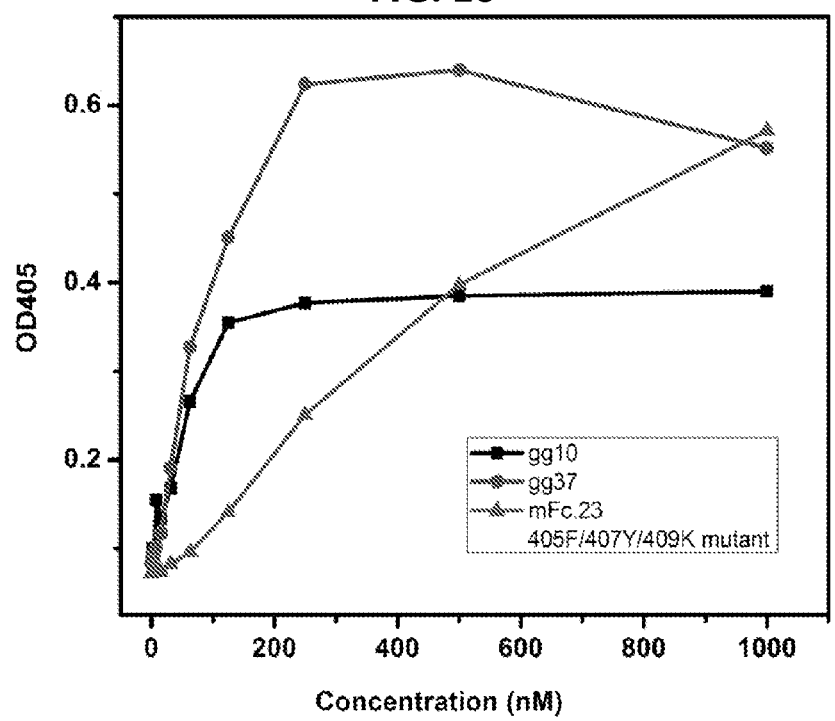
FIG. 10 is a graph of ELISA data from gg10 and gg37, which are monomeric Fc domains that bind gp140. The binder gg10 has only 4 mutations in CH2 and no mutations in CH3. gg37 has several mutations in CH2 but also a grafted CDR in the CH3 domain
Figure 11:
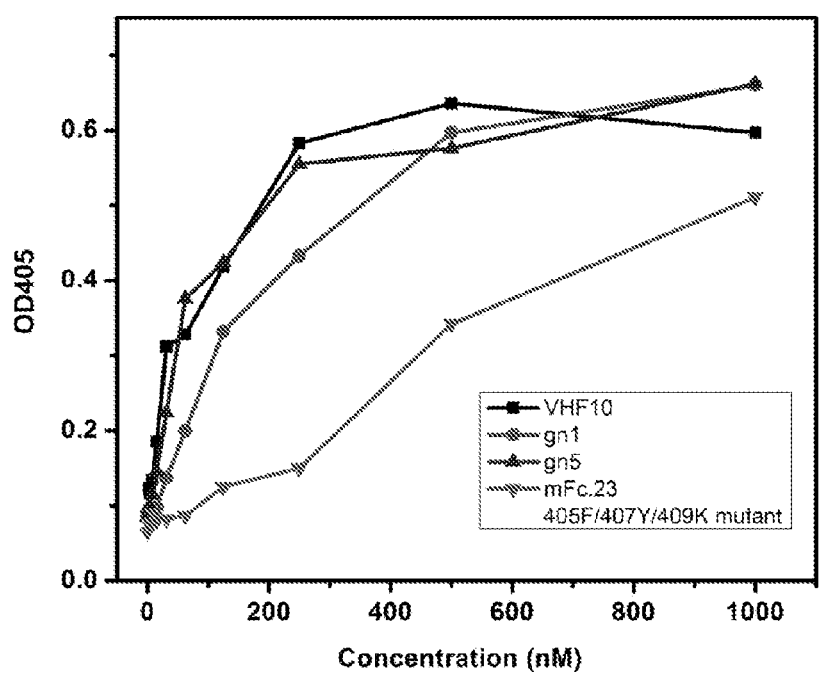
FIG. 11 is a graph of ELISA data from gn1 and gn5, which bind nucleolin (NCL). VF10 is a VH that binds NCS that is used as a positive control. Gn1 and gn5 have several mutations in CH2 and a grafted CDR in the CH3 domain.

The affinities of the binders gg10, gg37 and gn1 are about 50 nM, and gn5 is about 30 nM. This is shown in FIGS. 10-11)

Example 9

Di-Sulfide Stabilized Monomeric Fc

The 242C/334C/343C/431C mutants were generated by the QUIKCHANGE® Site-Directed Mutagenesis Kit (Stratagene). The mutants were expressed and purified similarly to the wild-type Fc and monomeric Fc. For evaluation of thermal stability, the CD spectra were collected with an AVIV® Model 202 spectropolarimeter (AVIV® Biomedical). Proteins were dissolved in PBS, pH 7.4 at the final concentration of 0.25 mg/mL. CD signals at 216 nm were recorded. The instrument was programmed to acquire spectra at 1° C. intervals over the range 25-90° C.

Figure 12A:
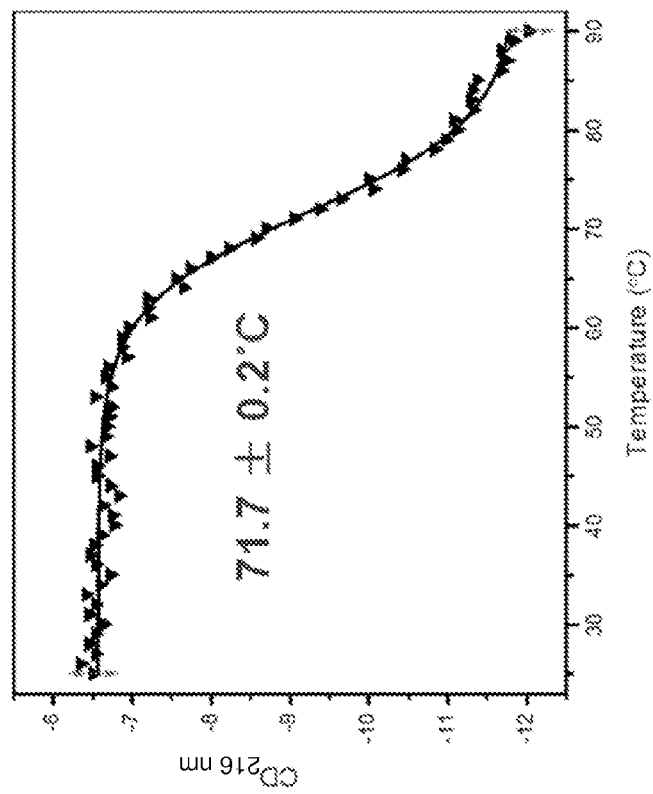
FIGS. 12A and 12B are two plots of the change in fraction folded (calculated from CD molar ellipticity at 216 nm) for mFc.23.4 (FIG. 12A) and the mFc.23.4 242C/334C/343C/431C mutant (FIG. 12B).
Figure 12B:
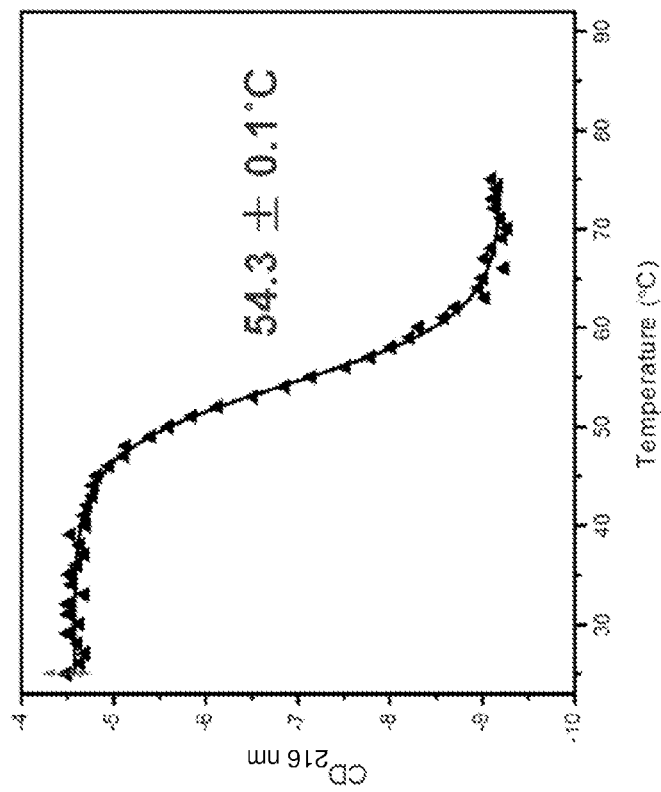

The midpoint transition temperature (Tm) of mFc.23.4 is 54.3° C. The Tm of mFc.23.4 242C/334C/343C/431C mutant is 71.7° C., see FIG. 12A-12B. The mFc.23.4 242C/334C/343C/431C mutant is still monomeric.

Example 10

CH3 Domain Molecules

The CH3 gene was cloned into the pComb3x vector and tested for soluble expression in E. coli. The soluble-expressed monomeric CH3 domain (mCH3) includes four mutated residues relative to the wild-type CH3, all located in the dimerization interface (residues 351, 366, 368 and 395). Purified mCH3 was obtained with a yield of 2 mg/L bacterial culture, which was lower than that of mFcs. The Fc CH3 domain was cloned from Fc with the same primers that were used to generate mCH3, and the protein expression level was found to be 15 mg/L.

A monomeric Fc protein, mFc.67 and the wild-type Fc were also expressed and purified. mCH3 was monomeric with a molecular size of approximately 14 kDa. The wild-type CH3 existed as a pure dimer (MW ~28 kDa). The CH3 and Fc dimers migrated as monomers under denaturing conditions of SDS-PAGE analysis. Interestingly, it was found that mCH3 migrated at a slower rate than the wild-type CH3. The mobility difference may be linked to different charge or conformational states between mCH3 and its wild-type counterpart.

Figure 13A:
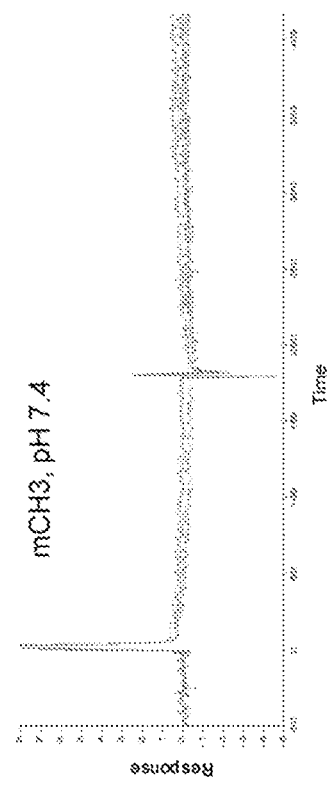
FIGS. 13A-13D shows FcRn binding of mCH3 (FIG. 13A), CH3 (FIG. 13C), CH2 (FIG. 13D) at pH 6.0, and mCH3 at pH 7.4 (FIG. 13B) measured by BIAcore.
Figure 13B:
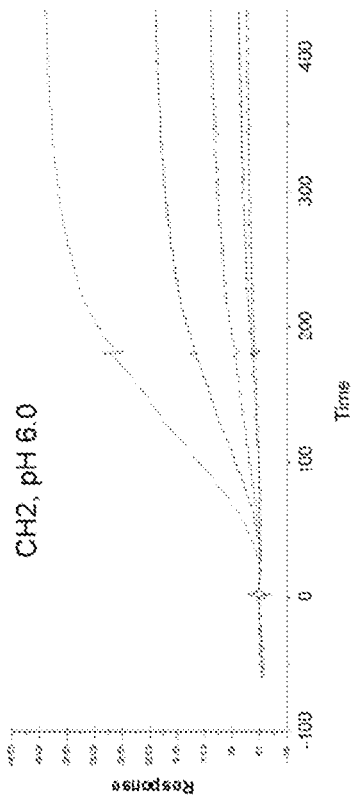
Figure 13C:
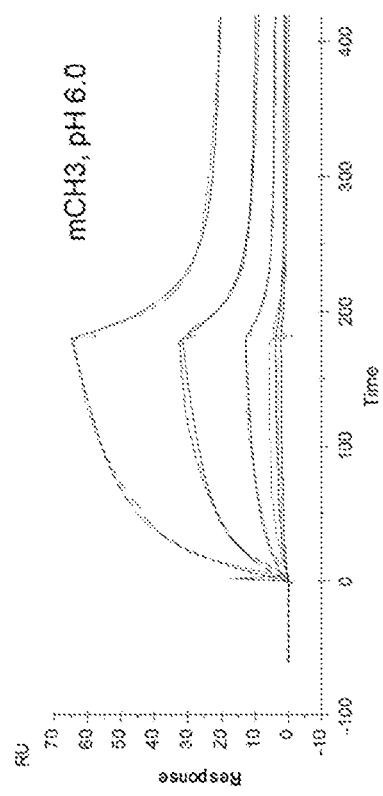

It was determined whether mCH3 could bind FcRn in a pH-dependent manner. Surface plasmon resonance (SPR) binding was performed using a BIAcore instrument with human FcRn immobilized on the chip, as described previously. The measurements were carried out under pH 6.0 or pH 7.4, and the chips were regenerated after binding by injection of a pH 8.0 buffer. While the isolated CH3 did not show any FcRn binding at either pH 6.0 or pH 7.4, it is remarkable that significant binding was observed at pH 6.0 for mCH3, in contrast to a lack of binding at pH 7.4 (FIG. 13A-C). Since mCH3 has a different conformation from that of the isolated CH3, it is possible that the conformational changes have made the binding site in mCH3 more accessible to FcRn than in the isolated CH3 dimer, thereby conferring pH-dependent binding capability.

Figure 13D:
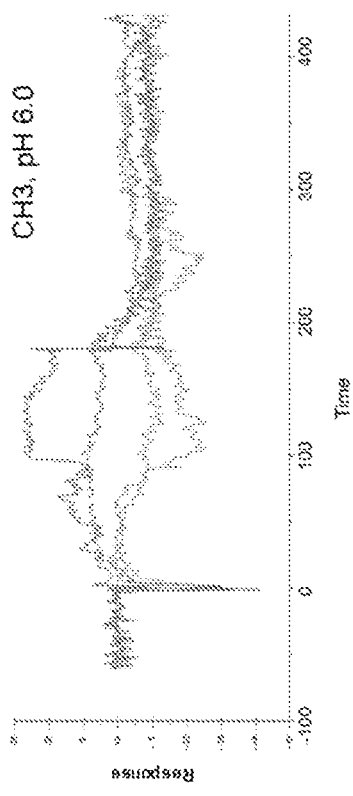

The calculated binding affinity ($K_D$) of mCH3 was 940 nM. As expected, the binding affinity was not as high as the wild-type Fc, which has been shown to bind with a $K_D$ of 126 nM. Given the fact that both the CH2 and CH3 domain of IgG Fc contribute to the binding of FcRn, the binding affinity of the isolated CH2 to FcRn was also determined. However, there was an unusual delay during the association phase, and the dissociation of CH2 to the chip was very slow (FIG. 13D). No fitting model could be found for this abnormal binding pattern.

It was noted that the CM5 chip could be better regenerated by pH 8.0 buffer after the mCH3 binding measurement compared to after the Fc measurement, although neither of the two proteins showed detectable binding at pH 7.4. These behaviors are not surprising since most of the interface residues of Fc/FcRn binding in the CH2 domain are involved in hydrophobic interactions, which were thought to be inherently "sticky," as exemplified by I253 and S254. In contrast, the FcRn binding residues in the CH3 domain could participate in the formation of titratable salt bridges, which might confer pH dependence to the Fc/FcRn interactions, exemplified by H433 and H435. Without being bound by theory, the CH2 and CH3 domain may have distinct binding properties, and function differently when participating in the pH-dependent interaction with FcRn.

The ability of monomeric Fc to bind protein G was also assessed. The monomeric Fc (mFc.67) also had a high binding capability to protein G.

Example 11

The thermal stability of mCH3 is relatively low (Tm=40.6° C.). Although the mCH3 fusion protein exhibited significantly higher stability, additional stability could be introduced by protein engineering, which can lead to greater potential for industrial applications. A stabilized form, mCH3 343C/431C mutant (mCH3cc) was created to introduce an additional disulfide bond between Cys343 and Cys431, which can connect the N-terminal A strand and the C-terminal F strand of the CH3 monomer (FIG. 14A).

Remarkably, it was found mCH3cc was expressed in *E. coli* with higher efficiency than mCH3. Purified mCH3cc was obtained with a yield of more than 10 mg liter$^{-1}$ bacterial culture. It was significantly more stable than mCH3. The Tm of mCH3cc is 76.0±0.6° C., ~35° C. higher than that of mCH3 (40.6±0.3° C.) (FIG. 14B). The engineered CH3 monomer is also >99% monomeric as indicated by size exclusion chromatography. The binding affinity ($K_D$) of mCH3cc to FcRn was calculated to be 1.08 uM at pH 6.0, similar to that of the mCH3 (940 nM). No binding was detected at pH 7.4, indicating that the strictly pH-dependent FcRn binding capacity was retained.

Thus, an additional disulfide bond was engineered in mCH3 by introducing two cysteine mutations. The engineered mCH3 (mCH3cc) was found to have remarkably enhanced stability (the thermal transition midpoint, Tm, was increased from 40.6° C. to 76.0° C.), and a 5-fold boost in protein expression (10 mg purified protein per liter culture) over mCH3 (2 mg per liter culture). mCH3cc was also monomeric and fully retains the strictly pH-dependent FcRn binding capacity of mCH3.

It will be apparent that the precise details of the methods or compositions described may be varied or modified without departing from the spirit of the described invention. We claim all such modifications and variations that fall within the scope and spirit of the claims below.

---

The invention claimed is:

1. An isolated monomeric Fc polypeptide comprising a CH2 and a CH3 domain, wherein the Fc polypeptide comprises one of:
    (a) the amino acid sequence set forth as SEQ ID NO: 3;
    (b) the amino acid sequence set forth as SEQ ID NO: 4;
    (c) the amino acid sequence set forth as SEQ ID NO: 5;
    (d) the amino acid sequence set forth as SEQ ID NO: 6;
    (e) the amino acid sequence set forth as SEQ ID NO: 45;
    (f) the amino acid sequence set forth as SEQ ID NO: 46;
    (g) the amino acid sequence set forth as SEQ ID NO: 47; or
    (h) the amino acid sequence set forth as SEQ ID NO: 48.

2. The isolated monomeric Fc polypeptide of claim 1, consisting of one of:
    (a) the amino acid sequence set forth as SEQ ID NO: 3;
    (b) the amino acid sequence set forth as SEQ ID NO: 4;
    (c) the amino acid sequence set forth as SEQ ID NO: 5;
    (d) the amino acid sequence set forth as SEQ ID NO: 6;
    (e) the amino acid sequence set forth as SEQ ID NO: 45;
    (f) the amino acid sequence set forth as SEQ ID NO: 46;
    (g) the amino acid sequence set forth as SEQ ID NO: 47; or
    (h) the amino acid sequence set forth as SEQ ID NO: 48.

3. An isolated CH3 domain, comprising one of:
    (a) amino acids 113-217 of the amino acid sequence set forth as SEQ ID NO: 3;
    (b) amino acids 113-217 of the amino acid sequence set forth as SEQ ID NO: 4;
    (c) amino acids 113-217 of the amino acid sequence set forth as SEQ ID NO: 5;
    (d) amino acids 113-217 of the amino acid sequence set forth as SEQ ID NO: 6;
    (e) amino acids 113-217 of the amino acid sequence set forth as SEQ ID NO: 45;
    (f) amino acids 113-217 of the amino acid sequence set forth as SEQ ID NO: 46;
    (g) amino acids 113-217 of the amino acid sequence set forth as SEQ ID NO: 47; or
    (h) amino acids 113-217 of the amino acid sequence set forth as SEQ ID NO: 48.

4. An isolated fusion protein comprising the CH3 domain of claim 3 and a heterologous protein.

5. The isolated fusion protein of claim 4, wherein the heterologous protein comprises a heavy chain variable domain and a light chain variable domain, wherein the heavy chain variable domain and the light chain variable domain specifically bind an antigen of interest.

6. The isolated fusion protein of claim 4, wherein the heterologous protein is an antigen from a pathogen.

7. The isolated fusion protein of claim 6, wherein the pathogen is a virus or bacterium.

8. The isolated fusion protein of claim 7, wherein the virus is human immunodeficiency virus (HIV).

9. The isolated fusion protein of claim 4, wherein the heterologous protein is a cancer antigen.

10. The isolated fusion protein of claim 4, wherein the fusion protein comprises a toxin.

11. The isolated fusion protein of claim 4, wherein the heterologous protein is a cytokine, soluble receptor, growth factor, a human interferon, erythropoietin, soluble tumor necrosis factor receptor, CTLA-4, soluble IL-4 receptor, Factor IX or a label.

12. A composition comprising the monomeric Fc polypeptide of claim 1, a CH3 domain of the monomeric Fc polypeptide, a fusion protein comprising the monomeric Fc polypeptide or the CH3 domain of the monomeric Fc polypeptide, and a pharmaceutically acceptable carrier.

13. The isolated monomeric Fc polypeptide of claim 1, comprising the amino acid sequence set forth as SEQ ID NO: 3.

14. The isolated monomeric Fc polypeptide of claim 1, comprising the amino acid sequence set forth as SEQ ID NO: 4.

15. The isolated monomeric Fc polypeptide of claim 1, comprising the amino acid sequence set forth as SEQ ID NO: 5.

16. The isolated monomeric Fc polypeptide of claim 1, comprising the amino acid sequence set forth as SEQ ID NO: 6.

17. The isolated monomeric Fc polypeptide of claim 1, comprising the amino acid sequence set forth as SEQ ID NO: 45.

18. The isolated monomeric Fc polypeptide of claim 1, comprising the amino acid sequence set forth as SEQ ID NO: 46.

19. The isolated monomeric Fc polypeptide of claim 1, comprising the amino acid sequence set forth as SEQ ID NO: 47.

20. The isolated monomeric Fc polypeptide of claim 1, comprising the amino acid sequence set forth as SEQ ID NO: 48.

* * * * *